United States Patent
Reed et al.

(10) Patent No.: US 6,709,661 B1
(45) Date of Patent: Mar. 23, 2004

(54) LEISHMANIA ANTIGENS FOR USE IN THE THERAPY AND DIAGNOSIS OF LEISHMANIASIS

(75) Inventors: Steven G. Reed, Bellevue, WA (US); Antonio Campos-Neto, Bainbridge Island, WA (US); John R. Webb, Everett, WA (US); Davin C. Dillon, Redmond, WA (US); Yasir A. W. Skeiky, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 08/798,841

(22) Filed: Feb. 12, 1997

Related U.S. Application Data

(63) Continuation of application No. 08/533,669, filed on Sep. 22, 1995, now Pat. No. 5,834,592.

(51) Int. Cl.[7] .................. A61K 39/008; A61K 39/002; A61K 38/00; A61K 39/00
(52) U.S. Cl. ................ 424/269.1; 424/184.1; 424/85.2; 424/191.1; 424/192.1; 424/265.1; 514/12; 514/44; 514/2; 530/300; 530/350; 536/23.1; 536/23.6
(58) Field of Search ............ 530/350; 930/210; 424/184.1, 269.1, 265.1

(56) References Cited

U.S. PATENT DOCUMENTS

| | | | |
|---|---|---|---|
| 4,870,006 A | * | 9/1989 | Dragon et al. |
| 5,571,515 A | | 11/1996 | Scott et al. |
| 5,719,263 A | * | 2/1998 | Reed |
| 5,744,593 A | * | 4/1998 | Klimowski et al. |
| 5,834,592 A | | 11/1998 | Reed et al. |
| 5,876,735 A | * | 3/1999 | Reed |
| 5,876,966 A | * | 3/1999 | Reed |
| 5,879,687 A | * | 3/1999 | Reed |
| 5,965,142 A | * | 10/1999 | Dillon et al. |
| 6,013,268 A | * | 1/2000 | Reed |
| 6,054,135 A | * | 4/2000 | Reed et al. |

FOREIGN PATENT DOCUMENTS

| | | |
|---|---|---|
| WO | WO 95/29239 | 11/1995 |
| WO | WO 97/11180 | 3/1997 |

OTHER PUBLICATIONS

Afonso et al 1994 (Science, 263: 235–237).*
Levinson et al (Levinson et al Medical Microbiology & Immunology 1994, p. 293).*
Oligo sequence search reports for SEQ.ID.No.; 24 and 26.*
Cornelissen et al. FEMS Immunol & Med. Microbiol 15: 61–72, 1996.*
Skeeky et al. J. Exp. Med. 181: 1527–1537, Apr. 1995.*
Shapira and Pedraza, "Sequence analysis and transcriptional activation of heat shock protein 83 or *Leishmania mexicana amazonensis,*" *Molecular and Biochemical Parasitology* 42:247–256, 1990.

Skeiky et al., "A Recombinant Leishmania Antigen that Stimulates Human Peripheral Blood Mononuclear Cells to Express a Th1–Type Cytokine Profile and to Produce Interleukin 12," *J. Exp. Med. 181*:1527–1537, 1995.
Skeiky et al., "Proliferative And Cytokine Responses Of Human PBMC To Cloned *Leishmania Braziliensis* Heat Shock And Ribosomal Antigens," *Journal of Immunology 150*(8pt. 2):93A, Abstract #517, 1993.
EMBL Database Entry LDP23CSPR, Accession No. X86551, "*L. donovani* mRNA for 23kDa cell surface protein," Apr. 26, 1995.
Pir2 Database, Accession No. S54162, "*Leishmania donovani,*" Jul. 8, 1995.
De Andrade et al., "Recombinant Leishmania Hsp90 and Hsp70 Are Recognized by Sera from Visceral Leishmaniasis Patients but Not Chagas' Disease Patients," *Journal Of Clinical Microbiology 30*(2):330–335, 1992.
Bixler, Jr. and Atassi, *Synthetic Vaccines vol. 1,* CRC Press, Inc., Boca Raton, Florida 1987, Chapter 4, "B Cell Recognition Of Protein Antigens–Perspectives From The Submolecular Level," pp. 40–71.
Bowie et al., "Deciphering the Message in Protein Sequences: Tolerance to Amino Acid Substitutions," *Science 247*:1306–1310, 1990.
Campos–Neto et al., "Cloning and Expression of a *Leishmania donovani* Gene Instructed by a Peptide Isolated from Major Histocompatibility Complex Class II Molecules of Infected Macrophages," *J. Exp. Med. 182:*1423–1433, 1995.
Dillon et al., "Characterization of a *Leishmania tropica* antigen that detects immune responses in Desert Storm viscerotropic leishmaniasis patients," *Proc. Natl. Acad. Sci.* 92:7981–7985, 1995.
Frommel et al., "Vaccine–Induced Immunity against Cutaneous Leishmaniasis in BALB/c Mice," *Infection And Immunity 56*(4):843–848, 1988.
Houghten et al., "Relative Importance of Position and Individual Amino Acid Residues in Peptide Antigen–Antibody Interactions: Implications in the Mechanism of Antigenic Drift and Antigenic Shift," in *Vaccines 86,* Brown et al. (eds.), Cold Spring Harbor Laboratory, 1986, pp. 21–25.

(List continued on next page.)

*Primary Examiner*—Mark Navarro
*Assistant Examiner*—Padmavathi Baskar
(74) *Attorney, Agent, or Firm*—SEED Intellectual Property Law Group, PLLC

(57) ABSTRACT

Compositions and methods for preventing, treating and detecting leishmaniasis and stimulating immune responses in patients are disclosed. The compounds provided include polypeptides that contain at least an immunogenic portion of one or more Leishmania antigens, or a variant thereof. Vaccines and pharmaceutical compositions comprising such polypeptides, or DNA molecules encoding such polypeptides, are also provided and may be used, for example, for the prevention and therapy of leishmaniasis, as well as for the detection of Leishmania infection.

16 Claims, 28 Drawing Sheets

OTHER PUBLICATIONS

Mougneau et al., "Expression Cloning of a Protective Leishmania Antigen," *Science* 268:563–566, 1995.

Genbank Database, Accession No. U19888, Apr. 21, 1995.

Singh, S. et al., "Diagnostic and prognostic value of K39 recombinant antigen in Indian leishmaniasis," *Journal of Parasitology* 81(6): 1000–1003, Dec. 1995.

Webb, J.R. et al., "Molecular Cloning of a Novel Protein Antigen of *Leishmania major* That Elicits a Potent Immune Response in Experimental Murine Leishmaniasis," *Journal of Immunology* 157: 5034–5041, 1996.

* cited by examiner

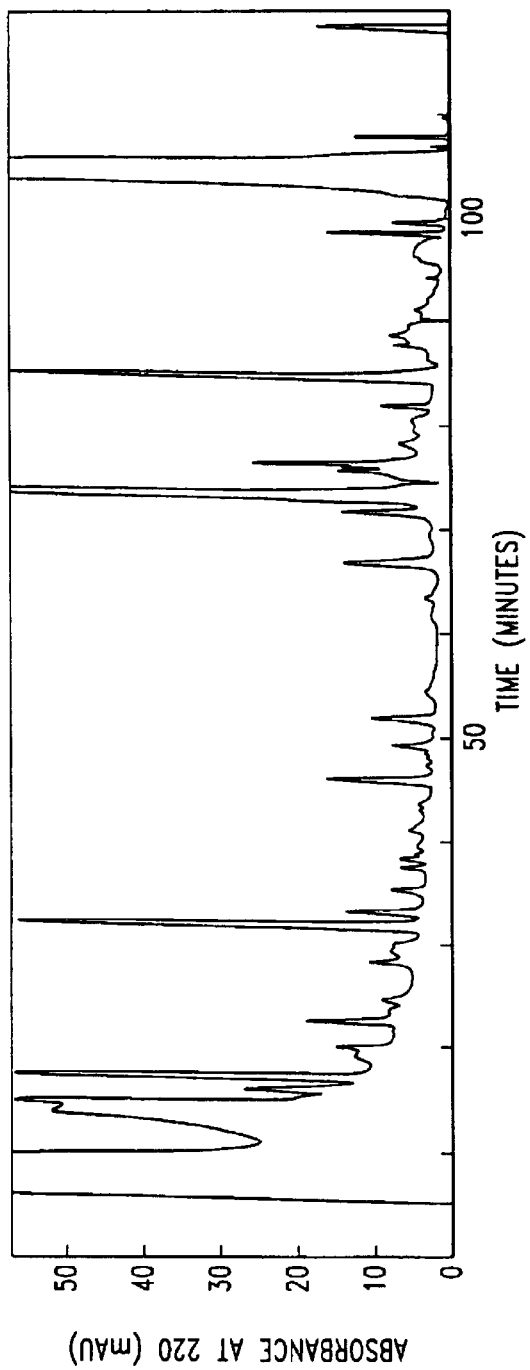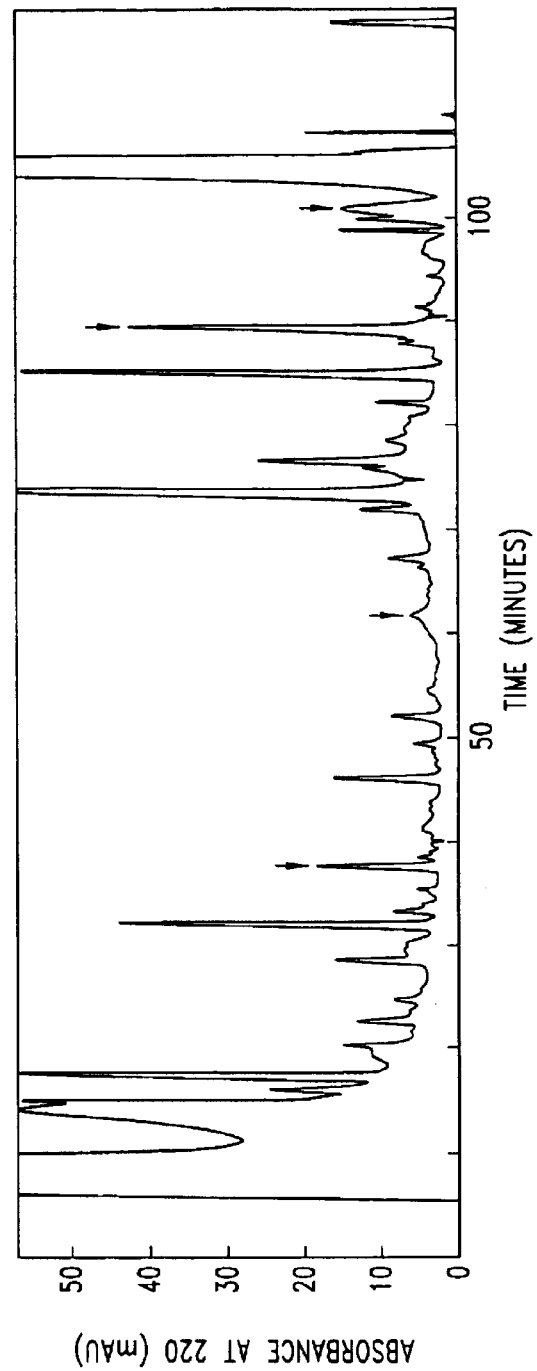
Fig. 2A
Fig. 2B

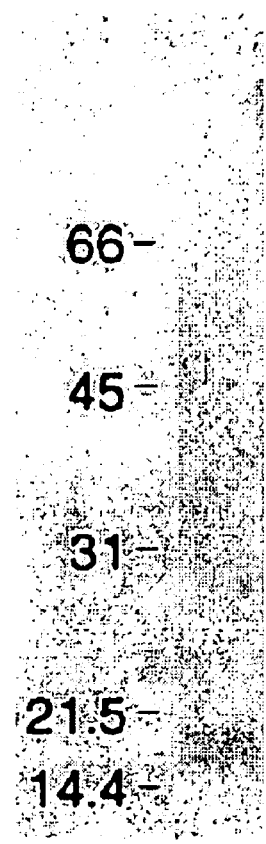 
*Fig. 5A*  *Fig. 5B*

```
                                            ----------------------------------------SLTDPAVLGEETHLRVRVVPDKANKTLTVEDNGIGMTK   85
                           MTETFAFQAEINQLMSLIINTFYSNKEIFLRDVISNASDACDKIRYQ.........DA.R.C.......E..............    85
                           ...........................................EL........NQ....D.S...I.............T......    85
            MPEETQTQDQPMEEEEV..........A....................EL...S....L.....E.....SK.DSGKE.HINLI.N.QDRA..IV.T......   100

P                                                  P
ADLVNNLGTIARSGTKAFMEALEAGGDMSHIGQFGVGFYSAYLVADRVTVVSKNNSDEAY-VESSAGGTFTITSVQESDMKRGTSTTLHLKEDQQEYLEE   184
................A....................T......V.V.............AP.....LPARI........L....A   185
.E.............................................D....T..........V.PTPDC.L....RIV............   185
...I......K.........Q..A.I.............EK...IT.H.D..Q.A.......S..VRTDTGEP.G...KVI.......T.....   200

RRVKELIKKHSEFIGYDIELMVEKTAEKEVTDE----DEEEDESKKKSCGDEGEPKVEEVTEGG-ED-KKKKTKKVKEVKKT-YEVK---NKHKPLVTRD   274
..L..........................T.......----,...---A..ADE.GE........-E..-........T.E-...Q---.   272
..L.D........................AT.......----..D.--AAATKNEEGE......KDDAE.GE........TQE-FV.Q---.   275
..I..IV....Q....P.T.F...ERD...S.DEAEEK..DKE.E.E.EEKESEDKPEI.DVGSDE..E..DGD..K.KKI.EK.ID.EEL..T..I...N   300

┌──Lbhsp83b
TKDVTKEEYAAFYKAISNDWEDTAATKHFSVEGQLEFRAIAFVPKRAPFDMFEPNKKRNNIKLYVRRVFIMDNCEDLCPDWLGFVKGVVDSEDLPLNISR   374
P......................PP.............M..........L...................................   372
P..............EPLS................L..............S.................E..A..R..........   375
PD.I.N...GE...SLT.....HL.V.............LL...R.....L..NR..K................E.I.EY.N..IR............   400

ENLQQNKILKVIRKNIVKKCLELFEEIAENKEDYKQFYEQFGKNIKLGIHEDTANRKKLMELLRFYSTESGEEMTTLKDYVTRMKPEQKSIYYITGDSKK   474
............M...V..........................................V.............A..N..........   472
............A............K.......V......S...........H.S....D..............EG..C...V......   475
.M...S........L.........T.L..D..N..K.....S..........SQ......S....Y.TSA..D..VS....C.....EN..H......ET.D   500

KLESSPFIEKARRCGLEVLFMTEPIDEYVMQQVKDFEDKKFACLTKEGVHFEESEEEKKQREEKKAACEKLCKTMKEVLGDKVEKVTVSERLLTSPCILV   574
.........Q.K.R.F.........Y...........................E..T................................S........   572
...T.....Q..R.F.......I..............................T........E.T.Y.R...A..D.......V....A........   575
QVAN.A.V.RL.KH....IY.I......CV..L.E..G.TLVSV....LELP.D.....KQ....TKF.N....I..DI.EK.....V..N..V....C..   600

P
TSEFGVSAHMEQIMRNQALRDSSMAQYMVSKKTMEVNPDHPIIKELRRRVEADENDKAVKDLVFLLFDTSLLTSGFQLDDPTGYAERINRMIKLGLSLDE   674
..............M.................H.....L..K............................E..-............   671
.............SA..M......I..A..V...K..........Y....A......T.....S......H.........D   675
..TY..T..N..R..KA......N.TMG...AA..HL.I....S..ET..QKA....K...S......I..YE.A..S...S.E..QTH.N..Y......GI..   700

EE---EEVA-EAPPAEAAPAEVTAGTSSMEQVD   703   Lbhsp83
..E--..E.V..AV..T............L.    701   Lohsp83
.D---NGNE..E..A.V...PV..........   704   Tchsp83
DDPTADDTSA.VTE.MP.L.GDDD..R..E..   734   Huhsp89
```

*Fig. 19*

```
GAATTCGGCACGAGGTTTCTGTACTTTATTGCTTCCAGCCTTTATTCACTCTTCGATTTCCTCTAACACCATGTCCTCCGAGCGCACCTTTATTGCCGTC  100
|5'-Adaptor|Spliced-leader|       5'-UT                    |
                                                                            M  S  S  E  R  T  F  I  A  V
AAGCCGGACGGCGTGCAGCGCGGCCTCGTTGGCGAGATCATCGCCCGCTTCGAGCGCAAGGGCTACAAGCTCGTCGCCTTGAAGATACTGCAGCCGACGA  200

K  P  D  G  V  Q  R  G  L  V  G  E  I  I  A  R  F  E  R  K  G  Y  K  L  V  A  L  K  I  L  Q  P  T
CGGAGCAGGCCCAGGGTCACTATAAGGACCTTTGCTCCAAGCCGTTTTTCCCGGCCCTTGTGAAGTACTTCTCCTCTGGCCCGATCGTGTGTATGGTGTG  300

T  E  Q  A  Q  G  H  Y  K  D  L  C  S  K  P  F  F  P  A  L  V  K  Y  F  S  S  G  P  I  V  C  M  V  W
GGAGGGTAAGAACGTGGTGAAGAGCGGCCGCGTGCTGCTCGGCGCGACGAACCCGGCCGACTCACAGCCCGGCACGATCCGTGGCGACTTTGCCGTGGAT  400

E  G  K  N  V  V  K  S  G  R  V  L  L  G  A  T  N  P  A  D  S  Q  P  G  T  I  R  G  D  F  A  V  D
GTGGGCCGCAACGTGTGCCACGGGTCCGACTCTGTGGAGAGCGCGGAGCGCGAGATCGCCTTTTGGTTCAAGGCGGATGAGATCGCGAGCTGGACGTCGC  500

V  G  R  N  V  C  H  G  S  D  S  V  E  S  A  E  R  E  I  A  F  W  F  K  A  D  E  I  A  S  W  T  S
ACTCCGTGTCCAGATCTATGAGTAACGGTGATTGCGGACACGCTTTGAGGACGTAGCTGTACCCCCAATGAATTCTTCTCTGAAAACCACATCATAAGC  600
                                                                 |          3'-UT                  |
H  S  V  S  Q  I  Y  E
CTCTTAAGAGGTTATTTTTCTTGATCGATGCCCGGTGGTGACCAGCACCATTCCTTTATCGGATTCACTCACACTCCTAGCGAATCATGTAGTGCGGTGA  700
                                       3'-UT

GAGTGGGCTCTGGAGGAGACTGTTGTGTAGCCATGGCTTCAGGAGAGAAAACAAAATACAAGGAAAGGCAATATGTAACTATGGGGTTCCCTTTTTTACT  800
                                       3'-UT

ATGCAAAGTTTTTATAACTCCTGATCGGCAAAAACAACAACAACCGCCATACACCAAGAGCAAATGCTTTCTTCTGCGGACTGTGCTTCTGTTTTTTTTT  900
                                       3'-UT

ATGAAGGAGTGACTCGCGCGATGAAAAGTGTGTGCGTGGGAGATGTATTTCCTTTTTTTGTTCATAGTGGCGACAGCTCACTGTTGACGATGACAAAAAA  1000
                                       3'-UT

AAAAAAAAAAAAACTCGAG  1019
|Poly A tail/ Xhoi>
```

Fig. 21

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
       (A) LENGTH: 3134 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 421..2058

(xi) SEQUENCE DESCRIPTION: SKEQ ID NO:1:

```
CAAGTGTCGA AGGACAGTGT TCNCCGTGTG AGATCGCCGG CTGTGCGTGT GAAGGCGGTG      60

CCATCGGANA AACAACACCG GTGGANCCGC AGGAAACCAT CTTTCTCCGC AGGTCTCTTT     120

TTGTTGTCGA TTGAGAGTGC NCCAAACCCT GCTGGTGCCC TTCTCACATA TCATGTTTTT     180

CGTTGTGCGC TCGCTTTGCC TTTCCTCTCC TTTCCCTCTC TTCCGTGGTG CCGTGTATAC     240

TTCTGGCACC CGCTACGTCA CTTCGCTGGT TTGAACAGAA CCACTGTGAA CACCCACGGG     300

CGATCGCACA CATACACATC CCTCACTCAC ACACACAGCT ACATCTATCC TACATAAAGC     360

TGAAAAAAAA GTCTACGAAC AATTTTGTTT TTACAGTGCG TTGCCGCACA TTTCTCCGTA     420

ATG GAC GCA ACT GAG CTG AAG AAC AAG GGG AAC GAA GAG TTC TCC GCC      468
Met Asp Ala Thr Glu Leu Lys Asn Lys Gly Asn Glu Glu Phe Ser Ala
1               5                  10                  15

GGC CGC TAT GTG GAG GCG GTG AAC TAC TTC TCA AAG GCG ATC CAG TTG      516
Gly Arg Tyr Val Glu Ala Val Asn Tyr Phe Ser Lys Ala Ile Gln Leu
20                  25                  30

GAT GAG CAG AAC AGT GTC CTC TAC AGC AAC CGC TCC GCC TGT TTT GCA      564
Asp Glu Gln Asn Ser Val Leu Tyr Ser Asn Arg Ser Ala Cys Phe Ala
35                  40                  45

GCC ATG CAG AAA TAC AAG GAC GCG CTG GAC GAC GCC GAC AAG TGC ATC      612
Ala Met Gln Lys Tyr Lys Asp Ala Leu Asp Asp Ala Asp Lys Cys Ile
50                  55                  60

TCG ATC AAG CCG AAT TGG GCC AAG GGC TAC GTG CGC CGA GGA GCA GCT      660
Ser Ile Lys Pro Asn Trp Ala Lys Gly Tyr Val Arg Arg Gly Ala Ala
65                  70                  75                  80

CTC CAT GGC ATG CGC CGC TAC GAC GAT GCC ATT GCC GCG TAT GAA AAG      708
Leu His Gly Met Arg Arg Tyr Asp Asp Ala Ile Ala Ala Tyr Glu Lys
85                  90                  95

GGG CTC AAG GTG GAC CCT TCC AAC AGC GGC TGC GCG CAG GGC GTG AAG      756
Gly Leu Lys Val Asp Pro Ser Asn Ser Gly Cys Ala Gln Gly Val Lys
100                 105                 110

GAC GTG CAG GTA GCC AAG GCC CGC GAA GCA CGT GAC CCC ATC GCT CGC      804
Asp Val Gln Val Ala Lys Ala Arg Glu Ala Arg Asp Pro Ile Ala Arg
115                 120                 125

GTC TTC ACC CCG GAG GCG TTC CGC AAG ATC CAA GAG AAT CCC AAG CTG      852
Val Phe Thr Pro Glu Ala Phe Arg Lys Ile Gln Glu Asn Pro Lys Leu
130                 135                 140

TCT CTA CTT ATG CTG CAG CCG GAC TAC GTG AAG ATG GTA GAC ACC GTC      900
Ser Leu Leu Met Leu Gln Pro Asp Tyr Val Lys Met Val Asp Thr Val
145                 150                 155                 160

ATC CGC GAC CCT TCG CAG GGC CGG CTG TAC ATG GAA GAC CAG CGC TTT      948
Ile Arg Asp Pro Ser Gln Gly Arg Leu Tyr Met Glu Asp Gln Arg Phe
```

```
                165                 170                 175
GCC CTG ACG CTC ATG TAC CTG AGC GGA ATG AAG ATT CCC AAC GAT GGT      996
Ala Leu Thr Leu Met Tyr Leu Ser Gly Met Lys Ile Pro Asn Asp Gly
180                 185                 190

GAT GGC GAG GAG GAG GAA CGT CCG TCT GCG AAG GCG GCA GAG ACA GCG     1044
Asp Gly Glu Glu Glu Glu Arg Pro Ser Ala Lys Ala Ala Glu Thr Ala
195                 200                 205

AAG CCA AAA GAG GAG AAG CCT CTC ACC GAC AAC GAG AAG GAG GCC CTG     1092
Lys Pro Lys Glu Glu Lys Pro Leu Thr Asp Asn Glu Lys Glu Ala Leu
210                 215                 220

GCG CTC AAG GAG GAG GGC AAC AAG CTG TAC CTC TCG AAG AAG TTT GAG     1140
Ala Leu Lys Glu Glu Gly Asn Lys Leu Tyr Leu Ser Lys Lys Phe Glu
225                 230                 235                 240

GAG GCG CTG ACC AAG TAC CAA GAG GCG CAG GTG AAA GAC CCC AAC AAC     1188
Glu Ala Leu Thr Lys Tyr Gln Glu Ala Gln Val Lys Asp Pro Asn Asn
245                 250                 255

ACT TTA TAC ATT CTG AAC GTG TCG GCC GTG TAC TTC GAG CAG GGT GAC     1236
Thr Leu Tyr Ile Leu Asn Val Ser Ala Val Tyr Phe Glu Gln Gly Asp
260                 265                 270

TAC GAC AAG TGC ATC GCC GAG TGC GAG CAC GGT ATC GAG CAC GGT CGC     1284
Tyr Asp Lys Cys Ile Ala Glu Cys Glu His Gly Ile Glu His Gly Arg
275                 280                 285

GAG AAC CAC TGC GAC TAC ACA ATC ATT GCG AAG CTC ATG ACC CGG AAC     1332
Glu Asn His Cys Asp Tyr Thr Ile Ile Ala Lys Leu Met Thr Arg Asn
290                 295                 300

GCC TTG TGC CTC CAG AGG CAG AGG AAG TAC GAG GCT GCT ATC GAC CTT     1380
Ala Leu Cys Leu Gln Arg Gln Arg Lys Tyr Glu Ala Ala Ile Asp Leu
305                 310                 315                 320

TAC AAG CGC GCC CTT GTC GAG TGG CGT AAC CCT GAC ACC CTC AAG AAG     1428
Tyr Lys Arg Ala Leu Val Glu Trp Arg Asn Pro Asp Thr Leu Lys Lys
325                 330                 335

CTG ACG GAG TGC GAG AAG GAG CAC CAA AAG GCG GTG GAG GAA GCC TAC     1476
Leu Thr Glu Cys Glu Lys Glu His Gln Lys Ala Val Glu Glu Ala Tyr
340                 345                 350

ATC GAT CCT GAG ATC GCG AAG CAG AAG AAA GAC GAA GGT AAC CAG TAC     1524
Ile Asp Pro Glu Ile Ala Lys Gln Lys Lys Asp Glu Gly Asn Gln Tyr
355                 360                 365

TTC AAG GAG GAT AAG TTC CCC GAG GCC GTG GCA GCG TAC ACG GAG GCC     1572
Phe Lys Glu Asp Lys Phe Pro Glu Ala Val Ala Ala Tyr Thr Glu Ala
370                 375                 380

ATC AAG CGC AAC CCT GCC GAG CAC ACC TCC TAC AGC AAT CGC GCG GCC     1620
Ile Lys Arg Asn Pro Ala Glu His Thr Ser Tyr Ser Asn Arg Ala Ala
385                 390                 395                 400

GCG TAC ATC AAG CTT GGA GCC TTC AAC GAC GCC CTC AAG GAC GCG GAG     1668
Ala Tyr Ile Lys Leu Gly Ala Phe Asn Asp Ala Leu Lys Asp Ala Glu
405                 410                 415

AAG TGC ATT GAG CTG AAG CCC GAC TTT GTT AAG GGC TAC GCG CGC AAG     1716
Lys Cys Ile Glu Leu Lys Pro Asp Phe Val Lys Gly Tyr Ala Arg Lys
420                 425                 430

GGT CAT GCT TAC TTT TGG ACC AAG CAG TAC AAC CGC GCG CTG CAG GCG     1764
Gly His Ala Tyr Phe Trp Thr Lys Gln Tyr Asn Arg Ala Leu Gln Ala
435                 440                 445

TAC GAT GAG GGC CTC AAG GTG GAC CCG AGC AAT GCG GAC TGC AAG GAT     1812
Tyr Asp Glu Gly Leu Lys Val Asp Pro Ser Asn Ala Asp Cys Lys Asp
450                 455                 460

GGG CGG TAT CGC ACA ATC ATG AAG ATT CAG GAG ATG GCA TCT GGC CAA     1860
Gly Arg Tyr Arg Thr Ile Met Lys Ile Gln Glu Met Ala Ser Gly Gln
465                 470                 475                 480

TCC GCG GAT GGC GAC GAG GCG GCG CGC CGG GCC ATG GAC GAT CCT GAA     1908
```

-continued

```
Ser Ala Asp Gly Asp Glu Ala Ala Arg Arg Ala Met Asp Asp Pro Glu
485                 490                 495

ATC GCG GCA ATC ATG CAA GAT AGC TAC ATG CAA CTA GTG TTG AAG GAG      1956
Ile Ala Ala Ile Met Gln Asp Ser Tyr Met Gln Leu Val Leu Lys Glu
500                 505                 510

ATG CAG AAC GAT CCC ACG CGC ATT CAG GAG TAC ATG AAG GAC TCC GGG      2004
Met Gln Asn Asp Pro Thr Arg Ile Gln Glu Tyr Met Lys Asp Ser Gly
515                 520                 525

ATC TCA TCG AAG ATC AAC AAG CTG ATT TCA GCT GGC ATC ATT CGT TTT      2052
Ile Ser Ser Lys Ile Asn Lys Leu Ile Ser Ala Gly Ile Ile Arg Phe
530                 535                 540

GGT CAG TAGACTTCTA CGCTGCCTCA TCTTTTCCGT GTCTTTGCGT CGGCGGGTAT       2108
Gly Gln
545

CGTAAAGCAC AATAAAGCAG CGATTCACAT GCACGAGTAA AGTGCTGCGC CTCTCAAACA    2168

CGACGTCGAG GCTGTGGTGC AGATGCGCGT CCTGCATGAA GGTAGTGAAG AGGAAAGTAA    2228

GGGATGTTGT TTGTGGGCCT TCGTGGCTGC GCACACACCT CTTATCTCCT TCGCTTGGTA    2288

CCTTCTCCCT TTTTCGTCTT CACCCCCCTT TCTCTTCTCA CGCTCTCCCT GGCGCGGTGG    2348

TGCAACGATT TCGTTTTATT TACGTCTGTG TAGCTCCTCT ATTCAACGGT GCGATGACGC    2408

TAACGAAGCT GGCCTGTATT CGGCTAAGGC GAAGGCAAAA GACTAGGAGG GGGGGGGAA     2468

GGAGACGGCG TGACCATCAC TGCGAAGAAA CAAGCCGAAG AAAAGGCCCC GAACGCCTGC    2528

ATTTCCGCGC GCCCTCGCCC GCCTTCCTTC CTTCCTTCGC TCTCTCTCTC TCTCTCTCTC    2588

GCTATCTTCT CAACGGAGAC ATGAAAGGCG TTTGTTAGGA AAAGAGGGGG GGGGGAAGAG    2648

TGGGACGACG CGCTGCGTCT TTTGGGCACT GGTCACGTGC GTCACCCTCT TTTTTTATCT    2708

CTATTGGCAC TGTCTTGTTT CTTTTCCCTT TCCTATCATA CGCGTCTCGC AAACGACTCC    2768

GCGCTGAGCA GCCATGTGCT GCGGCGTGGA GGAAGTACAC AGACATCACG GATGCATATG    2828

TGCGCGTCCG TGTACGCGCT TGTATGGGGC TTCTAACAGC GCCTGTGTGT GTTTGTGTGT    2888

GTGTGTGTGT GTGTGTCTGT GTATTTCGAG CGTCTGTATG CTATTCTATT AAGCACCGAA    2948

GAAGAGACAC ACACGACAGC GAAGGAGATG GTGTCGGCTT TTCGGCTAAT CACTCCCTTC    3008

CATAGCTTCT CTGAAGGAGG CTCTCTTCCA GAGGAATAGA CTGCAGATGG GGTCCACGTT    3068

TATCTGAGGA GTCAACGGAA AAAAAAAAA AAAAAAAAA AAAAAAAAA AAAAAAAAA       3128

CTCGAG                                                               3134
```

(2) INFORMATION FOR SEQ ID NO:2:

(i) SEQUENCE CHARACTERISTICS:
        (A) LENGTH: 546 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ala Thr Glu Leu Lys Asn Lys Gly Asn Glu Glu Phe Ser Ala
1               5                   10                  15

Gly Arg Tyr Val Glu Ala Val Asn Tyr Phe Ser Lys Ala Ile Gln Leu
                20                  25                  30

Asp Glu Gln Asn Ser Val Leu Tyr Ser Asn Arg Ser Ala Cys Phe Ala
            35                  40                  45

Ala Met Gln Lys Tyr Lys Asp Ala Leu Asp Asp Ala Asp Lys Cys Ile
        50                  55                  60
```

-continued

```
Ser Ile Lys Pro Asn Trp Ala Lys Gly Tyr Val Arg Arg Gly Ala Ala
 65                  70                  75                  80

Leu His Gly Met Arg Arg Tyr Asp Asp Ala Ile Ala Ala Tyr Glu Lys
                 85                  90                  95

Gly Leu Lys Val Asp Pro Ser Asn Ser Gly Cys Ala Gln Gly Val Lys
            100                 105                 110

Asp Val Gln Val Ala Lys Ala Arg Glu Ala Arg Asp Pro Ile Ala Arg
        115                 120                 125

Val Phe Thr Pro Glu Ala Phe Arg Lys Ile Gln Glu Asn Pro Lys Leu
    130                 135                 140

Ser Leu Leu Met Leu Gln Pro Asp Tyr Val Lys Met Val Asp Thr Val
145                 150                 155                 160

Ile Arg Asp Pro Ser Gln Gly Arg Leu Tyr Met Glu Asp Gln Arg Phe
                165                 170                 175

Ala Leu Thr Leu Met Tyr Leu Ser Gly Met Lys Ile Pro Asn Asp Gly
            180                 185                 190

Asp Gly Glu Glu Glu Arg Pro Ser Ala Lys Ala Ala Glu Thr Ala
        195                 200                 205

Lys Pro Lys Glu Glu Lys Pro Leu Thr Asp Asn Glu Lys Glu Ala Leu
    210                 215                 220

Ala Leu Lys Glu Glu Gly Asn Lys Leu Tyr Leu Ser Lys Lys Phe Glu
225                 230                 235                 240

Glu Ala Leu Thr Lys Tyr Gln Glu Ala Gln Val Lys Asp Pro Asn Asn
                245                 250                 255

Thr Leu Tyr Ile Leu Asn Val Ser Ala Val Tyr Phe Glu Gln Gly Asp
            260                 265                 270

Tyr Asp Lys Cys Ile Ala Glu Cys Glu His Gly Ile Glu His Gly Arg
        275                 280                 285

Glu Asn His Cys Asp Tyr Thr Ile Ile Ala Lys Leu Met Thr Arg Asn
    290                 295                 300

Ala Leu Cys Leu Gln Arg Gln Arg Lys Tyr Glu Ala Ala Ile Asp Leu
305                 310                 315                 320

Tyr Lys Arg Ala Leu Val Glu Trp Arg Asn Pro Asp Thr Leu Lys Lys
                325                 330                 335

Leu Thr Glu Cys Glu Lys Glu His Gln Lys Ala Val Glu Glu Ala Tyr
            340                 345                 350

Ile Asp Pro Glu Ile Ala Lys Gln Lys Lys Asp Glu Gly Asn Gln Tyr
        355                 360                 365

Phe Lys Glu Asp Lys Phe Pro Glu Ala Val Ala Ala Tyr Thr Glu Ala
    370                 375                 380

Ile Lys Arg Asn Pro Ala Glu His Thr Ser Tyr Ser Asn Arg Ala Ala
385                 390                 395                 400

Ala Tyr Ile Lys Leu Gly Ala Phe Asn Asp Ala Leu Lys Asp Ala Glu
                405                 410                 415

Lys Cys Ile Glu Leu Lys Pro Asp Phe Val Lys Gly Tyr Ala Arg Lys
            420                 425                 430

Gly His Ala Tyr Phe Trp Thr Lys Gln Tyr Asn Arg Ala Leu Gln Ala
        435                 440                 445

Tyr Asp Glu Gly Leu Lys Val Asp Pro Ser Asn Ala Asp Cys Lys Asp
    450                 455                 460

Gly Arg Tyr Arg Thr Ile Met Lys Ile Gln Glu Met Ala Ser Gly Gln
465                 470                 475                 480

Ser Ala Asp Gly Asp Glu Ala Ala Arg Arg Ala Met Asp Asp Pro Glu
```

-continued

```
                            485                 490                      495
Ile Ala Ala Ile Met Gln Asp Ser Tyr Met Gln Leu Val Leu Lys Glu
                500             505             510

Met Gln Asn Asp Pro Thr Arg Ile Gln Glu Tyr Met Lys Asp Ser Gly
            515                 520             525

Ile Ser Ser Lys Ile Asn Lys Leu Ile Ser Ala Gly Ile Ile Arg Phe
        530                 535             540

Gly Gln
545
```

(2) INFORMATION FOR SEQ ID NO:3:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 26..550

(xi) SEQUENCE DESCRIPTION: SEQ ID NO:3:

```
AATTCGGCAC GAGGCATTGT GCATA ATG GTC AAG TCC CAC TAC ATC TGC GCG       52
                            Met Val Lys Ser His Tyr Ile Cys Ala
                                550                     555

GGC CGC CTG GTG CGC ATC CTG CGT GGC CCC CGC CAG GAC CGC GTT GGT      100
Gly Arg Leu Val Arg Ile Leu Arg Gly Pro Arg Gln Asp Arg Val Gly
                560                 565                 570

GTG ATC GTC GAC ATT GTC GAC GCG AAC CGC GTG CTG GTG GAG AAC CCG      148
Val Ile Val Asp Ile Val Asp Ala Asn Arg Val Leu Val Glu Asn Pro
            575                 580                 585

GAG GAC GCG AAG ATG TGG CGC CAC GTG CAG AAC CTG AAG AAC GTG GAG      196
Glu Asp Ala Lys Met Trp Arg His Val Gln Asn Leu Lys Asn Val Glu
        590                 595                 600

CCG CTG AAG TAC TGC GTG AGC GTC AGC CGC AAC TGC AGC GCG AAG GCG      244
Pro Leu Lys Tyr Cys Val Ser Val Ser Arg Asn Cys Ser Ala Lys Ala
    605                 610                 615

CTG AAG GAT GCG CTG GCC TCG TCG AAG GCG CTG GAG AAG TAC GCG AAG      292
Leu Lys Asp Ala Leu Ala Ser Ser Lys Ala Leu Glu Lys Tyr Ala Lys
620                 625                 630                 635

ACG CGC ACT GCT GCG CGC GTG GAG GCG AAG AAG GCG TGC GCC GCG TCG      340
Thr Arg Thr Ala Ala Arg Val Glu Ala Lys Lys Ala Cys Ala Ala Ser
                640                 645                 650

ACG GAC TTC GAG CGC TAC CAG CTG CGC GTT GCG CGC CGT TCT CGC GCG      388
Thr Asp Phe Glu Arg Tyr Gln Leu Arg Val Ala Arg Arg Ser Arg Ala
            655                 660                 665

CAC TGG GCG CGC AAG GTG TTC GAC GAG AAG GAC GCG AAG ACG CCC GTG      436
His Trp Ala Arg Lys Val Phe Asp Glu Lys Asp Ala Lys Thr Pro Val
        670                 675                 680

TCG TGG CAC AAG GTT GCG CTG AAG AAG ATG CAG AAG AAG GCC GCA AAG      484
Ser Trp His Lys Val Ala Leu Lys Lys Met Gln Lys Lys Ala Ala Lys
    685                 690                 695

ATG GAC TCG ACC GAG GGC GCT AAG AGG CGC ATG CAG AAG GCG ATC GCT      532
Met Asp Ser Thr Glu Gly Ala Lys Arg Arg Met Gln Lys Ala Ile Ala
700                 705                 710                 715

GCC CGC AAG GCG AAA AAG TAAGGCCATA CCCTCACTTC GCTTGTTTCG              580
Ala Arg Lys Ala Lys Lys
                720

TGATTTTTCG TGGGAGTCGG TGGCCCTACC AGCGGTCTTT CATTGGCTTA TTTCTATCCG      640
```

```
GTCTGAAAGA GGTACAAAAA AAAAAAAAAA AAAAAA                                        676
```

(2) INFORMATION FOR SEQ ID NO:4:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Lys Ser His Tyr Ile Cys Ala Gly Arg Leu Val Arg Ile Leu
 1               5                  10                  15

Arg Gly Pro Arg Gln Asp Arg Val Gly Val Ile Val Asp Ile Val Asp
            20                  25                  30

Ala Asn Arg Val Leu Val Glu Asn Pro Glu Asp Ala Lys Met Trp Arg
        35                  40                  45

His Val Gln Asn Leu Lys Asn Val Glu Pro Leu Lys Tyr Cys Val Ser
    50                  55                  60

Val Ser Arg Asn Cys Ser Ala Lys Ala Leu Lys Asp Ala Leu Ala Ser
65                  70                  75                  80

Ser Lys Ala Leu Glu Lys Tyr Ala Lys Thr Arg Thr Ala Ala Arg Val
                85                  90                  95

Glu Ala Lys Lys Ala Cys Ala Ala Ser Thr Asp Phe Glu Arg Tyr Gln
            100                 105                 110

Leu Arg Val Ala Arg Arg Ser Arg Ala His Trp Ala Arg Lys Val Phe
        115                 120                 125

Asp Glu Lys Asp Ala Lys Thr Pro Val Ser Trp His Lys Val Ala Leu
    130                 135                 140

Lys Lys Met Gln Lys Lys Ala Ala Lys Met Asp Ser Thr Glu Gly Ala
145                 150                 155                 160

Lys Arg Arg Met Gln Lys Ala Ile Ala Ala Arg Lys Ala Lys Lys
                165                 170                 175
```

(2) INFORMATION FOR SEQ ID NO:5:

(i) SEQUENCE CHARACTERISTICS:
        (A) LENGTH: 2040 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 62..2029

(xi) SEQUENCE DESCRIPTION: SEQ ID NO:5:

```
CGCGGTGGCG GCCGCTCTAG AACTAGTGGA TCCCCCGGGC TGCAGGAATT CGGCACGAGA     60

G AGC CTG ACG GAC CCG GCG GTG CTG GGC GAG GAG ACT CAC CTG CGC        106
  Ser Leu Thr Asp Pro Ala Val Leu Gly Glu Glu Thr His Leu Arg
              180                 185                 190

GTC CGC GTG GTG CCG GAC AAG GCG AAC AAG ACG CTG ACG GTG GAG GAT     154
Val Arg Val Val Pro Asp Lys Ala Asn Lys Thr Leu Thr Val Glu Asp
            195                 200                 205

AAC GGC ATC GGC ATG ACC AAG GCG GAC CTC GTG AAC AAT CTG GGC ACG     202
Asn Gly Ile Gly Met Thr Lys Ala Asp Leu Val Asn Asn Leu Gly Thr
        210                 215                 220

ATC GCG CGC TCC GGC ACG AAG GCT TTC ATG GAG GCA CTG GAG GCC GGC     250
Ile Ala Arg Ser Gly Thr Lys Ala Phe Met Glu Ala Leu Glu Ala Gly
    225                 230                 235
```

```
GGC GAC ATG AGC ATG ATC GGC CAG TTC GGT GTC GGC TTC TAC TCC GCG      298
Gly Asp Met Ser Met Ile Gly Gln Phe Gly Val Gly Phe Tyr Ser Ala
    240                 245                 250

TAC CTT GTG GCG GAC CGC GTG ACG GTG GTG TCG AAG AAC AAC TCG GAC      346
Tyr Leu Val Ala Asp Arg Val Thr Val Val Ser Lys Asn Asn Ser Asp
255                 260                 265                 270

GAG GCG TAC TGG GAA TCG TCT GCG GGG GGC ACG TTC ACC ATC ACG AGC      394
Glu Ala Tyr Trp Glu Ser Ser Ala Gly Gly Thr Phe Thr Ile Thr Ser
                275                 280                 285

GTG CAG GAG TCG GAC ATG AAG CGC GGC ACG AGT ACA ACG CTG CAC CTA      442
Val Gln Glu Ser Asp Met Lys Arg Gly Thr Ser Thr Thr Leu His Leu
                    290                 295                 300

AAG GAG GAC CAG CAG GAG TAC CTG GAG GAG CGC CGG GTG AAG GAG CTG      490
Lys Glu Asp Gln Gln Glu Tyr Leu Glu Glu Arg Arg Val Lys Glu Leu
                305                 310                 315

ATC AAG AAG CAC TCC GAG TTC ATC GGC TAC GAC ATC GAG CTG ATG GTG      538
Ile Lys Lys His Ser Glu Phe Ile Gly Tyr Asp Ile Glu Leu Met Val
            320                 325                 330

GAG AAG ACG GCG GAG AAG GAG GTG ACG GAC GAG GAC GAG GAG GAG GAC      586
Glu Lys Thr Ala Glu Lys Glu Val Thr Asp Glu Asp Glu Glu Glu Asp
335                 340                 345                 350

GAG TCG AAG AAG AAG TCC TGC GGG GAC GAG GGC GAG CCG AAG GTG GAG      634
Glu Ser Lys Lys Lys Ser Cys Gly Asp Glu Gly Glu Pro Lys Val Glu
                355                 360                 365

GAG GTG ACG GAG GGC GGC GAG GAC AAG AAG AAG AAG ACG AAG AAG GTG      682
Glu Val Thr Glu Gly Gly Glu Asp Lys Lys Lys Thr Lys Lys Val
                370                 375                 380

AAG GAG GTG AAG AAG ACG TAC GAG GTC AAG AAC AAG CAC AAG CCG CTC      730
Lys Glu Val Lys Lys Thr Tyr Glu Val Lys Asn Lys His Lys Pro Leu
                385                 390                 395

TGG ACG CGC GAC ACG AAG GAC GTG ACG AAG GAG GAG TAC GCG GCC TTC      778
Trp Thr Arg Asp Thr Lys Asp Val Thr Lys Glu Glu Tyr Ala Ala Phe
400                 405                 410

TAC AAG GCC ATC TCC AAC GAC TGG GAG GAC ACG GCG GCG ACG AAG CAC      826
Tyr Lys Ala Ile Ser Asn Asp Trp Glu Asp Thr Ala Ala Thr Lys His
415                 420                 425                 430

TTC TCG GTG GAG GGC CAG CTG GAG TTC CGC GCG ATC GCG TTC GTG CCG      874
Phe Ser Val Glu Gly Gln Leu Glu Phe Arg Ala Ile Ala Phe Val Pro
                435                 440                 445

AAG CGC GCG CCG TTC GAC ATG TTC GAG CCG AAC AAG AAG CGC AAC AAC      922
Lys Arg Ala Pro Phe Asp Met Phe Glu Pro Asn Lys Lys Arg Asn Asn
                450                 455                 460

ATC AAG CTG TAC GTG CGC CGC GTG TTC ATC ATG GAC AAC TGC GAG GAC      970
Ile Lys Leu Tyr Val Arg Arg Val Phe Ile Met Asp Asn Cys Glu Asp
                465                 470                 475

CTG TGC CCG GAC TGG CTC GGC TTC GTG AAG GGC GTC GTG GAC AGC GAG      1018
Leu Cys Pro Asp Trp Leu Gly Phe Val Lys Gly Val Val Asp Ser Glu
            480                 485                 490

GAC CTG CCG CTG AAC ATC TCG CGC GAG AAC CTG CAG CAG AAC AAG ATC      1066
Asp Leu Pro Leu Asn Ile Ser Arg Glu Asn Leu Gln Gln Asn Lys Ile
495                 500                 505                 510

CTG AAG GTG ATC CGC AAG AAC ATC GTG AAG AAG TGC CTG GAG CTG TTC      1114
Leu Lys Val Ile Arg Lys Asn Ile Val Lys Lys Cys Leu Glu Leu Phe
                515                 520                 525

GAA GAG ATA GCG GAG AAC AAG GAG GAC TAC AAG CAG TTC TAC GAG CAG      1162
Glu Glu Ile Ala Glu Asn Lys Glu Asp Tyr Lys Gln Phe Tyr Glu Gln
                530                 535                 540

TTC GGC AAG AAC ATC AAG CTG GGC ATC CAC GAG GAC ACG GCG AAC CGC      1210
Phe Gly Lys Asn Ile Lys Leu Gly Ile His Glu Asp Thr Ala Asn Arg
```

-continued

```
               545                 550                 555
AAG AAG CTG ATG GAG TTG CTG CGC TTC TAC AGC ACC GAG TCG GGG GAG      1258
Lys Lys Leu Met Glu Leu Leu Arg Phe Tyr Ser Thr Glu Ser Gly Glu
    560                 565                 570

GAG ATG ACG ACA CTG AAG GAC TAC GTG ACG CGC ATG AAG CCG GAG CAG      1306
Glu Met Thr Thr Leu Lys Asp Tyr Val Thr Arg Met Lys Pro Glu Gln
575                 580                 585                 590

AAG TCG ATC TAC TAC ATC ACT GGC GAC AGC AAG AAG AAG CTG GAG TCG      1354
Lys Ser Ile Tyr Tyr Ile Thr Gly Asp Ser Lys Lys Lys Leu Glu Ser
                595                 600                 605

TCG CCG TTC ATC GAG AAG GCG AGA CGC TGC GGG CTC GAG GTG CTG TTC      1402
Ser Pro Phe Ile Glu Lys Ala Arg Arg Cys Gly Leu Glu Val Leu Phe
            610                 615                 620

ATG ACG GAG CCG ATC GAC GAG TAC GTG ATG CAG CAG GTG AAG GAC TTC      1450
Met Thr Glu Pro Ile Asp Glu Tyr Val Met Gln Gln Val Lys Asp Phe
        625                 630                 635

GAG GAC AAG AAG TTC GCG TGC CTG ACG AAG GAA GGC GTG CAC TTC GAG      1498
Glu Asp Lys Lys Phe Ala Cys Leu Thr Lys Glu Gly Val His Phe Glu
    640                 645                 650

GAG TCC GAG GAG GAG AAG AAG CAG CGC GAG GAG AAG AAG GCG GCG TGC      1546
Glu Ser Glu Glu Glu Lys Lys Gln Arg Glu Glu Lys Lys Ala Ala Cys
655                 660                 665                 670

GAG AAG CTG TGC AAG ACG ATG AAG GAG GTG CTG GGC GAC AAG GTG GAG      1594
Glu Lys Leu Cys Lys Thr Met Lys Glu Val Leu Gly Asp Lys Val Glu
                675                 680                 685

AAG GTG ACC GTG TCG GAG CGC CTG TTG ACG TCG CCG TGC ATC CTG GTG      1642
Lys Val Thr Val Ser Glu Arg Leu Leu Thr Ser Pro Cys Ile Leu Val
            690                 695                 700

ACG TCG GAG TTT GGG TGG TCG GCG CAC ATG GAA CAG ATC ATG CGC AAC      1690
Thr Ser Glu Phe Gly Trp Ser Ala His Met Glu Gln Ile Met Arg Asn
        705                 710                 715

CAG GCG CTG CGC GAC TCC AGC ATG GCG CAG TAC ATG GTG TCC AAG AAG      1738
Gln Ala Leu Arg Asp Ser Ser Met Ala Gln Tyr Met Val Ser Lys Lys
    720                 725                 730

ACG ATG GAG GTG AAC CCC GAC CAC CCC ATC ATC AAG GAG CTG CGC CGC      1786
Thr Met Glu Val Asn Pro Asp His Pro Ile Ile Lys Glu Leu Arg Arg
735                 740                 745                 750

CGC GTG GAG GCC GAC GAG AAC GAC AAG GCC GTG AAG GAC CTC GTC TTC      1834
Arg Val Glu Ala Asp Glu Asn Asp Lys Ala Val Lys Asp Leu Val Phe
                755                 760                 765

CTG CTC TTC GAC ACG TCG CTG CTC ACG TCC GGC TTC CAG CTG GAT GAC      1882
Leu Leu Phe Asp Thr Ser Leu Leu Thr Ser Gly Phe Gln Leu Asp Asp
            770                 775                 780

CCC ACC GGC TAC GCC GAG CGC ATC AAC CGC ATG ATC AAG CTC GGC CTG      1930
Pro Thr Gly Tyr Ala Glu Arg Ile Asn Arg Met Ile Lys Leu Gly Leu
        785                 790                 795

TCG CTC GAC GAG GAG GAG GAG GTC GCC GAG GCG CCG CCG GCC GAG           1978
Ser Leu Asp Glu Glu Glu Glu Val Ala Glu Ala Pro Pro Ala Glu
    800                 805                 810

GCA GCC CCC GCG GAG GTC ACC GCC GGC ACC TCC AGC ATG GAG CAG GTG      2026
Ala Ala Pro Ala Glu Val Thr Ala Gly Thr Ser Ser Met Glu Gln Val
815                 820                 825                 830

GAC TGAGCCGGTA A                                                      2040
Asp
```

(2) INFORMATION FOR SEQ ID NO:6:

(i) SEQUENCE CHARACTERISTICS:
        (A) LENGTH: 656 amino acids
        (B) TYPE: amino acid (D) TOPOLOGY: linear (ii) MOLECULE TYPE: protein (xi) SEQUENCE DESCRIPTION: SEQ ID NO:6:

Ser Leu Thr Asp Pro Ala Val Leu Gly Glu Glu Thr His Leu Arg Val
 1               5                  10                  15

Arg Val Val Pro Asp Lys Ala Asn Lys Thr Leu Thr Val Glu Asp Asn
                20                  25                  30

Gly Ile Gly Met Thr Lys Ala Asp Leu Val Asn Asn Leu Gly Thr Ile
            35                  40                  45

Ala Arg Ser Gly Thr Lys Ala Phe Met Glu Ala Leu Glu Ala Gly Gly
        50                  55                  60

Asp Met Ser Met Ile Gly Gln Phe Gly Val Gly Phe Tyr Ser Ala Tyr
 65                  70                  75                  80

Leu Val Ala Asp Arg Val Thr Val Val Ser Lys Asn Asn Ser Asp Glu
                85                  90                  95

Ala Tyr Trp Glu Ser Ser Ala Gly Gly Thr Phe Thr Ile Thr Ser Val
            100                 105                 110

Gln Glu Ser Asp Met Lys Arg Gly Thr Ser Thr Thr Leu His Leu Lys
        115                 120                 125

Glu Asp Gln Gln Glu Tyr Leu Glu Glu Arg Arg Val Lys Glu Leu Ile
130                 135                 140

Lys Lys His Ser Glu Phe Ile Gly Tyr Asp Ile Glu Leu Met Val Glu
145                 150                 155                 160

Lys Thr Ala Glu Lys Glu Val Thr Asp Glu Asp Glu Glu Glu Asp Glu
                165                 170                 175

Ser Lys Lys Lys Ser Cys Gly Asp Gly Glu Pro Lys Val Glu Glu
            180                 185                 190

Val Thr Glu Gly Gly Glu Asp Lys Lys Lys Thr Lys Lys Val Lys
        195                 200                 205

Glu Val Lys Lys Thr Tyr Glu Val Lys Asn Lys His Lys Pro Leu Trp
210                 215                 220

Thr Arg Asp Thr Lys Asp Val Thr Lys Glu Glu Tyr Ala Ala Phe Tyr
225                 230                 235                 240

Lys Ala Ile Ser Asn Asp Trp Glu Asp Thr Ala Thr Lys His Phe
                245                 250                 255

Ser Val Glu Gly Gln Leu Glu Phe Arg Ala Ile Ala Phe Val Pro Lys
            260                 265                 270

Arg Ala Pro Phe Asp Met Phe Glu Pro Asn Lys Lys Arg Asn Asn Ile
        275                 280                 285

Lys Leu Tyr Val Arg Arg Val Phe Ile Met Asp Asn Cys Glu Asp Leu
290                 295                 300

Cys Pro Asp Trp Leu Gly Phe Val Lys Gly Val Val Asp Ser Glu Asp
305                 310                 315                 320

Leu Pro Leu Asn Ile Ser Arg Glu Asn Leu Gln Gln Asn Lys Ile Leu
                325                 330                 335

Lys Val Ile Arg Lys Asn Ile Val Lys Lys Cys Leu Glu Leu Phe Glu
            340                 345                 350

Glu Ile Ala Glu Asn Lys Glu Asp Tyr Lys Gln Phe Tyr Glu Gln Phe
        355                 360                 365

Gly Lys Asn Ile Lys Leu Gly Ile His Glu Asp Thr Ala Asn Arg Lys
370                 375                 380

Lys Leu Met Glu Leu Leu Arg Phe Tyr Ser Thr Glu Ser Gly Glu Glu

-continued

```
           385                 390                 395                 400
Met Thr Thr Leu Lys Asp Tyr Val Thr Arg Met Lys Pro Glu Gln Lys
                405                 410                 415

Ser Ile Tyr Tyr Ile Thr Gly Asp Ser Lys Lys Leu Glu Ser Ser
            420                 425                 430

Pro Phe Ile Glu Lys Ala Arg Arg Cys Gly Leu Glu Val Leu Phe Met
            435                 440                 445

Thr Glu Pro Ile Asp Glu Tyr Val Met Gln Val Lys Asp Phe Glu
    450                 455                 460

Asp Lys Lys Phe Ala Cys Leu Thr Lys Glu Gly Val His Phe Glu Glu
465                 470                 475                 480

Ser Glu Glu Glu Lys Lys Gln Arg Glu Lys Lys Ala Ala Cys Glu
                485                 490                 495

Lys Leu Cys Lys Thr Met Lys Glu Val Leu Gly Asp Lys Val Glu Lys
                500                 505                 510

Val Thr Val Ser Glu Arg Leu Leu Thr Ser Pro Cys Ile Leu Val Thr
            515                 520                 525

Ser Glu Phe Gly Trp Ser Ala His Met Glu Gln Ile Met Arg Asn Gln
    530                 535                 540

Ala Leu Arg Asp Ser Ser Met Ala Gln Tyr Met Val Ser Lys Lys Thr
545                 550                 555                 560

Met Glu Val Asn Pro Asp His Pro Ile Ile Lys Glu Leu Arg Arg Arg
                565                 570                 575

Val Glu Ala Asp Glu Asn Asp Lys Ala Val Lys Asp Leu Val Phe Leu
                580                 585                 590

Leu Phe Asp Thr Ser Leu Leu Thr Ser Gly Phe Gln Leu Asp Asp Pro
            595                 600                 605

Thr Gly Tyr Ala Glu Arg Ile Asn Arg Met Ile Lys Leu Gly Leu Ser
    610                 615                 620

Leu Asp Glu Glu Glu Glu Val Ala Glu Ala Pro Pro Ala Glu Ala
625                 630                 635                 640

Ala Pro Ala Glu Val Thr Ala Gly Thr Ser Ser Met Glu Gln Val Asp
                645                 650                 655

(2) INFORMATION FOR SEQ ID NO:7:

(i) SEQUENCE CHARACTERISTICS:
        (A) LENGTH: 1771 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1698

(xi) SEQUENCE DESCRIPTION: SEQ ID NO:7:

CAG GCC CGC GTC CAG GCC CTC GAG GAG GCA GCG CGT CTC CGC GCG GAG          48
Gln Ala Arg Val Gln Ala Leu Glu Glu Ala Ala Arg Leu Arg Ala Glu
  1               5                  10                  15

CTG GAG GCG GCC GAG GAG GCG GCC CGC CTG GAT GTC ATG CAT GCG GCC          96
Leu Glu Ala Ala Glu Glu Ala Ala Arg Leu Asp Val Met His Ala Ala
             20                  25                  30

GAG CAG GCC CGT GTC CAG GCC CTC GAG GAG GCA GCG CGT CTC CGC GCG         144
Glu Gln Ala Arg Val Gln Ala Leu Glu Glu Ala Ala Arg Leu Arg Ala
         35                  40                  45

GAG CTG GAG GAG GCC GAG GAG GCG GCC CGC CTG GAT GTC ATG CAT GCG         192
Glu Leu Glu Glu Ala Glu Glu Ala Ala Arg Leu Asp Val Met His Ala
```

-continued

```
              50                      55                      60
GCC GAG CAG GCC CGC GTC CAG GCC CTC GAG GAG GCA GCG CGT CTC CGC       240
Ala Glu Gln Ala Arg Val Gln Ala Leu Glu Glu Ala Ala Arg Leu Arg
 65                      70                      75                      80

GCG GAG CTG GAG GCT GCC GAG GAG GCG GCG CGC CTG GAG GCC ATG CAC       288
Ala Glu Leu Glu Ala Ala Glu Glu Ala Ala Arg Leu Glu Ala Met His
                 85                      90                      95

GAG GCC GAG CAG GCC CGC TCC CAG GCC CTC GAG GAG GCA GCG CGT CTC       336
Glu Ala Glu Gln Ala Arg Ser Gln Ala Leu Glu Glu Ala Ala Arg Leu
                        100                     105                     110

CGC GCG GAG CTG GAG GAA GCC GAG GAG GCG GCC CGC CTG GAT GTC ATG       384
Arg Ala Glu Leu Glu Glu Ala Glu Glu Ala Ala Arg Leu Asp Val Met
                115                     120                     125

CAT GCG GCC GAG CAG GCC CGC GTC CAG GCC CTC GAG GAG GCA GCG CGT       432
His Ala Ala Glu Gln Ala Arg Val Gln Ala Leu Glu Glu Ala Ala Arg
 130                     135                     140

CTC CGC GCG GAG CTG GAG GAG GCC GAG GAG GCG GCC CGC CTG GAG GCC       480
Leu Arg Ala Glu Leu Glu Glu Ala Glu Glu Ala Ala Arg Leu Glu Ala
145                     150                     155                     160

ATG CAC GAG GCC GAG CAG GCC CGC TCC CAG GCC CTC GAG GAG GCA GCG       528
Met His Glu Ala Glu Gln Ala Arg Ser Gln Ala Leu Glu Glu Ala Ala
                        165                     170                     175

CGT CTC CGC GCG GAG CTG GAG GCG GCC GAG GAG GCG GCC CGC CTG GAT       576
Arg Leu Arg Ala Glu Leu Glu Ala Ala Glu Glu Ala Ala Arg Leu Asp
                180                     185                     190

GTC ATG CAC GAG GCC GAG CAG GCC CGT GTC CAG GCC CTC GAG GAG GCG       624
Val Met His Glu Ala Glu Gln Ala Arg Val Gln Ala Leu Glu Glu Ala
        195                     200                     205

GCG CGC CTG GAT GTC ATG CAC GAG GCC GAG CAG GCC CGC GTC CAG GCC       672
Ala Arg Leu Asp Val Met His Glu Ala Glu Gln Ala Arg Val Gln Ala
 210                     215                     220

CTC GAG GAG GCA GCG CGT CTC CGC GCG GAG CTG GAG GCG GCC GAG GAG       720
Leu Glu Glu Ala Ala Arg Leu Arg Ala Glu Leu Glu Ala Ala Glu Glu
225                     230                     235                     240

GCG GCC CGC CTG GAT GTC ATG CAC GAG GCC GAG CAG GCC CGC GTC CAG       768
Ala Ala Arg Leu Asp Val Met His Glu Ala Glu Gln Ala Arg Val Gln
                        245                     250                     255

GCC CTC GAG GAG GCA GCG CGT CTC CGC GCG GAG CTG GAG GCG GCC GAG       816
Ala Leu Glu Glu Ala Ala Arg Leu Arg Ala Glu Leu Glu Ala Ala Glu
                260                     265                     270

GAG GCG GCC CGC CTG GAT GTC ATG CAC GAG GGC GAG CAG GCC CGT GTC       864
Glu Ala Ala Arg Leu Asp Val Met His Glu Gly Glu Gln Ala Arg Val
        275                     280                     285

CAG GCC CTC GAG GAG GCG GCC CGC CTG GAG GCC ATG CAC GAG GCC GAG       912
Gln Ala Leu Glu Glu Ala Ala Arg Leu Glu Ala Met His Glu Ala Glu
 290                     295                     300

CAG GCC CGC TCC CAG GCC CTC GAG GAG GCA GCG CGT CTC TGC GCG GAG       960
Gln Ala Arg Ser Gln Ala Leu Glu Glu Ala Ala Arg Leu Cys Ala Glu
305                     310                     315                     320

CTG GAG GCT GAG GAG GAG GAA AAA GAT GAG CGG CCG GCG ACG TCG AGC      1008
Leu Glu Ala Glu Glu Glu Glu Lys Asp Glu Arg Pro Ala Thr Ser Ser
                        325                     330                     335

TAC AGC GAG GAG TGC AAA GGG CGA CTG CTA TCG AGG GCG CGG CCG GAT      1056
Tyr Ser Glu Glu Cys Lys Gly Arg Leu Leu Ser Arg Ala Arg Pro Asp
                340                     345                     350

CCG CGG AGG CCG CTG CCG CGG CCG TTC ATT GGG ATG TCA CTG TTG GAG      1104
Pro Arg Arg Pro Leu Pro Arg Pro Phe Ile Gly Met Ser Leu Leu Glu
        355                     360                     365

GAT GTG GAG AAG AGT ATT CTC ATT GTG GAC GGG CTC TAC AGG GAT GGG      1152
```

```
Asp Val Glu Lys Ser Ile Leu Ile Val Asp Gly Leu Tyr Arg Asp Gly
        370                 375                 380

CCG GCG TAC CAG ACG GGC ATC CGC CTC GGG GAT GTC CTC TTG CGT ATC         1200
Pro Ala Tyr Gln Thr Gly Ile Arg Leu Gly Asp Val Leu Leu Arg Ile
385                 390                 395                 400

GCG GGG GTT TAC GTG GAT TCA ATA GCG AAG GCG AGG CAG GTG GTC GAT         1248
Ala Gly Val Tyr Val Asp Ser Ile Ala Lys Ala Arg Gln Val Val Asp
                405                 410                 415

GCG CGT TGC CGC TGC GGC TGC GTC GTT CCC GTG ACG CTG GCG ACG AAG         1296
Ala Arg Cys Arg Cys Gly Cys Val Val Pro Val Thr Leu Ala Thr Lys
            420                 425                 430

ATG AAC CAG CAG TAC AGC GTG GCT CTG TAT ATC ATG ACG GTG GAT CCG         1344
Met Asn Gln Gln Tyr Ser Val Ala Leu Tyr Ile Met Thr Val Asp Pro
        435                 440                 445

CAG CAC AAC GAC AAG CCC TTT TTT TTT GAT GTG CAC ATC CAC CAC CGC         1392
Gln His Asn Asp Lys Pro Phe Phe Phe Asp Val His Ile His His Arg
450                 455                 460

ATC GAG AGC TCG CAC ATG GGG AAG AAG GCG CAG TGG ATG GAA GTT CTT         1440
Ile Glu Ser Ser His Met Gly Lys Lys Ala Gln Trp Met Glu Val Leu
465                 470                 475                 480

GAG AGC CCA TCC GTA TCT TCG GCT GCC ACC ACC CCT CTC GTG CCG CTC         1488
Glu Ser Pro Ser Val Ser Ser Ala Ala Thr Thr Pro Leu Val Pro Leu
                485                 490                 495

TTG CGT GAG CCG ACG CCG CGT AGG GGC TCA GAG CTG CAG TCA AGT GCT         1536
Leu Arg Glu Pro Thr Pro Arg Arg Gly Ser Glu Leu Gln Ser Ser Ala
            500                 505                 510

CGT TCC GCC TTC GTT GCC ACG TCT TAC TTC TCG AGC GCG CGC AGG TCG         1584
Arg Ser Ala Phe Val Ala Thr Ser Tyr Phe Ser Ser Ala Arg Arg Ser
        515                 520                 525

GTC AGC TCA GAA AGT GAG CGA CCG CGC GGG TCC TCT AGC GTG GCT ATG         1632
Val Ser Ser Glu Ser Glu Arg Pro Arg Gly Ser Ser Ser Val Ala Met
530                 535                 540

GCG GAG GAG GCG ATC GCG CTG GCG CCG CAA GGG TAT ACC CCA CCC AAC         1680
Ala Glu Glu Ala Ile Ala Leu Ala Pro Gln Gly Tyr Thr Pro Pro Asn
545                 550                 555                 560

CAA GTG CGC GGC CGT AGT TGACGTCTCT GTGTGAGTGT GTGTCGCTCC                1728
Gln Val Arg Gly Arg Ser
            565

GTCTCCTTCC TTTTTCGTCA TGTGTTTTAT TCATTTCTTT TTC                         1771

(2) INFORMATION FOR SEQ ID NO:8:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO:8:

Gln Ala Arg Val Gln Ala Leu Glu Glu Ala Ala Arg Leu Arg Ala Glu
1               5                   10                  15

Leu Glu Ala Ala Glu Glu Ala Ala Arg Leu Asp Val Met His Ala Ala
                20                  25                  30

Glu Gln Ala Arg Val Gln Ala Leu Glu Glu Ala Ala Arg Leu Arg Ala
            35                  40                  45

Glu Leu Glu Glu Ala Glu Glu Ala Ala Arg Leu Asp Val Met His Ala
        50                  55                  60

Ala Glu Gln Ala Arg Val Gln Ala Leu Glu Glu Ala Ala Arg Leu Arg
65                  70                  75                  80
```

-continued

```
Ala Glu Leu Glu Ala Glu Glu Ala Ala Arg Leu Glu Ala Met His
                 85                  90                  95
Glu Ala Glu Gln Ala Arg Ser Gln Ala Leu Glu Glu Ala Ala Arg Leu
            100                 105                 110
Arg Ala Glu Leu Glu Glu Ala Glu Ala Ala Arg Leu Asp Val Met
            115                 120                 125
His Ala Ala Glu Gln Ala Arg Val Gln Ala Leu Glu Glu Ala Ala Arg
            130                 135                 140
Leu Arg Ala Glu Leu Glu Glu Ala Glu Ala Ala Arg Leu Glu Ala
145                 150                 155                 160
Met His Glu Ala Glu Gln Ala Arg Ser Gln Ala Leu Glu Glu Ala Ala
                165                 170                 175
Arg Leu Arg Ala Glu Leu Glu Ala Ala Glu Ala Ala Arg Leu Asp
            180                 185                 190
Val Met His Glu Ala Glu Gln Ala Arg Val Gln Ala Leu Glu Glu Ala
            195                 200                 205
Ala Arg Leu Asp Val Met His Glu Ala Glu Gln Ala Arg Val Gln Ala
            210                 215                 220
Leu Glu Glu Ala Ala Arg Leu Arg Ala Glu Leu Glu Ala Ala Glu Glu
225                 230                 235                 240
Ala Ala Arg Leu Asp Val Met His Glu Ala Glu Gln Ala Arg Val Gln
                245                 250                 255
Ala Leu Glu Glu Ala Ala Arg Leu Arg Ala Glu Leu Glu Ala Ala Glu
            260                 265                 270
Glu Ala Ala Arg Leu Asp Val Met His Glu Gly Glu Gln Ala Arg Val
            275                 280                 285
Gln Ala Leu Glu Glu Ala Ala Arg Leu Glu Ala Met His Glu Ala Glu
            290                 295                 300
Gln Ala Arg Ser Gln Ala Leu Glu Glu Ala Ala Arg Leu Cys Ala Glu
305                 310                 315                 320
Leu Glu Ala Glu Glu Glu Lys Asp Glu Arg Pro Ala Thr Ser Ser
                325                 330                 335
Tyr Ser Glu Glu Cys Lys Gly Arg Leu Leu Ser Arg Ala Arg Pro Asp
                340                 345                 350
Pro Arg Arg Pro Leu Pro Arg Pro Phe Ile Gly Met Ser Leu Leu Glu
            355                 360                 365
Asp Val Glu Lys Ser Ile Leu Ile Val Asp Gly Leu Tyr Arg Asp Gly
            370                 375                 380
Pro Ala Tyr Gln Thr Gly Ile Arg Leu Gly Asp Val Leu Leu Arg Ile
385                 390                 395                 400
Ala Gly Val Tyr Val Asp Ser Ile Ala Lys Ala Arg Gln Val Val Asp
                405                 410                 415
Ala Arg Cys Arg Cys Gly Cys Val Val Pro Val Thr Leu Ala Thr Lys
            420                 425                 430
Met Asn Gln Gln Tyr Ser Val Ala Leu Tyr Ile Met Thr Val Asp Pro
            435                 440                 445
Gln His Asn Asp Lys Pro Phe Phe Asp Val His Ile His His Arg
            450                 455                 460
Ile Glu Ser Ser His Met Gly Lys Lys Ala Gln Trp Met Glu Val Leu
465                 470                 475                 480
Glu Ser Pro Ser Val Ser Ala Ala Thr Thr Pro Leu Val Pro Leu
                485                 490                 495
```

```
Leu Arg Glu Pro Thr Pro Arg Arg Gly Ser Glu Leu Gln Ser Ser Ala
            500                 505                 510

Arg Ser Ala Phe Val Ala Thr Ser Tyr Phe Ser Ser Ala Arg Arg Ser
            515                 520                 525

Val Ser Ser Glu Ser Glu Arg Pro Arg Gly Ser Ser Ser Val Ala Met
            530                 535                 540

Ala Glu Glu Ala Ile Ala Leu Ala Pro Gln Gly Tyr Thr Pro Pro Asn
545                 550                 555                 560

Gln Val Arg Gly Arg Ser
                565

(2) INFORMATION FOR SEQ ID NO:9:

(i) SEQUENCE CHARACTERISTICS:
        (A) LENGTH: 1618 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..1323

(xi) SEQUENCE DESCRIPTION: SEQ ID NO:9:

CCACTCTCTC GGTCGTCTGT CTCCCACGCG CGCACGCAGT TGATTTCCGC CTTCTTAAAC        60

GCTCTCTTTT TTTTTATTTT TCACCTGACC AACCGCACCA CGTCGGCCTC CATC ATG         117
                                                            Met
                                                              1

TCG CAG CAA GAC CGA GTT GCC CCA CAG GAC CAG GAC TCG TTC CTC GAC        165
Ser Gln Gln Asp Arg Val Ala Pro Gln Asp Gln Asp Ser Phe Leu Asp
          5                  10                  15

GAC CAG CCC GGC GTC CGC CCG ATC CCG TCC TTC GAT GAC ATG CCG TTG        213
Asp Gln Pro Gly Val Arg Pro Ile Pro Ser Phe Asp Asp Met Pro Leu
      20                  25                  30

CAC CAG AAC CTT CTG CGC GGC ATC TAC TCG TAC GGC TTC GAG AAA CCG        261
His Gln Asn Leu Leu Arg Gly Ile Tyr Ser Tyr Gly Phe Glu Lys Pro
 35                  40                  45

TCC AGC ATC CAG CAG CGC GCC ATC GCC CCC TTC ACG CGC GGC GGC GAC        309
Ser Ser Ile Gln Gln Arg Ala Ile Ala Pro Phe Thr Arg Gly Gly Asp
 50                  55                  60                  65

ATC ATC GCG CAG GCG CAG TCC GGT ACC GGC AAG ACG GGC GCC TTC TCC        357
Ile Ile Ala Gln Ala Gln Ser Gly Thr Gly Lys Thr Gly Ala Phe Ser
                  70                  75                  80

ATC GGC CTG CTG CAG CGC CTG GAC TTC CGC CAC AAC CTG ATC CAG GGC        405
Ile Gly Leu Leu Gln Arg Leu Asp Phe Arg His Asn Leu Ile Gln Gly
              85                  90                  95

CTC GTG CTC TCC CCG ACC CGC GAG CTG GCC CTG CAG ACG GCG GAG GTG        453
Leu Val Leu Ser Pro Thr Arg Glu Leu Ala Leu Gln Thr Ala Glu Val
             100                 105                 110

ATC AGC CGC ATC GGC GAG TTC CTG TCG AAC AGC GCG AAG TTC TGT GAG        501
Ile Ser Arg Ile Gly Glu Phe Leu Ser Asn Ser Ala Lys Phe Cys Glu
         115                 120                 125

ACC TTT GTG GGT GGC ACG CGC GTG CAG GAT GAC CTG CGC AAG CTG CAG        549
Thr Phe Val Gly Gly Thr Arg Val Gln Asp Asp Leu Arg Lys Leu Gln
130                 135                 140                 145

GCT GGC GTC GTC GTC GCC GTG GGG ACG CCG GGC CGC GTG TCC GAC GTG        597
Ala Gly Val Val Val Ala Val Gly Thr Pro Gly Arg Val Ser Asp Val
                150                 155                 160

ATC AAG CGC GGC GCG CTG CGC ACC GAG TCC CTG CGC GTG CTG GTG CTC        645
```

-continued

```
Ile Lys Arg Gly Ala Leu Arg Thr Glu Ser Leu Arg Val Leu Val Leu
        165                 170                 175

GAC GAG GCT GAT GAG ATG CTG TCT CAG GGC TTC GCG GAT CAG ATT TAC      693
Asp Glu Ala Asp Glu Met Leu Ser Gln Gly Phe Ala Asp Gln Ile Tyr
            180                 185                 190

GAG ATC TTC CGC TTC CTG CCG AAG GAC ATC CAG GTC GCG CTC TTC TCC      741
Glu Ile Phe Arg Phe Leu Pro Lys Asp Ile Gln Val Ala Leu Phe Ser
195                 200                 205

GCC ACG ATG CCG GAG GAG GTG CTG GAG CTG ACA AAG AAG TTC ATG CGC      789
Ala Thr Met Pro Glu Glu Val Leu Glu Leu Thr Lys Lys Phe Met Arg
210                 215                 220                 225

GAC CCC GTA CGC ATT CTC GTG AAG CGC GAG AGC CTG ACG CTG GAG GGC      837
Asp Pro Val Arg Ile Leu Val Lys Arg Glu Ser Leu Thr Leu Glu Gly
                230                 235                 240

ATC AAG CAG TTC TTC ATC GCC GTC GAG GAG GAG CAC AAG CTG GAC ACG      885
Ile Lys Gln Phe Phe Ile Ala Val Glu Glu Glu His Lys Leu Asp Thr
            245                 250                 255

CTG ATG GAC CTG TAC GAG ACC GTG TCC ATC GCG CAG TCC GTC ATC TTC      933
Leu Met Asp Leu Tyr Glu Thr Val Ser Ile Ala Gln Ser Val Ile Phe
        260                 265                 270

GCC AAC ACC CGC CGC AAG GTG GAC TGG ATC GCC GAG AAG CTG AAT CAG      981
Ala Asn Thr Arg Arg Lys Val Asp Trp Ile Ala Glu Lys Leu Asn Gln
275                 280                 285

AGC AAC CAC ACC GTC AGC AGC ATG CAC GCC GAG ATG CCC AAG AGC GAC     1029
Ser Asn His Thr Val Ser Ser Met His Ala Glu Met Pro Lys Ser Asp
290                 295                 300                 305

CGC GAG CGC GTC ATG AAC ACC TTC CGC AGC GGC AGC TCC CGC GTG CTC     1077
Arg Glu Arg Val Met Asn Thr Phe Arg Ser Gly Ser Ser Arg Val Leu
                310                 315                 320

GTA ACG ACC GAC CTC GTG GCC CGC GGC ATC GAC GTG CAC CAC GTG AAC     1125
Val Thr Thr Asp Leu Val Ala Arg Gly Ile Asp Val His His Val Asn
            325                 330                 335

ATC GTC ATC AAC TTC GAC CTG CCG ACG AAC AAG GAG AAC TAC CTG CAC     1173
Ile Val Ile Asn Phe Asp Leu Pro Thr Asn Lys Glu Asn Tyr Leu His
        340                 345                 350

CGC ATT GGC CGC GGC GGC CGC TAC GGC GTA AAG GGT GTT GCC ATC AAC     1221
Arg Ile Gly Arg Gly Gly Arg Tyr Gly Val Lys Gly Val Ala Ile Asn
355                 360                 365

TTC GTG ACG GAG AAA GAC GTG GAG CTG CTG CAC GAG ATC GAG GGG CAC     1269
Phe Val Thr Glu Lys Asp Val Glu Leu Leu His Glu Ile Glu Gly His
370                 375                 380                 385

TAC CAC ACG CAG ATC GAT GAG CTC CCG GTG GAC TTT GCC GCC TAC CTC     1317
Tyr His Thr Gln Ile Asp Glu Leu Pro Val Asp Phe Ala Ala Tyr Leu
                390                 395                 400

GGC GAG TGA GCGGGCCCCT GCCCCCCTTC CCTGCCCCCC TCTCGCGACG             1366
Gly Glu

AGAGAACGCA CATCGTAACA CAGCCACGCG AACGATAGTA AGGGCGTGCG GCGGCGTTCC    1426

CCTCCTCCTG CCAGCGGCCC CCCTCCGCAG CGCTTCTCTT TTGAGAGGGG GGCAGGGGGA    1486

GGCGCTGCGC CTGGCTGGAT GTGTGCTTGA GCTTGCATTC CGTCAAGCAA GTGCTTTGTT    1546

TTAATTATGC GCGCCGTTTT GTTGCTCGTC CCTTTCGTTG GTGTTTTTTC GGCCGAAACG    1606

GCGTTTAAAG CA                                                        1618

(2) INFORMATION FOR SEQ ID NO:10:

(i) SEQUENCE CHARACTERISTICS:
        (A) LENGTH: 403 amino acids
        (B) TYPE: amino acid
        (D) TOPOLOGY: linear
```

(ii) MOLECULE TYPE: protein (xi) SEQUENCE DESCRIPTION: SEQ ID NO:10:

```
Met Ser Gln Gln Asp Arg Val Ala Pro Gln Asp Gln Asp Ser Phe Leu
  1               5                  10                  15

Asp Asp Gln Pro Gly Val Arg Pro Ile Pro Ser Phe Asp Asp Met Pro
             20                  25                  30

Leu His Gln Asn Leu Leu Arg Gly Ile Tyr Ser Tyr Gly Phe Glu Lys
             35                  40                  45

Pro Ser Ser Ile Gln Gln Arg Ala Ile Ala Pro Phe Thr Arg Gly Gly
         50                  55                  60

Asp Ile Ile Ala Gln Ala Gln Ser Gly Thr Gly Lys Thr Gly Ala Phe
 65                  70                  75                  80

Ser Ile Gly Leu Leu Gln Arg Leu Asp Phe Arg His Asn Leu Ile Gln
                 85                  90                  95

Gly Leu Val Leu Ser Pro Thr Arg Glu Leu Ala Leu Gln Thr Ala Glu
                100                 105                 110

Val Ile Ser Arg Ile Gly Glu Phe Leu Ser Asn Ser Ala Lys Phe Cys
            115                 120                 125

Glu Thr Phe Val Gly Gly Thr Arg Val Gln Asp Asp Leu Arg Lys Leu
        130                 135                 140

Gln Ala Gly Val Val Ala Val Gly Thr Pro Gly Arg Val Ser Asp
145                 150                 155                 160

Val Ile Lys Arg Gly Ala Leu Arg Thr Glu Ser Leu Arg Val Leu Val
                165                 170                 175

Leu Asp Glu Ala Asp Glu Met Leu Ser Gln Gly Phe Ala Asp Gln Ile
            180                 185                 190

Tyr Glu Ile Phe Arg Phe Leu Pro Lys Asp Ile Gln Val Ala Leu Phe
        195                 200                 205

Ser Ala Thr Met Pro Glu Glu Val Leu Glu Leu Thr Lys Lys Phe Met
210                 215                 220

Arg Asp Pro Val Arg Ile Leu Val Lys Arg Glu Ser Leu Thr Leu Glu
225                 230                 235                 240

Gly Ile Lys Gln Phe Phe Ile Ala Val Glu Glu Glu His Lys Leu Asp
                245                 250                 255

Thr Leu Met Asp Leu Tyr Glu Thr Val Ser Ile Ala Gln Ser Val Ile
            260                 265                 270

Phe Ala Asn Thr Arg Arg Lys Val Asp Trp Ile Ala Glu Lys Leu Asn
        275                 280                 285

Gln Ser Asn His Thr Val Ser Ser Met His Ala Glu Met Pro Lys Ser
290                 295                 300

Asp Arg Glu Arg Val Met Asn Thr Phe Arg Ser Gly Ser Ser Arg Val
305                 310                 315                 320

Leu Val Thr Thr Asp Leu Val Ala Arg Gly Ile Asp Val His His Val
                325                 330                 335

Asn Ile Val Ile Asn Phe Asp Leu Pro Thr Asn Lys Glu Asn Tyr Leu
            340                 345                 350

His Arg Ile Gly Arg Gly Gly Arg Tyr Gly Val Lys Gly Val Ala Ile
        355                 360                 365

Asn Phe Val Thr Glu Lys Asp Val Glu Leu Leu His Glu Ile Glu Gly
370                 375                 380

His Tyr His Thr Gln Ile Asp Glu Leu Pro Val Asp Phe Ala Ala Tyr
385                 390                 395                 400
```

Leu Gly Glu (2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 6
        (D) OTHER INFORMATION: /note= "Where Xaa is either a Leu
            or Lys Residue"

(xi) SEQUENCE DESCRIPTION: SEQ ID NO:11:

Xaa Gln Xaa Pro Gln Xaa Val Phe Asp Glu Xaa Xaa
1               5                   10

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: -
        (B) LOCATION: 11
        (D) OTHER INFORMATION: /note= "Where n is inosine"

(ix) FEATURE:
        (A) NAME/KEY: -
        (B) LOCATION: 17
        (D) OTHER INFORMATION: /note= "Where n is inosine"

(ix) FEATURE:
        (A) NAME/KEY: -
        (B) LOCATION: 20
        (D) OTHER INFORMATION: /note= "Where n is inosine"

(xi) SEQUENCE DESCRIPTION: SEQ ID NO:12:

GGAATTCCCC NCAGCTNGTN TTCGAC                                             26

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:13:

Lys Val Phe Asp Glu
1               5

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

GGATCCATGG TCAAGTCCCA CTACATCTGC                                         30

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:15:

```
GAATTCAGAC CGGATAGAAA TAAGCCAATG AAA                              33
```

(2) INFORMATION FOR SEQ ID NO:16:

(i) SEQUENCE CHARACTERISTICS:
        (A) LENGTH: 701 amino acids
        (B) TYPE: amino acid
        (C) STRANDEDNESS:
        (D) TOPOLOGY: linear (xi) SEQUENCE DESCRIPTION: SEQ ID NO:16:

```
Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Asp
            20                  25                  30

Val Ile Ser Asn Ala Ser Asp Ala Cys Asp Lys Ile Arg Tyr Gln Ser
        35                  40                  45

Leu Thr Asp Pro Ala Val Leu Gly Asp Ala Thr Arg Leu Cys Val Arg
    50                  55                  60

Val Val Pro Asp Lys Glu Asn Lys Thr Leu Thr Val Glu Asp Asn Gly
65                  70                  75                  80

Ile Gly Met Thr Lys Ala Asp Leu Val Asn Asn Leu Gly Thr Ile Ala
                85                  90                  95

Arg Ser Gly Thr Lys Ala Phe Met Glu Ala Leu Glu Ala Gly Ala Asp
            100                 105                 110

Met Ser Met Ile Gly Gln Phe Gly Val Gly Phe Tyr Ser Ala Tyr Leu
        115                 120                 125

Val Ala Asp Arg Val Thr Val Thr Ser Lys Asn Asn Ser Asp Glu Val
    130                 135                 140

Tyr Val Trp Glu Ser Ser Ala Gly Gly Thr Phe Thr Ile Thr Ser Ala
145                 150                 155                 160

Pro Glu Ser Asp Met Lys Leu Pro Ala Arg Ile Thr Leu His Leu Lys
                165                 170                 175

Glu Asp Gln Leu Glu Tyr Leu Glu Ala Arg Arg Leu Lys Glu Leu Ile
            180                 185                 190

Lys Lys His Ser Glu Phe Ile Gly Tyr Asp Ile Glu Leu Met Val Glu
        195                 200                 205

Lys Thr Thr Glu Lys Glu Val Thr Asp Glu Asp Glu Glu Glu Ala Lys
    210                 215                 220

Lys Ala Asp Glu Asp Gly Glu Glu Pro Lys Val Glu Glu Val Thr Glu
225                 230                 235                 240

Gly Glu Glu Asp Lys Lys Lys Thr Lys Lys Val Lys Glu Val Thr
                245                 250                 255

Lys Glu Tyr Glu Val Gln Asn Lys His Lys Pro Leu Trp Thr Arg Asp
            260                 265                 270

Pro Lys Asp Val Thr Lys Glu Glu Tyr Ala Ala Phe Tyr Lys Ala Ile
        275                 280                 285

Ser Asn Asp Trp Glu Asp Pro Pro Ala Thr Lys His Phe Ser Val Glu
    290                 295                 300
```

-continued

```
Gly Gln Leu Glu Phe Arg Ala Ile Met Phe Val Pro Lys Arg Ala Pro
305                 310                 315                 320

Phe Asp Met Leu Glu Pro Asn Lys Lys Arg Asn Asn Ile Lys Leu Tyr
                325                 330                 335

Val Arg Arg Val Phe Ile Met Asp Asn Cys Glu Asp Leu Cys Pro Asp
            340                 345                 350

Trp Leu Gly Phe Val Lys Gly Val Val Asp Ser Glu Asp Leu Pro Leu
        355                 360                 365

Asn Ile Ser Arg Glu Asn Leu Gln Gln Asn Lys Ile Leu Lys Val Ile
370                 375                 380

Arg Lys Asn Ile Val Lys Lys Cys Leu Glu Met Phe Glu Glu Val Ala
385                 390                 395                 400

Glu Asn Lys Glu Asp Tyr Lys Gln Phe Tyr Glu Gln Phe Gly Lys Asn
                405                 410                 415

Ile Lys Leu Gly Ile His Glu Asp Thr Ala Asn Arg Lys Lys Leu Met
            420                 425                 430

Glu Leu Leu Arg Phe Tyr Ser Thr Glu Ser Gly Glu Val Met Thr Thr
        435                 440                 445

Leu Lys Asp Tyr Val Thr Arg Met Lys Ala Glu Gln Asn Ser Ile Tyr
450                 455                 460

Tyr Ile Thr Gly Asp Ser Lys Lys Lys Leu Glu Ser Ser Pro Phe Ile
465                 470                 475                 480

Glu Gln Ala Lys Arg Arg Gly Phe Glu Val Leu Phe Met Thr Glu Pro
                485                 490                 495

Tyr Asp Glu Tyr Val Met Gln Gln Val Lys Asp Phe Glu Asp Lys Lys
            500                 505                 510

Phe Ala Cys Leu Thr Lys Glu Gly Val His Phe Glu Glu Ser Glu Glu
        515                 520                 525

Glu Lys Lys Gln Arg Glu Glu Lys Ala Thr Cys Glu Lys Leu Cys
530                 535                 540

Lys Thr Met Lys Glu Val Leu Gly Asp Lys Val Glu Lys Val Thr Val
545                 550                 555                 560

Ser Glu Arg Leu Ser Thr Ser Pro Cys Ile Leu Val Thr Ser Glu Phe
                565                 570                 575

Gly Trp Ser Ala His Met Glu Gln Met Met Arg Asn Gln Ala Leu Arg
            580                 585                 590

Asp Ser Ser Met Ala Gln Tyr Met Met Ser Lys Lys Thr Met Glu Leu
        595                 600                 605

Asn Pro Lys His Pro Ile Ile Lys Glu Leu Arg Arg Arg Val Glu Ala
610                 615                 620

Asp Glu Asn Asp Lys Ala Val Lys Asp Leu Val Phe Leu Leu Phe Asp
625                 630                 635                 640

Thr Ser Leu Leu Thr Ser Gly Phe Gln Leu Glu Asp Pro Thr Tyr Ala
                645                 650                 655

Glu Arg Ile Asn Arg Met Ile Lys Leu Gly Leu Ser Leu Asp Glu Glu
            660                 665                 670

Glu Glu Glu Glu Ala Val Glu Ala Ala Val Ala Glu Thr Ala Pro Ala
        675                 680                 685

Glu Val Thr Ala Gly Thr Ser Ser Met Glu Leu Val Asp
690                 695                 700
```

(2) INFORMATION FOR SEQ ID NO:17:

(i) SEQUENCE CHARACTERISTICS:
        (A) LENGTH: 704 amino acids
        (B) TYPE: amino acid
        (C) STRANDEDNESS:
        (D) TOPOLOGY: linear (xi) SEQUENCE DESCRIPTION: SEQ ID NO:17:

```
Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Glu
            20                  25                  30

Leu Ile Ser Asn Ala Ser Asp Ala Cys Asp Lys Ile Arg Tyr Gln Ser
            35                  40                  45

Leu Thr Asn Gln Ala Val Leu Gly Asp Glu Ser His Leu Arg Ile Arg
50                      55                  60

Val Val Pro Asp Lys Ala Asn Lys Thr Leu Thr Val Glu Asp Thr Gly
65                  70                  75                  80

Ile Gly Met Thr Lys Ala Glu Leu Val Asn Asn Leu Gly Thr Ile Ala
                85                  90                  95

Arg Ser Gly Thr Lys Ala Phe Met Glu Ala Leu Glu Ala Gly Gly Asp
            100                 105                 110

Met Ser Met Ile Gly Gln Phe Gly Val Gly Phe Tyr Ser Ala Tyr Leu
            115                 120                 125

Val Ala Asp Arg Val Thr Val Val Ser Lys Asn Asn Asp Asp Glu Ala
130                 135                 140

Tyr Thr Trp Glu Ser Ser Ala Gly Gly Thr Phe Thr Val Thr Pro Thr
145                 150                 155                 160

Pro Asp Cys Asp Leu Lys Arg Gly Thr Arg Ile Val Leu His Leu Lys
            165                 170                 175

Glu Asp Gln Gln Glu Tyr Leu Glu Glu Arg Arg Leu Lys Asp Leu Ile
            180                 185                 190

Lys Lys His Ser Glu Phe Ile Gly Tyr Asp Ile Glu Leu Met Val Glu
            195                 200                 205

Lys Ala Thr Glu Lys Glu Val Thr Asp Glu Asp Glu Asp Glu Ala Ala
            210                 215                 220

Ala Thr Lys Asn Glu Glu Gly Glu Glu Pro Lys Val Glu Glu Val Lys
225                 230                 235                 240

Asp Asp Ala Glu Glu Gly Glu Lys Lys Lys Thr Lys Lys Val Lys
            245                 250                 255

Glu Val Thr Gln Glu Phe Val Gln Asn Lys His Lys Pro Leu Trp
            260                 265                 270

Thr Arg Asp Pro Lys Asp Val Thr Lys Glu Glu Tyr Ala Ala Phe Tyr
            275                 280                 285

Lys Ala Ile Ser Asn Asp Trp Glu Glu Pro Leu Ser Thr Lys His Phe
290                 295                 300

Ser Val Glu Gly Gln Leu Glu Phe Arg Ala Ile Leu Phe Val Pro Lys
305                 310                 315                 320

Arg Ala Pro Phe Asp Met Phe Glu Pro Ser Lys Lys Arg Asn Asn Ile
            325                 330                 335

Lys Leu Tyr Val Arg Arg Val Phe Ile Met Asp Asn Cys Glu Asp Leu
            340                 345                 350

Cys Pro Glu Trp Leu Ala Phe Val Arg Gly Val Val Asp Ser Glu Asp
            355                 360                 365

Leu Pro Leu Asn Ile Ser Arg Glu Asn Leu Gln Gln Asn Lys Ile Leu
370                 375                 380
```

Lys Val Ile Arg Lys Asn Ile Val Lys Lys Ala Leu Glu Leu Phe Glu
385                 390                 395                 400

Glu Ile Ala Glu Asn Lys Glu Asp Tyr Lys Lys Phe Tyr Glu Gln Phe
            405                 410                 415

Gly Lys Asn Val Lys Leu Gly Ile His Glu Asp Ser Ala Asn Arg Lys
            420                 425                 430

Lys Leu Met Glu Leu Leu Arg Phe His Ser Glu Ser Gly Glu Asp
        435                 440                 445

Met Thr Thr Leu Lys Asp Tyr Val Thr Arg Met Lys Glu Gly Gln Lys
        450                 455                 460

Cys Ile Tyr Tyr Val Thr Gly Asp Ser Lys Lys Leu Glu Thr Ser
465                 470                 475                 480

Pro Phe Ile Glu Gln Ala Arg Arg Gly Phe Glu Val Leu Phe Met
            485                 490                 495

Thr Glu Pro Ile Asp Glu Tyr Val Met Gln Gln Val Lys Asp Phe Glu
            500                 505                 510

Asp Lys Lys Phe Ala Cys Leu Thr Lys Glu Gly Val His Phe Glu Glu
            515                 520                 525

Thr Glu Glu Lys Lys Gln Arg Glu Glu Lys Thr Ala Tyr Glu
            530                 535                 540

Arg Leu Cys Lys Ala Met Lys Asp Val Leu Gly Asp Lys Val Glu Lys
545                 550                 555                 560

Val Val Val Ser Glu Arg Leu Ala Thr Ser Pro Cys Ile Leu Val Thr
                565                 570                 575

Ser Glu Phe Gly Trp Ser Ala His Met Glu Gln Ile Met Arg Asn Gln
            580                 585                 590

Ala Leu Arg Asp Ser Ser Met Ser Ala Tyr Met Met Ser Lys Lys Thr
            595                 600                 605

Met Glu Ile Asn Pro Ala His Pro Ile Val Lys Glu Leu Lys Arg Arg
            610                 615                 620

Val Glu Ala Asp Glu Asn Asp Lys Ala Val Lys Asp Leu Val Tyr Leu
625                 630                 635                 640

Leu Phe Asp Thr Ala Leu Leu Thr Ser Gly Phe Thr Leu Asp Asp Pro
            645                 650                 655

Thr Ser Tyr Ala Glu Arg Ile His Arg Met Ile Lys Leu Gly Leu Ser
            660                 665                 670

Leu Asp Asp Glu Asp Asn Gly Asn Glu Glu Ala Glu Pro Ala Ala Ala
            675                 680                 685

Val Pro Ala Glu Pro Val Ala Gly Thr Ser Ser Met Glu Gln Val Asp
690                 695                 700

(2) INFORMATION FOR SEQ ID NO:18:

(i) SEQUENCE CHARACTERISTICS:
        (A) LENGTH: 732 amino acids
        (B) TYPE: amino acid
        (C) STRANDEDNESS:
        (D) TOPOLOGY: linear (xi) SEQUENCE DESCRIPTION: SEQ ID NO:18:

Met Pro Glu Glu Thr Gln Thr Gln Asp Gln Pro Met Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu

-continued

```
              35                  40                  45
Ile Ser Asn Ser Ser Asp Ala Leu Asp Lys Ile Arg Tyr Glu Ser Leu
 50                  55                  60

Thr Asp Pro Ser Lys Leu Asp Ser Gly Lys Glu Leu His Ile Asn Leu
 65                  70                  75                  80

Ile Pro Asn Lys Gln Asp Arg Ala Leu Thr Ile Val Asp Thr Gly Ile
                 85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
                115                 120                 125

Ser Met Ile Gly Gln Phe Gly Val Gly Phe Tyr Ser Ala Tyr Leu Val
                130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
                195                 200                 205

Lys His Ser Gln Phe Ile Gly Tyr Pro Ile Thr Leu Phe Val Glu Lys
                210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Asp Glu Lys Lys Asp Gly
                260                 265                 270

Asp Lys Lys Lys Lys Lys Ile Lys Glu Lys Tyr Ile Asp Lys Glu
                275                 280                 285

Glu Leu Asn Lys Thr Lys Pro Ile Trp Thr Arg Asn Pro Asp Asp Ile
                290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
                370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
                420                 425                 430

Asn Tyr Lys Lys Phe Tyr Glu Gln Phe Ser Lys Asn Ile Lys Leu Gly
                435                 440                 445

Ile His Glu Asp Ser Gln Asn Arg Lys Lys Leu Ser Glu Leu Leu Arg
                450                 455                 460
```

```
Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
            485                 490                 495

Glu Thr Lys Asp Gln Val Ala Asn Ser Ala Phe Val Glu Arg Leu Arg
        500                 505                 510

Lys His Gly Leu Glu Val Ile Tyr Met Ile Glu Pro Ile Asp Glu Tyr
    515                 520                 525

Cys Val Gln Gln Leu Lys Glu Phe Glu Gly Lys Thr Leu Val Ser Val
530                 535                 540

Thr Lys Glu Gly Leu Glu Leu Pro Glu Asp Glu Glu Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
            580                 585                 590

Val Thr Ser Pro Cys Cys Leu Val Thr Ser Thr Tyr Gly Trp Thr Ala
            595                 600                 605

Asn Met Glu Arg Ile Met Lys Ala Gln Ala Leu Arg Asp Asn Ser Thr
610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
            675                 680                 685

Tyr Arg Met Ile Lys Leu Gly Leu Gly Ile Asp Glu Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

(2) INFORMATION FOR SEQ ID NO:19:

(i) SEQUENCE CHARACTERISTICS:
        (A) LENGTH: 1019 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 71..523

(xi) SEQUENCE DESCRIPTION: SEQ ID NO:19:

GAATTCGGCA CGAGGTTTCT GTACTTTATT GCTTCCAGCC TTTATTCACT CTTCGATTTC    60

CTCTAACACC ATG TCC TCC GAG CGC ACC TTT ATT GCC GTC AAG CCG GAC      109
           Met Ser Ser Glu Arg Thr Phe Ile Ala Val Lys Pro Asp
            1               5                  10

GGC GTG CAG CGC GGC CTC GTT GGC GAG ATC ATC GCC CGC TTC GAG CGC    157
```

```
Gly Val Gln Arg Gly Leu Val Gly Glu Ile Ile Ala Arg Phe Glu Arg
         15                  20                  25

AAG GGC TAC AAG CTC GTC GCC TTG AAG ATA CTG CAG CCG ACG ACG GAG      205
Lys Gly Tyr Lys Leu Val Ala Leu Lys Ile Leu Gln Pro Thr Thr Glu
 30                  35                  40                  45

CAG GCC CAG GGT CAC TAT AAG GAC CTT TGC TCC AAG CCG TTT TTC CCG      253
Gln Ala Gln Gly His Tyr Lys Asp Leu Cys Ser Lys Pro Phe Phe Pro
                 50                  55                  60

GCC CTT GTG AAG TAC TTC TCC TCT GGC CCG ATC GTG TGT ATG GTG TGG      301
Ala Leu Val Lys Tyr Phe Ser Ser Gly Pro Ile Val Cys Met Val Trp
             65                  70                  75

GAG GGT AAG AAC GTG GTG AAG AGC GGC CGC GTG CTG CTC GGC GCG ACG      349
Glu Gly Lys Asn Val Val Lys Ser Gly Arg Val Leu Leu Gly Ala Thr
         80                  85                  90

AAC CCG GCC GAC TCA CAG CCC GGC ACG ATC CGT GGC GAC TTT GCC GTG      397
Asn Pro Ala Asp Ser Gln Pro Gly Thr Ile Arg Gly Asp Phe Ala Val
 95                 100                 105

GAT GTG GGC CGC AAC GTG TGC CAC GGG TCC GAC TCT GTG GAG AGC GCG      445
Asp Val Gly Arg Asn Val Cys His Gly Ser Asp Ser Val Glu Ser Ala
110                 115                 120                 125

GAG CGC GAG ATC GCC TTT TGG TTC AAG GCG GAT GAG ATC GCG AGC TGG      493
Glu Arg Glu Ile Ala Phe Trp Phe Lys Ala Asp Glu Ile Ala Ser Trp
                130                 135                 140

ACG TCG CAC TCC GTG TCC CAG ATC TAT GAG TAACGGTGAT GCGGACACG         543
Thr Ser His Ser Val Ser Gln Ile Tyr Glu
            145                 150

CTTTGAGGAC GTAGCTGTAC CCCCAATGAA TTCTTCTCTG AAAACCACAT CATAAGCCTC    603

TTAAGAGGTT ATTTTTCTTG ATCGATGCCC GGTGGTGACC AGCACCATTC CTTTATCGGA    663

TTCACTCACA CTCCTAGCGA ATCATGTAGT GCGGTGAGAG TGGGCTCTGG AGGAGACTGT    723

TGTGTAGCCA TGGCTTCAGG AGAGAAAACA AAATACAAGG AAAGGCAATA TGTAACTATG    783

GGGTTCCCTT TTTTACTATG CAAAGTTTTT ATAACTCCTG ATCGGCAAAA ACAACAACAA    843

CCGCCATACA CCAAGAGCAA ATGCTTTCTT CTGCGGACTG TGCTTCTGTT TTTTTTTATG    903

AAGGAGTGAC TCGCGCGATG AAAAGTGTGT GCGTGGGAGA TGTATTTCCT TTTTTTGTTC    963

ATAGTGGCGA CAGCTCACTG TTGACGATGA CAAAAAAAAA AAAAAAAAAA CTCGAG       1019

(2) INFORMATION FOR SEQ ID NO:20:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:20:

Met Ser Ser Glu Arg Thr Phe Ile Ala Val Lys Pro Asp Gly Val Gln
 1               5                  10                  15

Arg Gly Leu Val Gly Glu Ile Ile Ala Arg Phe Glu Arg Lys Gly Tyr
                 20                  25                  30

Lys Leu Val Ala Leu Lys Ile Leu Gln Pro Thr Thr Glu Gln Ala Gln
             35                  40                  45

Gly His Tyr Lys Asp Leu Cys Ser Lys Pro Phe Phe Pro Ala Leu Val
         50                  55                  60

Lys Tyr Phe Ser Ser Gly Pro Ile Val Cys Met Val Trp Glu Gly Lys
 65                  70                  75                  80

Asn Val Val Lys Ser Gly Arg Val Leu Leu Gly Ala Thr Asn Pro Ala
```

```
                        85                      90                      95
Asp Ser Gln Pro Gly Thr Ile Arg Gly Asp Phe Ala Val Asp Val Gly
                100                     105                     110

Arg Asn Val Cys His Gly Ser Asp Ser Val Glu Ser Ala Glu Arg Glu
            115                     120                     125

Ile Ala Phe Trp Phe Lys Ala Asp Glu Ile Ala Ser Trp Thr Ser His
    130                     135                     140

Ser Val Ser Gln Ile Tyr Glu
145                 150

(2) INFORMATION FOR SEQ ID NO:21:

(i) SEQUENCE CHARACTERISTICS:
        (A) LENGTH: 1523 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 14..973

(xi) SEQUENCE DESCRIPTION: SEQ ID NO:21:
```

| | | |
|---|---|---|
| GAATTCGGCA CGA GTG CTG CCC GAC ATG ACA TGC TCG CTG ACC GGA CTT | 49 | |
| Val Leu Pro Asp Met Thr Cys Ser Leu Thr Gly Leu | | |
| 1 5 10 | | |
| CAG TGC ACA GAC CCG AAC TGC AAG ACC TGC ACA ACT TAC GGT CAG TGC | 97 | |
| Gln Cys Thr Asp Pro Asn Cys Lys Thr Cys Thr Thr Tyr Gly Gln Cys | | |
| 15 20 25 | | |
| ACA GAC TGC AAC GAC GGC TAC GGT CTC ACC TCC TCC AGC GTT TGC GTG | 145 | |
| Thr Asp Cys Asn Asp Gly Tyr Gly Leu Thr Ser Ser Ser Val Cys Val | | |
| 30 35 40 | | |
| CGC TGC AGT GTA GCG GGC TGC AAG AGC TGC CCC GTC GAC GCT AAC GTC | 193 | |
| Arg Cys Ser Val Ala Gly Cys Lys Ser Cys Pro Val Asp Ala Asn Val | | |
| 45 50 55 60 | | |
| TGC AAA GTG TGT CTC GGC GGC AGC GAG CCG ATC AAC AAT ATG TGC CCC | 241 | |
| Cys Lys Val Cys Leu Gly Gly Ser Glu Pro Ile Asn Asn Met Cys Pro | | |
| 65 70 75 | | |
| TGC ACC GAC CCC AAC TGC GCC AGC TGC CCC AGC GAC GCT GGC ACG TGC | 289 | |
| Cys Thr Asp Pro Asn Cys Ala Ser Cys Pro Ser Asp Ala Gly Thr Cys | | |
| 80 85 90 | | |
| ACT CAG TGC GCG AAC GGC TAC GGT CTC GTG GAC GGC GCC TGT GTG AGA | 337 | |
| Thr Gln Cys Ala Asn Gly Tyr Gly Leu Val Asp Gly Ala Cys Val Arg | | |
| 95 100 105 | | |
| TGC CAG GAG CCC AAC TGC TTC AGC TGC GAC AGC GAC GCG AAT AAG TGC | 385 | |
| Cys Gln Glu Pro Asn Cys Phe Ser Cys Asp Ser Asp Ala Asn Lys Cys | | |
| 110 115 120 | | |
| ACA CAA TGT GCG CCG AAC TAC TAC CTC ACC CCG CTC TTG ACC TGC TCC | 433 | |
| Thr Gln Cys Ala Pro Asn Tyr Tyr Leu Thr Pro Leu Leu Thr Cys Ser | | |
| 125 130 135 140 | | |
| CCG GTG GCC TGC AAC ATC GAG CAC TGC ATG CAG TGC GAC CCA CAG ACG | 481 | |
| Pro Val Ala Cys Asn Ile Glu His Cys Met Gln Cys Asp Pro Gln Thr | | |
| 145 150 155 | | |
| CCG TCG CGC TGC CAG GAG TGC GTG TCC CCC TAC GTG GTT GAC AGC TAC | 529 | |
| Pro Ser Arg Cys Gln Glu Cys Val Ser Pro Tyr Val Val Asp Ser Tyr | | |
| 160 165 170 | | |
| GAC GGC CTC TGC AGG CTC TCC GAT GCC TGC TCC GTG CCC AAC TGC AAG | 577 | |

-continued

```
Asp Gly Leu Cys Arg Leu Ser Asp Ala Cys Ser Val Pro Asn Cys Lys
            175                 180                 185

AAG TGC GAG ACC GGT ACC TCC AGG CTC TGC GCC GAG TGC GAC ACC GGC       625
Lys Cys Glu Thr Gly Thr Ser Arg Leu Cys Ala Glu Cys Asp Thr Gly
    190                 195                 200

TAC AGT CTC TCC GCC GAC GCG ACG AGC TGC AGC AGT CCA ACC ACG CAG       673
Tyr Ser Leu Ser Ala Asp Ala Thr Ser Cys Ser Ser Pro Thr Thr Gln
205                 210                 215                 220

CCG TGC GAG GTG GAG CAC TGC AAC ACA TGT GTG AAC GGC GAT AGC ACC       721
Pro Cys Glu Val Glu His Cys Asn Thr Cys Val Asn Gly Asp Ser Thr
                225                 230                 235

CGC TGT GCC TAC TGC AAC ACC GGC TAC TAC GTC TCC GAT GGC AAG TGC       769
Arg Cys Ala Tyr Cys Asn Thr Gly Tyr Tyr Val Ser Asp Gly Lys Cys
            240                 245                 250

AAG GCC ATG CAG GGC TGC TAC GTG TCG AAC TGC GCG CAG TGC ATG CTG       817
Lys Ala Met Gln Gly Cys Tyr Val Ser Asn Cys Ala Gln Cys Met Leu
        255                 260                 265

CTT GAC AGC ACC AAG TGC TCC ACG TGC GTG AAA GGG TAC CTG CTC ACG       865
Leu Asp Ser Thr Lys Cys Ser Thr Cys Val Lys Gly Tyr Leu Leu Thr
    270                 275                 280

TCG TCC TAC AGT TGC GTC TCG CAG AAA GTC ATC AAC AGT GCG GCC GCG       913
Ser Ser Tyr Ser Cys Val Ser Gln Lys Val Ile Asn Ser Ala Ala Ala
285                 290                 295                 300

CCC TAC TCT CTG TGG GTG GCC GCC GCC GTG CTC CTC ACC TCT TTT GCC       961
Pro Tyr Ser Leu Trp Val Ala Ala Ala Val Leu Leu Thr Ser Phe Ala
                305                 310                 315

ATG CAC CTA GCA TAGTGCGCAG CGGCATGCGA ACAACCCCAC TCTCATTCTC          1013
Met His Leu Ala
            320

CAACATGTGC ATACACACAC ACACAGACAG CGGGGCAGCA CCCCCTCCCC ACACACACAC    1073

ACGCACTTCC CCCTTGTCTT GTTCTTCTTT CCTCGTTCGC ATTTCTTTCT CTCGTGCGCT    1133

GGCGCCGGCC TCCTGCACGT CGCTCCCCTC CCCCTAACCT CTATTCTCTC TCTCTCTCTC    1193

TCTCGCCGGC ATCATTGCTT CTTACCCTTT TCTGATCCTT GCTCGCGTGG GCGGACACTG    1253

CCACAGTCCC ACAGCGCAGA CACACGTGTT TAAACGGCGC AGGCATCCCT CCCTATCACT    1313

TCATTTCTCC TAAAGCCACT CACCAAGTCG CACACCGCCC TCCCCCATCG GCCGCCCTTC    1373

CGGGCGCAGC TGTGCGGAAT GGGTGTGTGC TCGACCTCGT TCCTGGCAGC TCACTCGCAT    1433

GTGTACAGCC ACTCCAACCA CGAAAGCTCT CTTCTGCGCA CATAAAAAAA AAAAAAAAA    1493

AAAAACTCGA GGGGGGGCCC GGTACCCAAA                                    1523
```

(2) INFORMATION FOR SEQ ID NO:22:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:22:

```
Val Leu Pro Asp Met Thr Cys Ser Leu Thr Gly Leu Gln Cys Thr Asp
1               5                   10                  15

Pro Asn Cys Lys Thr Cys Thr Thr Tyr Gly Gln Cys Thr Asp Cys Asn
            20                  25                  30

Asp Gly Tyr Gly Leu Thr Ser Ser Val Cys Val Arg Cys Ser Val
        35                  40                  45

Ala Gly Cys Lys Ser Cys Pro Val Asp Ala Asn Val Cys Lys Val Cys
```

```
                  50                  55                  60
Leu Gly Gly Ser Glu Pro Ile Asn Asn Met Cys Pro Cys Thr Asp Pro
 65                  70                  75                  80

Asn Cys Ala Ser Cys Pro Ser Asp Ala Gly Thr Cys Thr Gln Cys Ala
                 85                  90                  95

Asn Gly Tyr Gly Leu Val Asp Gly Ala Cys Val Arg Cys Gln Glu Pro
                100                 105                 110

Asn Cys Phe Ser Cys Asp Ser Asp Ala Asn Lys Cys Thr Gln Cys Ala
                115                 120                 125

Pro Asn Tyr Tyr Leu Thr Pro Leu Leu Thr Cys Ser Pro Val Ala Cys
                130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
                180                 185                 190

Gly Thr Ser Arg Leu Cys Ala Glu Cys Asp Thr Gly Tyr Ser Leu Ser
                195                 200                 205

Ala Asp Ala Thr Ser Cys Ser Ser Pro Thr Thr Gln Pro Cys Glu Val
210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
                260                 265                 270

Lys Cys Ser Thr Cys Val Lys Gly Tyr Leu Leu Thr Ser Ser Tyr Ser
                275                 280                 285

Cys Val Ser Gln Lys Val Ile Asn Ser Ala Ala Pro Tyr Ser Leu
                290                 295                 300

Trp Val Ala Ala Val Leu Leu Thr Ser Phe Ala Met His Leu Ala
305                 310                 315                 320

(2) INFORMATION FOR SEQ ID NO:23:

(i) SEQUENCE CHARACTERISTICS:
        (A) LENGTH: 797 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania major (ix) FEATURE:
        (A) NAME/KEY: CDS
        (B) LOCATION: 27..623

(xi) SEQUENCE DESCRIPTION: SEQ ID NO:23:

CTGTACTTTA TTGCCACCAG CCAGCC ATG TCC TGC GGT AAC GCC AAG ATC AAC        53
                            Met Ser Cys Gly Asn Ala Lys Ile Asn
                             1               5

TCT CCC GCG CCG TCC TTC GAG GAG GTG GCG CTC ATG CCC AAC GGC AGC       101
Ser Pro Ala Pro Ser Phe Glu Glu Val Ala Leu Met Pro Asn Gly Ser
 10                  15                  20                  25

TTC AAG AAG ATC AGC CTC TCC TCC TAC AAG GGC AAG TGG GTC GTG CTC       149
```

-continued

```
Phe Lys Lys Ile Ser Leu Ser Ser Tyr Lys Gly Lys Trp Val Val Leu
                30                  35                  40

TTC TTC TAC CCG CTC GAC TTT AGC TTC GTG TGC CCG ACA GAG GTC ATC      197
Phe Phe Tyr Pro Leu Asp Phe Ser Phe Val Cys Pro Thr Glu Val Ile
                45                  50                  55

GCG TTC TCC GAC AGC GTG AGT CGC TTC AAC GAG CTC AAC TGC GAG GTC      245
Ala Phe Ser Asp Ser Val Ser Arg Phe Asn Glu Leu Asn Cys Glu Val
                60                  65                  70

CTC GCG TGC TCG ATA GAC AGC GAG TAC GCG CAC CTG CAG TGG ACG CTG      293
Leu Ala Cys Ser Ile Asp Ser Glu Tyr Ala His Leu Gln Trp Thr Leu
        75                  80                  85

CAG GAC CGC AAG AAG GGC GGC CTC GGG ACC ATG GCG ATC CCA ATG CTA      341
Gln Asp Arg Lys Lys Gly Gly Leu Gly Thr Met Ala Ile Pro Met Leu
 90                  95                 100                 105

GCC GAC AAG ACC AAG AGC ATC GCT CGT TCC TAC GGC GTG CTG GAG GAG      389
Ala Asp Lys Thr Lys Ser Ile Ala Arg Ser Tyr Gly Val Leu Glu Glu
                110                 115                 120

AGC CAG GGC GTG GCC TAC CGC GGT CTC TTC ATC ATC GAC CCC CAT GGC      437
Ser Gln Gly Val Ala Tyr Arg Gly Leu Phe Ile Ile Asp Pro His Gly
                125                 130                 135

ATG CTG CGT CAG ATC ACC GTC AAT GAC ATG CCG GTG GGC CGC AGC GTG      485
Met Leu Arg Gln Ile Thr Val Asn Asp Met Pro Val Gly Arg Ser Val
        140                 145                 150

GAG GAG GTT CTA CGC CTG CTG GAG GCT TTT CAG TTC GTG GAG AAG CAC      533
Glu Glu Val Leu Arg Leu Leu Glu Ala Phe Gln Phe Val Glu Lys His
 155                 160                 165

GGC GAG GTG TGC CCC GCG AAC TGG AAG AAG GGC GCC CCC ACG ATG AAG      581
Gly Glu Val Cys Pro Ala Asn Trp Lys Lys Gly Ala Pro Thr Met Lys
170                 175                 180                 185

CCG GAA CCG AAT GCG TCT GTC GAG GGA TAC TTC AGC AAG CAG              623
Pro Glu Pro Asn Ala Ser Val Glu Gly Tyr Phe Ser Lys Gln
                190                 195

TAAACCTGTG AGCGTCGCAG GAGTCAGTGT GACCTCACCC GCCTCTGCCA GTGGGTGCGA    683

GAGGGCGTGA GGGATTGTGG GAAGGCTGTT GGATATGATG CAGACAGCGA TGAATGCAAC    743

TCCCACACAC TGGCCCTCCT CAGCCCTCTC CACACAGACA CACGCACGCA TGTG          797
```

(2) INFORMATION FOR SEQ ID NO:24:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:24:

```
Met Ser Cys Gly Asn Ala Lys Ile Asn Ser Pro Ala Pro Ser Phe Glu
 1               5                  10                  15

Glu Val Ala Leu Met Pro Asn Gly Ser Phe Lys Lys Ile Ser Leu Ser
                20                  25                  30

Ser Tyr Lys Gly Lys Trp Val Val Leu Phe Phe Tyr Pro Leu Asp Phe
        35                  40                  45

Ser Phe Val Cys Pro Thr Glu Val Ile Ala Phe Ser Asp Ser Val Ser
 50                  55                  60

Arg Phe Asn Glu Leu Asn Cys Glu Val Leu Ala Cys Ser Ile Asp Ser
 65                  70                  75                  80

Glu Tyr Ala His Leu Gln Trp Thr Leu Gln Asp Arg Lys Lys Gly Gly
                85                  90                  95
```

```
Leu Gly Thr Met Ala Ile Pro Met Leu Ala Asp Lys Thr Lys Ser Ile
            100                 105                 110

Ala Arg Ser Tyr Gly Val Leu Glu Glu Ser Gln Gly Val Ala Tyr Arg
        115                 120                 125

Gly Leu Phe Ile Ile Asp Pro His Gly Met Leu Arg Gln Ile Thr Val
    130                 135                 140

Asn Asp Met Pro Val Gly Arg Ser Val Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Asn Ala Ser Val
            180                 185                 190

Glu Gly Tyr Phe Ser Lys Gln
        195
```

(2) INFORMATION FOR SEQ ID NO:25:

(i) SEQUENCE CHARACTERISTICS:
        (A) LENGTH: 637 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Leishmania tropica (ix) FEATURE:
        (A) NAME/KEY: CDS
        (B) LOCATION: 7..624

(xi) SEQUENCE DESCRIPTION: SEQ ID NO:25:

```
TTACAT ATG CAT CAC CAC CAC CAC CAC ATG TCC TGC GGT AAC GCC AAG        48
       Met His His His His His His Met Ser Cys Gly Asn Ala Lys
         1               5                  10

ATC AAC TCT CCC GCG CCG CCC TTC GAG GAG ATG GCG CTC ATG CCC AAC       96
Ile Asn Ser Pro Ala Pro Pro Phe Glu Glu Met Ala Leu Met Pro Asn
 15                  20                  25                  30

GGC AGC TTC AAG AAG ATC AGC CTC TCC GCC TAC AAG GGC AAG TGG GTC      144
Gly Ser Phe Lys Lys Ile Ser Leu Ser Ala Tyr Lys Gly Lys Trp Val
                 35                  40                  45

GTG CTC TTC TTC TAC CCG CTC GAC TTC ACC TTC GTG TGC CCG ACA GAG      192
Val Leu Phe Phe Tyr Pro Leu Asp Phe Thr Phe Val Cys Pro Thr Glu
             50                  55                  60

ATC ATC GCG TTC TCC GAC AAC GTG AGT CGC TTC AAC GAG CTC AAC TGC      240
Ile Ile Ala Phe Ser Asp Asn Val Ser Arg Phe Asn Glu Leu Asn Cys
 65                  70                  75

GAG GTC CTC GCG TGC TCG ATG GAC AGC GAG TAC GCG CAC CTG CAG TGG      288
Glu Val Leu Ala Cys Ser Met Asp Ser Glu Tyr Ala His Leu Gln Trp
         80                  85                  90

ACG CTG CAG GAC CGC AAG AAG GGC GGC CTC GGG GCC ATG GCG ATC CCA      336
Thr Leu Gln Asp Arg Lys Lys Gly Gly Leu Gly Ala Met Ala Ile Pro
 95                  100                 105                 110

ATG CTG GCC GAC AAG ACT AAG AGC ATC GCT CGT TCC TAC GGC GTG CTG      384
Met Leu Ala Asp Lys Thr Lys Ser Ile Ala Arg Ser Tyr Gly Val Leu
                 115                 120                 125

GAG GAG AGC CAG GGC GTG GCC TAC CGC GGT CTC TTC ATC ATC GAC CCC      432
Glu Glu Ser Gln Gly Val Ala Tyr Arg Gly Leu Phe Ile Ile Asp Pro
             130                 135                 140

CGT GGC ATG GTG CGT CAG ATC ACC GTC AAC GAC ATG CCG GTG GGC CGC      480
Arg Gly Met Val Arg Gln Ile Thr Val Asn Asp Met Pro Val Gly Arg
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 145 |     |     |     |     | 150 |     |     |     |     |     | 155 |     |     |

```
AAC GTG GAG GAG GCT CTG CGC CTG CTG GAG GCT TTG CAG TTC GTG GAG     528
Asn Val Glu Glu Ala Leu Arg Leu Leu Glu Ala Leu Gln Phe Val Glu
    160                 165                 170

AAG CAC GGC GAG GTG TGC CCC GCG AAC TGG AAG AAG GGC GCC CCC ACG     576
Lys His Gly Glu Val Cys Pro Ala Asn Trp Lys Lys Gly Ala Pro Thr
175                 180                 185                 190

ATG AAG CCG GAA CCG AAG GCG TCT GTC GAG GGA TAC TTC AGC AAG CAG     624
Met Lys Pro Glu Pro Lys Ala Ser Val Glu Gly Tyr Phe Ser Lys Gln
                195                 200                 205

TAAGAATTCC ATG                                                      637
```

(2) INFORMATION FOR SEQ ID NO:26:

(i) SEQUENCE CHARACTERISTICS:
        (A) LENGTH: 206 amino acids
        (B) TYPE: amino acid
        (D) TOPOLOGY: linear (ii) MOLECULE TYPE: protein (xi) SEQUENCE DESCRIPTION: SEQ ID NO:26:

```
Met His His His His His Met Ser Cys Gly Asn Ala Lys Ile Asn
1                   5                   10                  15

Ser Pro Ala Pro Pro Phe Glu Glu Met Ala Leu Met Pro Asn Gly Ser
            20                  25                  30

Phe Lys Lys Ile Ser Leu Ser Ala Tyr Lys Gly Lys Trp Val Val Leu
            35                  40                  45

Phe Phe Tyr Pro Leu Asp Phe Thr Phe Val Cys Pro Thr Glu Ile Ile
        50                  55                  60

Ala Phe Ser Asp Asn Val Ser Arg Phe Asn Glu Leu Asn Cys Glu Val
65                  70                  75                  80

Leu Ala Cys Ser Met Asp Ser Glu Tyr Ala His Leu Gln Trp Thr Leu
                85                  90                  95

Gln Asp Arg Lys Lys Gly Gly Leu Gly Ala Met Ala Ile Pro Met Leu
                100                 105                 110

Ala Asp Lys Thr Lys Ser Ile Ala Arg Ser Tyr Gly Val Leu Glu Glu
            115                 120                 125

Ser Gln Gly Val Ala Tyr Arg Gly Leu Phe Ile Ile Asp Pro Arg Gly
130                 135                 140

Met Val Arg Gln Ile Thr Val Asn Asp Met Pro Val Gly Arg Asn Val
145                 150                 155                 160

Glu Glu Ala Leu Arg Leu Leu Glu Ala Leu Gln Phe Val Glu Lys His
                165                 170                 175

Gly Glu Val Cys Pro Ala Asn Trp Lys Lys Gly Ala Pro Thr Met Lys
            180                 185                 190

Pro Glu Pro Lys Ala Ser Val Glu Gly Tyr Phe Ser Lys Gln
            195                 200                 205
```

(2) INFORMATION FOR SEQ ID NO:27:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5 PCR primer (MAPS-1-5 His)
           to simultaneously amplify MAPS-1 cDNA for both L. major -continued and L. tropica while adding 6 His residues to amino
terminal end of encoded protein."

(xi) SEQUENCE DESCRIPTION: SEQ ID NO:27:

CAATTACATA TGCATCACCA TCACCATCAC ATGTCCTGCG GTAACGCCAA G          51

(2) INFORMATION FOR SEQ ID NO:28:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "3' PCR primer (MAPS-1-3 R1) to
         simultaneously amplify MAPS-1 cDNA for both L. major and
         L. tropica.

(xi) SEQUENCE DESCRIPTION: SEQ ID NO:28:

CATGGAATTC TTACTGCTTG CTGAAGTATC C          31

LEISHMANIA ANTIGENS FOR USE IN THE THERAPY AND DIAGNOSIS OF LEISHMANIASIS

REFERENCE TO RELATED APPLICATIONS

This application is a continuation-in-part of U.S. patent application Ser. No. 08/533,669, filed Sep. 22, 1995 now U.S. Pat. No. 5,834,592.

TECHNICAL FIELD

The present invention relates generally to compositions and methods for preventing, treating and detecting leishmaniasis, and for stimulating immune responses in patients. The invention is more particularly related to polypeptides comprising an immunogenic portion of a Leishmania antigen or a variant thereof, and to vaccines and pharmaceutical compositions comprising one or more such polypeptides. The vaccines and pharmaceutical compositions may be used, for example, for the prevention and therapy of leishmaniasis, as well as for the detection of Leishmania infection.

BACKGROUND OF THE INVENTION

Leishmania organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is frequently difficult to achieve. There are 20 species of Leishmania that infect humans, including *L. donovani, L. chagasi, L. infantum, L. major, L. amazonensis, L. braziliensis, L. panamensis, L. mexicana, L. tropica, and L. guyanensis*, and there are no distinctive signs or symptoms that unambiguously indicate the presence of Leishmania infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable. Thus, there is a need for improved methods for the detection of Leishmania infection.

Current experimental vaccines consisting of whole organisms have not proven effective in humans. Accordingly, there remains a need in the art for vaccines to prevent leishmaniasis in humans and dogs, and for improved therapeutic compositions for the treatment of leishmaniasis.

SUMMARY OF THE INVENTION

Briefly stated, the present invention provides compositions and methods for preventing, treating and detecting leishmaniasis, as well as for stimulating immune responses in patients. In one aspect, polypeptides are provided which comprise at least an immunogenic portion of a Leishmania antigen, or a variant of such an antigen that differs only in conservative substitutions and/or modifications. In specific embodiments of the invention, the Leishmania antigen comprises an amino acid sequence selected from the group consisting of SEQ ID Nos: 2, 4, 20, 22, 24 and 26. DNA sequences encoding the above polypeptides, recombinant expression vectors comprising these DNA sequences and host cells transformed or transfected with such expression vectors are also provided.

In related aspects, the present invention provides pharmaceutical compositions which comprise one or more of the polypeptides described herein, or a DNA molecule encoding such polypeptides, and a physiologically acceptable carrier. Vaccines which comprise one or more such polypeptides or DNA molecules, together with a non-specific immune response enhancer are also provided. In specific embodiments of these aspects, the Leishmania antigen has an amino acid sequence selected from the group consisting of SEQ ID Nos: 2, 4, 20, 22, 24 and 26.

In still further related embodiments, the pharmaceutical compositions and vaccines comprise at least two different polypeptides, each polypeptide comprising an immunogenic portion of a Leishmania antigen having an amino acid sequence selected from the group consisting of sequences recited in SEQ ID Nos: 2, 4, 6, 8, 10, 20, 22, 24 and 26 and variants thereof that differ only in conservative substitutions and/or modifications.

In other related embodiments, the pharmaceutical compositions and vaccines comprise soluble Leishmania antigens.

In another aspect, the present invention provides methods for inducing protective immunity against leishmaniasis in a patient, comprising administering to a patient a pharmaceutical composition or vaccine as described above.

In further aspects, methods and diagnostic kits are provided for detecting Leishmania infection in a patient. The methods comprise: (a) contacting dermal cells of a patient with a pharmaceutical composition as described above; and (b) detecting an immune response on the patient's skin, therefrom detecting Leishmania infection in the patient. The diagnostic kits comprise: (a) a pharmaceutical composition as described above; and (b) an apparatus sufficient to contact the pharmaceutical composition with the dermal cells of a patient.

In further aspects, the present invention provides methods for stimulating a cellular and/or humoral immune response in a patient, comprising administering to a patient a pharmaceutical composition or vaccine as described above.

In a related aspect, methods are provided for treating a patient afflicted with a disease responsive to IL-12 stimulation, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 2 illustrates representative HPLC profiles of peptides isolated from MHC class II molecules of P388D1 macrophages. Panel A shows peptides isolated from uninfected macrophages and panel B shows peptides isolated from *L. donovani* infected macrophages. The arrows in panel B indicate peptide peaks present only in the infected macrophage preparation.

FIG. 5 shows a Western blot analysis of *L. donovani* promastigote antigens incubated with pre-immune rabbit serum (lane A) or with anti-Ldp23 rabbit antiserum (lane B).

FIG. 19 presents a comparison of a Lbhsp83 sequence with homologous sequences from *L. amazonensis* (Lahsp83), *T. cruzi* (Tchsp83) and humans (Huhsp89).

FIG. 21 shows the cDNA and predicted amino acid sequence for the Leishmania antigen Lmspla.

DETAILED DESCRIPTION OF THE INVENTION

Figure 1:
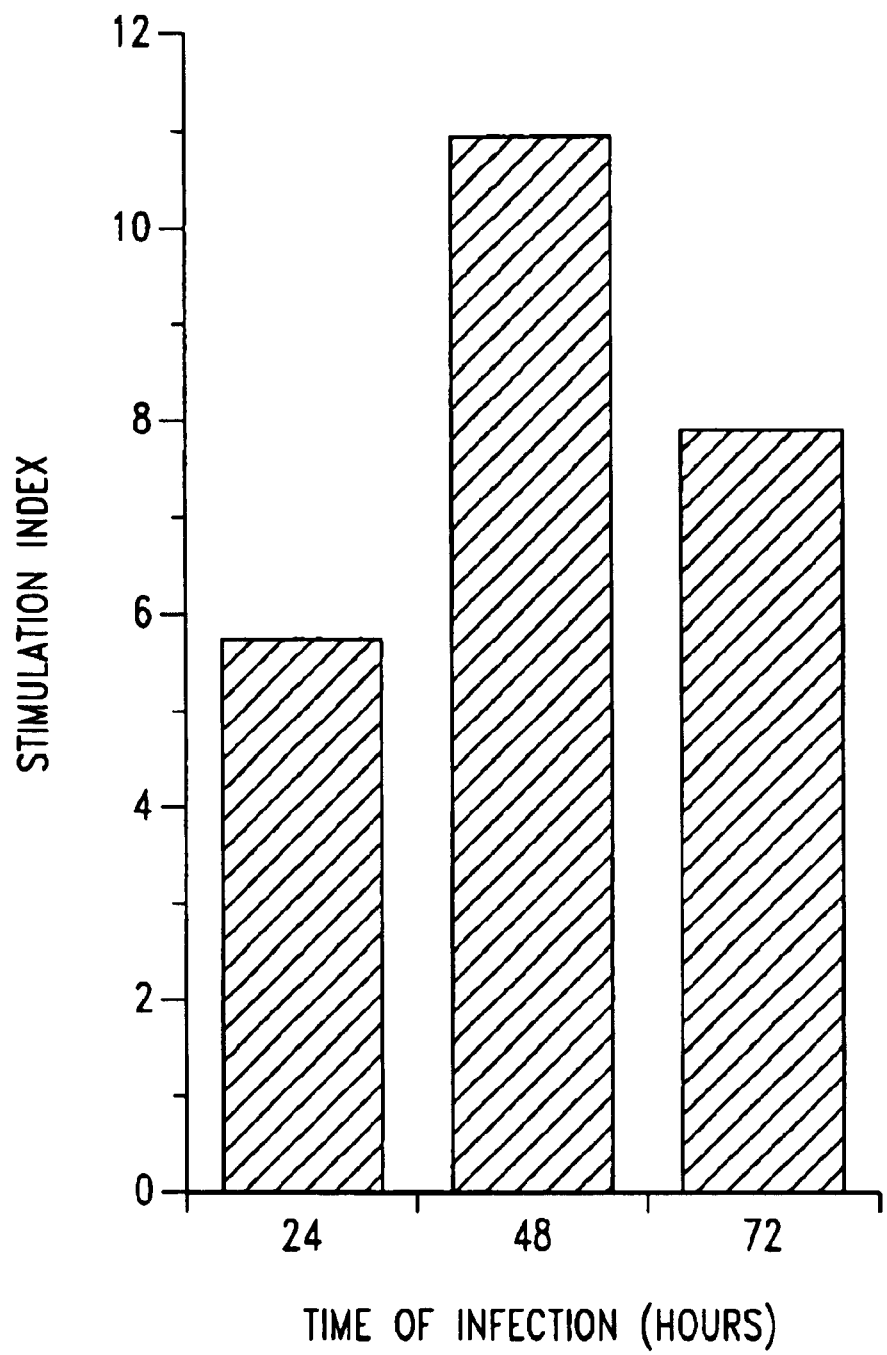
FIG. 1 shows the stimulation of proliferation of T-cells obtained from *L. donovani*-immunized BALB/c mice (represented by stimulation index) by *L. donovani*-infected macrophages after incubation for 24, 48 and 72 hours.

As noted above, the present invention is generally directed to compositions and methods for preventing, treating and detecting leishmaniasis, as well as for stimulating immune responses in patients. The compositions of the subject invention include polypeptides that comprise at least an immunogenic portion of a Leishmania antigen, or a variant of such an antigen that differs only in conservative substitutions and/or modifications. In one preferred embodiment, compositions of the present invention include multiple polypeptides selected so as to provide enhanced protection against a variety of Leishmania species.

Polypeptides within the scope of the present invention include, but are not limited to, polypeptides comprising immunogenic portions of Leishmania antigens comprising the sequences recited in SEQ ID NO:2 (referred to herein as MIS), SEQ ID NO:4 (referred to herein as Ldp23), SEQ ID NO:6 (referred to herein as Lbhsp83), SEQ ID NO:8 (referred to herein as Lt-210), SEQ ID NO:10 (referred to herein as LbeIF4A), SEQ ID NO: 20 (referred to herein as Lmspla), SEQ ID NO: 22_(referred to herein as Lmsp9a) and SEQ ID NOs: 24 and 26 (referred to herein as MAPS-1A). As used herein, the term "polypeptide" encompasses amino acid chains of any length, including full length proteins (i.e., antigens), wherein the amino acid residues are linked by covalent bonds. Thus, a polypeptide comprising an immunogenic portion of one of the above antigens may consist entirely of the immunogenic portion, or may contain additional sequences. The additional sequences may be derived from the native Leishmania antigen or may be heterologous, and such sequences may (but need not) be immunogenic. An antigen "having" a particular sequence is an antigen that contains, within its full length sequence, the recited sequence. The native antigen may, or may not, contain additional amino acid sequence.

An immunogenic portion of a Leishmania antigen is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/ or B cells). In particular, immunogenic portions are capable of inducing T-cell proliferation and/or a dominantly Th1-type cytokine response (e.g., IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

The compositions and methods of the present invention also encompass variants of the above polypeptides. A "variant," as used herein, is a polypeptide that differs from the native antigen only in conservative substitutions and/or modifications, such that the ability of the polypeptide to induce an immune response is retained. Such variants may generally be identified by modifying one of the above polypeptide sequences and evaluating the immunogenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

"Polypeptides" as described herein also include combination polypeptides. A "combination polypeptide" is a polypeptide comprising at least one of the above immunogenic portions and one or more additional immunogenic Leishmania sequences, which are joined via a peptide linkage into a single amino acid chain. The sequences may be joined directly (i.e., with no intervening amino acids) or may be joined by way of a linker sequence (e.g., Gly—Cys— Gly) that does not significantly diminish the immunogenic properties of the component polypeptides.

In general, Leishmania antigens having immunogenic properties, and DNA sequences encoding such antigens, may be prepared using any of a variety of procedures from one or more Leishmania species including, but not limited to, *L. donovani, L. chagasi, L. infantum, L. major, L. amazonensis, L. braziliensis, L. panamensis, L. mexicana, L. tropica*, and *L. guyanensis*. Such species are available, for example, from the American Type Culture Collection (ATCC), Rockville, Md. For example, peptides isolated from MHC class II molecules of macrophages infected with a Leishmania species may be used to rescue the corresponding Leishmania donor antigens. MHC class II molecules are expressed mainly by cells of the immune system, including macrophages. These molecules present peptides, which are usually 13–17 amino acids long, derived from foreign antigens that are degraded in cellular vesicles. The bound peptide antigens are then recognized by CD4 T-cells. Accordingly, foreign peptides isolated from MHC class II molecules of, for example, Leishmania-infected murine macrophages may be used to identify immunogenic Leishmania proteins.

Briefly, peptides derived from Leishmania antigens may be isolated by comparing the reverse phase HPLC profile of peptides extracted from infected macrophages with the profile of peptides extracted from uninfected cells. Peptides giving rise to distinct HPLC peaks unique to infected macrophages may then be sequenced using, for example, Edman chemistry as described in Edman and Berg, *Eur J. Biochem*, 80:116–132 (1967). A DNA fragment corresponding to a portion of a Leishmania gene encoding the peptide may then be amplified from a Leishmania cDNA library using an oligonucleotide sense primer derived from the peptide sequence and an oligo dT antisense primer. The resulting DNA fragment may then be used as a probe to screen a Leishmania library for a full length cDNA or genomic clone that encodes the Leishmania antigen. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y. (1989).

This approach may be used to identify a 23 kD Leishmania donovani antigen (referred to herein as Ldp23). The sequence of a DNA molecule encoding Ldp23 is provided in SEQ ID NO:3 and the amino acid sequence of Ldp23 is provided in SEQ ID NO:4. Using the methods described herein, Ldp23 has been shown to induce a Th1 immune response in T-cells prepared from Leishmania-infected mice.

Alternatively, a Leishmania cDNA or genomic expression library may be screened with serum from a Leishmania-infected individual, using techniques well known to those of ordinary skill in the art. DNA molecules encoding reactive antigens may then be used to express the recombinant antigen for purification. The immunogenic properties of the purified Leishmania antigens may then be evaluated using, for example the representative methods described herein.

For example, sera from Leishmania-infected mice may be used to screen a cDNA library prepared from Leishmania amastigotes. Reactive clones may then be expressed and recombinant proteins assayed for the ability to stimulate T-cells or NK cells derived from Leishmania-immune individuals (i.e., individuals having evidence of infection, as documented by positive serological reactivity with Leishmania-specific antibodies and/or a Leishmania-specific DTH response, without clinical symptoms of leishmaniasis). This procedure may be used to obtain a recombinant DNA molecule encoding the Leishmania antigen designated M15. The sequence of such a DNA molecule is provided in SEQ ID NO:1, and the amino acid sequence of the encoded protein is provided in SEQ ID NO:2.

A similar approach may be used to isolate a genomic DNA molecule encoding an immunogenic Leishmania braziliensis antigen, referred to herein as Lbhsp83. More specifically, a genomic clone encoding Lbhsp83 may be isolated by screening a *L. braziliensis* expression library with sera from a Leishmania-infected individual. The DNA encoding Lbhsp83 is homologous to the gene encoding the eukaryotic 83 kD heat shock protein. The sequence of a DNA molecule encoding nearly all of Lbhsp83 is presented in SEQ ID NO:5, and the encoded amino acid sequence is provided in SEQ ID NO:6. Using the methods described below, Lbhsp83 has been found to stimulate proliferation, and a mixed Th1 and Th2 cytokine profile, in PBMC isolated from *L. braziliensis*-infected patients. Accordingly, Lbhsp83 is an immunogenic Leishmania antigen. Regions of Lbhsp83 that are not conserved with the mammalian gene have been found to be particularly potent for T-cell stimulation and antibody binding. Such regions may be identified, for example, by visual inspection of the sequence comparison provided in FIG. 19.

This approach may also be used to isolate a DNA molecule encoding a 210 kD immunogenic *L. tropica* antigen, referred to herein as Lt-210. The preparation and characterization of Lt-210, and immunogenic portions thereof (such as Lt-1 and immunogenic repeat and non-repeat sequences), is described in detail in U.S. patent application Ser. No. 08/511,872, filed Aug. 4, 1995. The sequence of a DNA molecule encoding Lt-1 is provided in SEQ ID NO:7 and the encoded amino acid sequence is presented in SEQ ID NO:8.

The above approach may further be used to isolate a DNA molecule encoding a *L. braziliensis* antigen referred to herein as LbeIF4A. Briefly, such a clone may be isolated by screening a *L. braziliensis* expression library with sera obtained from a patient afflicted with mucosal leishmaniasis, and analyzing the reactive antigens for the ability to stimulate proliferative responses and preferential Th1 cytokine production in PBMC isolated from Leishmania-infected patients, as described below. The preparation and characterization of LbeIF4A is described in detail in U.S. patent application Ser. Nos. 08/454,036 and 08/488,386, which are continuations-in-part of U.S. patent application Ser. No. 08/232,534, filed Apr. 22, 1994. The sequence of a DNA molecule encoding LbeIF4A is provided in SEQ ID NO:9 and the encoded amino acid sequence is presented in SEQ ID-NO:10. Homologs of LbeIF4A, such as that found in *L. major*, may also be isolated using this approach, and are within the scope of the present invention.

Compositions of the present invention may also, or alternatively, contain soluble Leishmania antigens. As used herein, "soluble Leishmania antigens" refers to a mixture of at least 8 different Leishmania antigens that may be isolated from the supernatant of Leishmania promastigotes of any species grown for 8–12 hours in protein-free medium. Briefly, the organisms are grown to late log phase in complex medium with serum until they reach a density of $2-3 \times 10^7$ viable organisms per mL of medium. The organisms are thoroughly washed to remove medium components and resuspended at $2-3 \times 10^7$ viable organisms per mL of defined serum-free medium consisting of equal parts RPMI 1640 and medium 199, both from Gibco BRL, Gaithersburg, Md. After 8–12 hours, the supernatant containing soluble Leishmania antigens is removed, concentrated 10 fold and dialyzed against phosphate-buffered saline for 24 hours. The presence of at least eight different antigens within the mixture I 0 of Leishmania antigens may be confirmed using SDS-PAGE (i.e., through the observation of at least 8 different bands). The immunogenic properties of the soluble Leishmania antigens may be confirmed by evaluating the ability of the preparation to elicit an immune response in cultures of lymph node cells and/or peripheral blood mononuclear cells (PBMC) isolated from presently or previously Leishmania-infected individuals. Such an evaluation may be performed as described below.

Individual antigens present within the mixture of soluble Leishmania antigens may be isolated by immunizing mice or rabbits with *L. major* culture supernatant, containing soluble antigens, and employing the resultant sera to screen an *L. major* cDNA expression library as described in detail below. This procedure may be used to isolate recombinant DNA molecules encoding the *L. major* antigens referred to herein as Lmspla, Lmsp9a and MAPS-1A. DNA sequences encoding Lmsp1a, Lmsp9a and MAPS-1A are provided in SEQ ID NO: 19, 21 and 23, respectively, with the corresponding predicted amino acid sequences being presented in SEQ ID NO: 20, 22 and 24, respectively. The immunogenic properties of the isolated soluble Leishmania antigens may be evaluated using, for example, the representative methods described herein.

Regardless of the method of preparation, the antigens described herein are immunogenic. In other words, the antigens (and immunogenic portions thereof) are capable of eliciting an immune response in cultures of lymph node cells and/or peripheral blood mononuclear cells (PBMC) isolated from presently or previously Leishmania-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously Leishmania-infected individuals. A Leishmania-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with Leishmania lysate or a positive serological test. Asymptomatic individuals are infected individuals who have no signs or symptoms of the disease. Such individuals can be identified based on a positive serological test and/or skin test with Leishmania lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with Leishmania promastigotes emulsified in complete Freuind's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a polypeptide (e.g., a Leishmania antigen or a portion or other variant thereof) to induce a response in PBMC or lymph node cell cultures may be evaluated by contacting the cells with the polypeptide and measuring a suitable response. In general, the amount of polypeptide that is sufficient for the evaluation of about $2\times10^5$ cells ranges from about 10 ng to about 100 μg, and preferably is about 1–10 μg. The incubation of polypeptide with cells is typically performed at 37° C. for bout 1–3 days. Following incubation with polypeptide, the cells are assayed for an ppropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the change in the level of MRNA encoding one or more specific cytokines. In particular, the secretion of interferon-y, interleukin-2, tumor necrosis factor-α and/or interleukin-12 is indicative of a Th1 response, which is responsible for the protective effect against Leishmania. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1–3\times10^5$ cells, the production of 30 pg/mL of IL-12, IL-4, IFN-γ, TNF-α or IL-12 p40, or 10 pg/mnL of IL-12 p70, is considered able to stimulate production of a cytokine.

Immunogenic portions of the antigens described herein may be prepared and identified using well known techniques, such as those summarized in Paul, Fundamental Immunology, 3rd ed., 243–247 (Raven Press, 1993) and references cited therein. Such techniques include screening polypeptides derived from the native antigen for immunogenic properties using, for example, the representative techniques described herein. An immunogenic portion of a polypeptide is a portion that, within such representative assays, generates an immune response (e.g., proliferation and/or cytokine production) that is substantially similar to that generated by the full length antigen. In other words, an immunogenic portion of an antigen may generate at least about 25%, and preferably at least about 50%, of the response generated by the full length antigen in the model assays described herein.

Portions and other variants of immunogenic Leishmania antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystemsDivision, Foster City, Calif., and may be operated according to the manufacturer's instructions.

Recombinant polypeptides containing portions and/or variants of a native antigen may be readily prepared from a DNA sequence encoding the antigen. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purif a recombinant protein.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In certain aspects of the present invention, described in detail below, the polypeptides and/or soluble Leishmania antigens may be incorporated into pharmaceutical compositions or vaccines. Pharmaceutical compositions comprise one or more polypeptides, each of which may contain one or more of the above sequences (or variants thereof), and a physiologically acceptable carrier. Vaccines comprise one or more of the above polypeptides and a non-specific immune response enhancer, such as an adjuvant (e.g., LbeIF4A, interleukin-12 or other cytokines) or a liposome (into which the polypeptide is incorporated). Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other Leishmania antigens, either incorporated into a combination polypeptide or present within one or more separate polypeptides.

Alternatively, a pharmaceutical composition or vaccine may contain DNA encoding one or more of the polypeptides as described above, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordella pertussis* or *Mycobacterium tuberculosis*. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Preferred adjuvants include LbeIF4A, IL-12 and other cytokines such as IFN-$\gamma$ or granulocyte-macrophage colony stimulating factor (GM-CSF). By virtue of its ability to induce an exclusive Th1 immune response, the use of LbeIF4A, and variants thereof, as an adjuvant in the vaccines of the present invention is particularly preferred.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by individual polypeptides may be additive, (2) stimulation of proliferation and/or cytokine production by individual polypeptides may be synergistic, (3) individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M15, Ldp23, Lbhsp83, Lt-1 and LbeIF4A. Alternatively, or in addition, the combination may include one or more polypeptides comprising immunogenic portions of Lmspla, Lmsp9a and MAPS-1A, and/or soluble Leishmania antigens.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical compositions and vaccines described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-γ, as well as tumor necrosis factor-α). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of LbeIF4A (or a variant thereof), M15, soluble Leishmania antigens, Lmspla, Lmsp9a, MAPS-1A and/or Ldp23 (or a variant thereof). Polypeptides comprising an immunogenic portion of Lbhsp83 and/or Lt-1 may also be used, in combination with a polypeptide that contains at least an immunogenic portion of LbeIF4A. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1, LbeIF4A, Lmsp1a, Lmsp9a, and MAPS-1A. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1 and LbeIF4A, Lmsp1a, Lmsp9a, and MAPS-1A. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (ie., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1–2 years. In general, the amount of polypeptide present in a dose (or produced in situ by the DNA in a dose) ranges from about 100 ng to about 1mg per kg of host, typically from about 10 μg to about 100 μg. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 μg to 100 μg, preferably from about 10 μg to 50 μg in a volume of 0.1 mL. Preferably, the carrier employed in such pharmaceutical compositions is a saline solution with appropriate preservatives, such as phenol and/or Tween 801™.

The following Examples are offered by way of illustration and not by way of limitation.

EXAMPLES

Example 1

Preparation of M15

This Example illustrates the preparation of a Leishmania antigen M15, having the sequence provided in SEQ ID NO:2.

An *L. major* (Friedlan strain) amastigote cDNA expression library prepared in the γZAP II vector (Stratagene, La Jolla, Calif.) was screened according to manufacturer's instructions using sera obtained from *L. major* infected BALB/c mice (8 weeks post inoculation). Approximately 40,000 plaques were screened and four clones expressing reactive antigens were purified to homogeneity by two subsequent rounds of low density screening. Bluescript phagemid inserts were excised from positive clones for further analysis. An EcoRI/SstII restriction fragment from the 5' end of one partial cDNA insert isolated during first round screening (pLma1—1) was subsequently used as a probe to rescreen for clones containing full length cDNA inserts. The probe was labeled to high specific activity ($\square 10^9$ cpm/μg) with [→-$^{32}$P]dCTP using the random primer method and was used to screen $\square$10,000 plaques of the *L. major* expression library described above. Positive clones were compared by restriction enzyme digestion and the clone with the largest insert (pfl1-1) was chosen for subsequent analysis.

DNA sequence analyses were performed on an Applied Biosystems automated sequencer using Taq polymerase and dye coupled ddNTP terminators or dye-labeled sequencing primers. The complete sequence of the 2685 bp insert was determined using a combination of primer-directed sequencing and by sequencing a series of overlapping Exonuclease III deletion subclones generated using the Erase-a-base system (Promega, Madison, Wis.). The sequence of this insert is provided in SEQ ID NO:1, and the deduced amino acid sequence is provided in SEQ ID NO:2.

The complete insert of clone pfl-1 was excised by digestion with BamHI/KpnI and was subcloned in frame into BamHI/Kpnl digested pQE31 (QUIAGEN) to generate the construct pM 151 A. *E. coli* containing this construct inducibly expressed high levels of the *L. major* antigen encoded by pfl1-1 (designated as M15) with the addition of a 6-histidine tag at the amino terminus. Large volume cultures (500 ml) of *E. coli* host cells containing the pM 151 A construct were induced to express recombinant protein by the addition of 2mM IPTG at mid-log phase of growth. Growth was continued for 4 to 5 hours and bacteria were then pelleted and washed once with cold PBS. Bacteria were resuspended in 20 ml of lysis buffer (50 mM $Na_2HPO_4$, pH 8.0, 300 mM NaCl, 10 mM μ-mercaptoethanol) containing 20 mg of lysozyme and were lysed by a 1 hour incubation at 4° C. followed by brief sonication. Insoluble material was removed by centrifugation at 10,000×g for 10 minutes and although the recombinant protein was found to be evenly distributed between the soluble and insoluble fractions the insoluble material was discarded at this point. Recombinant protein containing the amino terminal histidine tag was affinity purified using Ni-NTA resin (QIAGEN) according to the manufacturer's recommendations. Briefly, 8 ml of Ni-NTA resin resuspended in lysis buffer was added to the soluble lysate fraction and binding was conducted with constant mixing for 1 hour at 4° C. The mixture was then loaded into a gravity flow column and the non-binding material was allowed to flow through. The Ni-NTA matrix was washed 3 times with 25 ml of wash buffer (50 mM $Na_2HPO_4$, pH 6.0, 300 mM NaCl, 10 mM β-mercaptoethanol) and bound material was eluted in 25 ml of elution buffer (50 mM $Na_2HPO_4$, pH 5.0, 300 mM NaCl, 10mM β-mercaptoethanol). The eluted material was then dialyzed against 3 changes of PBS, sterile filtered and stored at −20° C. The purified recombinant protein was shown by SDS-PAGE analysis to be free of any significant amount of *E. coli* protein. A small number of bands of lower molecular weight were assumed to be proteolytic products of the *L. major* antigen based on their reactivity by western blot analysis. A high titre polyclonal antisera against M15 was generated in rabbits by repeated subcutaneous injection of recombinant protein. Western blot analysis of lysates from *L. major* promastigotes and amastigotes using this antisera indicated that the protein is constitutively expressed throughout the parasite lifecycle.

Example 2

Preparation of LDP23

This Example illustrates the preparation of a Leishmania antigen Ldp23, having the sequence provided in SEQ ID NO:4.

A. Purification of MHC Class II-associated Peptides from P388D1 Macrophayes Infected with *L. donovani*

To ascertain that in vitro infection of macrophages would load their MHC class II molecules with parasite peptides, initial experiments were carried out to test the ability of *L. donovani*-infected macrophage cell line P388D1 to present parasite antigens to *L. donovani* specific T-cells. This macrophage cell line was chosen because it has the same H-2 haplotype as the BALB/c mouse, which is a strain of mouse moderately susceptible to *L. donovani* infection and selected to conduct the in vivo experiments. Using a proportion of 3–5 parasites per cell and an initial incubation at room temperature for 4–6 hours follows by 37° C. for 24–48 hours, close to 90% of the macrophages were infected. The level of MHC class II molecule expression, as determined by FACS analysis, indicated that infection did not cause an effect on the levels of MHC class II expression when compared to non-infected control cells.

To test the ability of the *L. donovani*-infected P388D1 cells to present parasite antigens, macrophages were infected as indicated above and incubated at 26° C. for 6 hours, and then as 37° C. for either 24, 48 or 72 hours. At each of these time points the non-adherent cells and free parasites were washed out and the adherent cells were mechanically dislodged, washed and fixed with paraformaldehyde. These cells were then used as antigen presenting cells (APCs) for purified lymph node T-cells from BALB/c mice immunized with *L. donovani* promastigotes. To generate these anti-*L. donovani* specific T-cells, BALB/c mice (H-$2^d$) of both sexes (The Jackson Laboratory, Bar Harbor, Me.) were immunized at 8 to 14 weeks of age in the rear foot pad with 5–10×10$^6$ *L. donovani* promastigotes emulsified in complete Freünd's adjuvant (CFA) (Difco Laboratories, Madison, Mich.) as described in Rodrigues et al., Parasite Immunol. 14:49 (1992). The draining lymph nodes were excised 8 days after the immunization and T-cells were purified in an anti-mouse Ig column to remove the B cells, as described in Bunn-Moreno and Campos-Neto, *J. Immunol.* 127:427 (1981), followed by a passage through a Sephadex G10 column to remove the macrophages.

Stimulation index was calculated by dividing the cpm obtained for the cells cultured in the presence of infected P388D1 macrophages by the cpm obtained for the cells cultured in the presence of non-infected macrophages, but subjected to the same conditions as the infected macrophages. The results shown FIG. 1 indicate that *L. donovani*-infected P388D1 macrophage process parasite antigens and that optimal presentation occurs after 48 hours of infection. No stimulation of the T-cells by the non-infected macrophages was observed.

To isolate the MHC class II associated *L. donovani* peptides, P388D1 macrophages were infected with *L. donovani* promastigotes for an initial incubation of 6 hours at room temperature. The cultures were then transferred to 37° C. for the remainder of the 48 hour incubation period. At a ratio of 3–5 parasites per macrophage nearly 90% of the macrophages were infected after 24 hours of incubation at 37° C.

The MHC class II molecules were then affinity-purified. Approximately 1.5×10$^{10}$ *L. donovani*-infected or an equal number of non-infected P388D1 macrophages were used for each purification. The cells were harvested, washed with PBS and incubated for 30 minutes in cold lysis buffer (PBS, 1% Nonidet P40, 25mM iodoacetamide, 0.04% sodium azide, 1mM aprotinin and 1mM PMSF). The insoluble material was removed by centrifugation at 40,000g for 1 hour and the supernatant was recycled overnight at 4° C. over a 5 ml anti-MHC class II molecules (H-2$^d$) Sepharose column (Protein G Sepharose column to which the monoclonal antibody MK-D6 has been bound). Culture supernatants of MK-D6 hybridoma cells (American Type Culture Collection, Rockville, Md.) were employed as the source for anti-MHC class II (H-2$^d$) monoclonal antibody. The column was washed with 50 ml of lysis buffer and then with 50 ml of PBS containing 0.5% octyl glucopyranoside detergent. Bound molecules were eluted from the column with 1 M acetic acid in 0.2% NaCl. The MHC/peptide molecules were separated from the IgG (MK-D6 monoclonal antibody) using a Centricon 100 filter unit (Amicon Division, W. R. Grace & Co., Beverly, Mass.). The peptides were then dissociated from the class II molecules by the addition of acetic acid to 2.5M, followed by separation using a Centricon 10 filter unit. The resulting peptide preparation, present in the low molecular weight sample, was then dried using a speed vac concentrator (Savant Instrument Inc., Farmingdale, N.Y.).

The peptides were redissolved in 200 µl of 0.05% TFA and separated by reverse-phase high performance liquid chromatography (RP-HPLC) using a 2.1mm×25cm Vydac C-18 colunm at a flow rate of 0.15 ml/min employing a 1 to 30% acetonitrile gradient (60 min) followed by a 30 to 60% gradient (30 min) and then a 60 to 80% gradient (90–110 min). Non-infected P388D1 cells were similarly processed to serve as background control for endogenous MHC class II associated peptides. FIG. 2 shows a representative experiment; four distinct peaks which are present only in the material isolated from infected macrophages (panel B), and not in the material isolated from uninfected macrophages (panel A) are indicated.

Out of three independent peptide extractions, twenty five distinct HPLC peptide peaks were isolated from *L. donovani*-infected macrophages and were subjected to protein sequence analysis using automated Edman degradation on an Applied Biosystems 477 gas-phase protein sequencer. Protein sequence and amino acid analysis were performed by the W. M. Keck Foundation, Biotechnology Resource Laboratory, Yale University, New Haven, Conn. In practically all determinations, no assignment could be made for the first position. Also, in most cases the definition of the amino acid residues of the 10–15 positions was based on the quantitative dominance of one residue over others. Using this approach, the sequences obtained for several peptides showed the presence of 3–6 different residues in many of the 10–15 sequence cycles analyzed for each determination, reflecting a mixture of peptides. In addition, sequences could not be obtained for some peaks because the peptides were blocked. Notwithstanding, three peptides sequences were determined. Amino-acid sequences were searched for identity with proteins in the GenBank database using the GENPETP, PIR and SWISSPROT programs. The sequence data base analysis revealed that one of the peptides was highly homologous to glyceraldehyde-3-phosphate dehydrogenase of various species. Another peptide had homology with elongation factor of several species, including Leishmania. The third sequence was not clearly related to any known proteins, and is shown below: XQXPQ(L/K)VFDEXX.

B. Cloning and Sequencing of the Ldp23 Gene

In order to retrieve the *L. donovani* protein that was processed into a peptide associated with the MHC class II molecules of infected macrophages, the peptide sequence of uncertain origin was chosen to guide the strategy for cloning the corresponding parasite gene. A DNA fragment was initially amplified from *L. donovani* promastigote cDNA by PCR. The sense primer was a peptide derived oligonucleotide (5'>GGAATTCCCCInCAGCTInGTInTTCGAC<3') containing an EcoRI restriction endonuclease site (underlined). The bases were selected following the preferential codon usage of *L. donovani*, as described in Langford et al., *Exp. Parasitol.* 74:360 (1992). Inosine was used for the residues of positions 4, 6 and 7 because of the low codon usage assurance for the corresponding amino acids. In addition, the carboxyl-terminal L-glutamic acid was not included for the design of the primer. The antisense primer was a poly-thymidine oligonucleotide (oligo dT, downstream primer) containing a XhoI restriction endonuclease site.

The gene fragment was amplified from a *L. donovani* promastigote cDNA preparation using the following reaction conditions: one cycle of 3 min at 94° C. immediately followed by 35 cycles of 1 min at 94° C., 1 min at 45° C. and 1 min at 72° C. The *L. donovani* cDNA was prepared from 5×10$^7$ washed promastigote forms harvested at the log growth phase (3 days culture). The cDNA was obtained using an Invitrogen cDNA cycle™ kit (Invitrogen Co., San Diego, Calif.). Oligonucleotide primers were synthesized by the DNA Synthesis Laboratory, Department of Pathology, Yale University School of Medicine.

The PCR products were analyzed by gel electrophoresis. Only one band of approximately 300 bp was obtained. This fragment was cloned and its sequence confirmed the sequence of the peptide-based primer including the glutamic acid codon, deliberately not included in the primer sequence.

The PCR amplified gene fragment was ligated into the pCR™ vector using the TA cloning system (Invitrogen Co., San Diego, Calif.). Transformants were selected in LB medium containing 100 µg/ml ampicillin and the plasmid DNA was isolated using the Wizard™ Minipreps DNA purification kit (Promega Co., Madison, Wis.). Insert DNA was released with the restriction enzymes EcoRi and XhoI (New England Biolabs, Beverly, Mass.), purified from an agarose gel electrophoresis and labeled with $^{32}$P using a random priming method (Megaprime Labeling Kit, Amersham Life Science, Buckinghamshire, England).

This DNA fragment was used as probe to screen a *L. donovani* promastigote cDNA library as described in Skeiky et al., *Infect. Immun.* 62:1643 (1994). An approximately 650 bp cDNA (Ldp23) was excised from the phagemid by in vivo excision using the Stratagene protocol. DNA sequencing was performed using the Sequenase version 2 system (DNA sequencing kit) in the presence or absence of 7-deaza-GTP (United States Biochemical, Cleveland, Ohio). The sequence is provided as SEQ ID NO:3, and shows complete homology with the original 300 bp PCR fragment. A 525 bp open reading frame containing an ATG codon that follows the last 4 bases of the spliced leader sequence and 3 stop codons adjacent to the poly A tail was identified. This frame also codes the carboxyl terminal sequence (KVFDE) of the purified MHC class II associated peptide. The sequence analysis of the deduced protein sequence revealed one potential glycosylation site (Asn-Cys-Ser) at positions 68–70.

Sequence analysis was performed using the University of Wisconsin Genetics Computer Group Programs and the GenBank and EMBL data bases of protein and DNA sequences. The search for homology of the Ldp23 gene with known sequences revealed no significant homology.

C. Bacterial Expression and Purification of Recombinant Protein

The recombinant L. donovani peptide donor protein was produced in E. coli transformed with the pGEX 2T expression vector in which the Ldp23 gene was subcloned in frame. PCR was used to subclone the cloned gene in frame into the expression vector pGEX 2T. Primers containing the appropriate restriction site enzymes, initiation and termination codons were: 5'>GGATCCATGGTCAAGTCCCA CTACATCTGC<3' for the upstream primer and 5'>GAAT-TCAGACCGGATAGAAA TAAGCCAATGAAA<3' for the downstream primer (restriction sites of BamHI and EcoRI are underlined respectively). PCR conditions were as indicated above for the amplification of the original peptide related DNA fragment. The template used was pBluescript plasmid containing the cloned gene from the cDNA library.

Overexpression of the recombinant fusion protein was accomplished by growing the transformed E. coli (DH5α) and inducing the tac promoter with 1 mM isopropyl-β-thiogalactopyranoside (IPTG) (Stratagene, La Jolla, Calif.). Cells were collected, centrifuged, and analyzed for the presence of the fusion protein by SDS-PAGE. A glutathione-S-transferase fusion protein of 43–44 kD was produced, indicating a leishmanial protein of approximately 18 kD, as glutathione-S-transferase (GST) has a MW of 26 kD. However, the fusion protein was very insoluble and therefore could not be purified by affinity chromatography using a glutathione column. The use of low concentrations of detergents like SDS, sarcosyl, deoxycolate, and octyl-glucopyranoside during the extraction steps was efficient to solubilize the protein but unfortunately prevented its binding to the glutathione column. Other maneuvers, such as the growth of the E. coli and incubation and induction of the tac promoter with IPTG at 33° C., did not improve the protein solubility. However, the purification was achieved by preparative SDS-PAGE. The band was visualized with 0.1M KCl, cut and electroeluted from the gel followed by extensive dialysis against PBS and concentration on Centricon 10 filters.

Figure 3A:
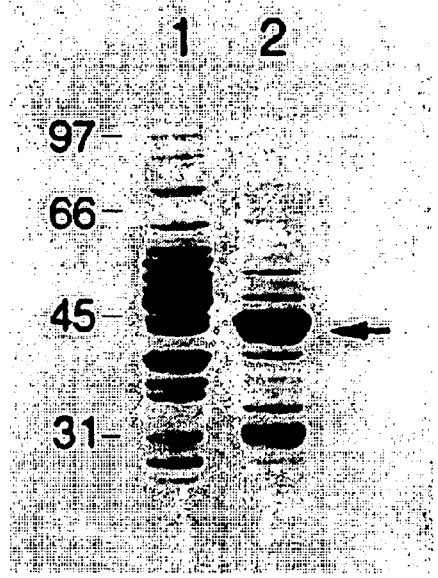
FIG. 3 illustrates the expression and purification of the Leishmania antigen Ldp23 as a recombinant fusion protein. Panel A shows a Coomassie blue-stained SDS-PAGE gel of lysed *E. coli* without (lane 1) and with (lane 2) IPTG induction of Ldp23 expression. Arrow indicates the recombinant fusion protein. Panel B shows the fusion protein following excision from a preparative SDS-PAGE gel, electroelution, dialysis against PBS and analytical SDS-PAGE.
Figure 3B:
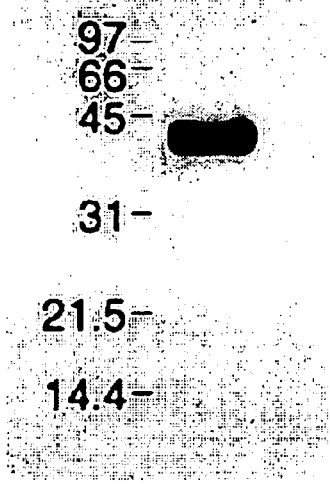

Approximately 500 µg of purified protein was obtained. The purified protein is shown in FIG. 3. In panel A, E. coli (DH5α) transformed with the expression vector pGEX 2T containing the Ldp23 gene was grown in LB medium and the tac promoter was induced with IPTG for 3 hours. The cells were pelleted, resuspended in loading buffer and submitted to SDS-PAGE (10%) under reducing condition. The gel was stained with Coomassie blue. Lane 1 shows the uninduced E. coli and land 2 shows the induced E. coli. The arrow indicates the recombinant protein. Panel B shows the protein prepared as in panel A and submitted to a preparative SDS-PAGE. The band corresponding to the overexpressed recombinant fusion protein was identified by KCl, cut out, electroeluted from the gel strip, dialyzed against PBS and submitted to analytical SDS-PAGE (12%). Numbers on the left side indicate the molecular weights of the markers. Attempts to further purify the leishmanial protein by cleaving it out from the fusion protein GST with thrombin were unsuccessful.

D. Expression of Ldp23

To ascertain that the Ldp23 peptide is expressed in Leishmania organisms, a Northern blot analysis was performed using RNA prepared from different promastigote growth phases (logarithmic and stationary) and from the amastigote form of these parasites.

The RNA was prepared from $2 \times 10^7$ parasite cells using the Micro RNA isolation kit (Stratagene, La Jolla, Calif.) according to the company's recommended instructions. RNA was prepared from L. donovani promastigotes (logarithmic growth phase); from L. major promastigotes (logarithmic and stationary growth phases); from L. amazonensis, both promastigotes (logarithmic and stationary growth phases) and amastigotes purified from CBA/J infected mice; and from L. pifanoi, both promastigotes (logarithmic and stationary growth phases) and amastigotes (from axenic culture medium). L. donovani (IS strain), L. amazonensis (MHOM/BR/77/LTB0016), L. major (MHOM/IR/79/LRC-L251) and L. pifanoi (MHOMJVE/60/Ltrod) promastigotes were grown and maintained at 26° C. in Schneider's medium containing 20% FCS and 50 µg/ml gentamicin. The amastigote forms of L. amazonensis were obtained by differential centrifugation of a "pus-like" foot pad lesion of a CBA/J mouse infected for 6 months with this parasite. L. pifanoi amastigotes were obtained from axenic culture as previously reported by Pan et al., J. Euk. Microbiol. 40:213 (1993).

The hybridization was carried out at 45° C. in the presence of 50% formamide, 5× Denhardt's solution, 0.1% SDS, 100 µg/ml single stranded salmon sperm DNA and 5× SSPE using 0.45 µm Nytran membrane filters (Schleicher & Schuell, Keene, N.H.). The probe was the $^{32}$P labeled Ldp23 gene.

Figure 4:
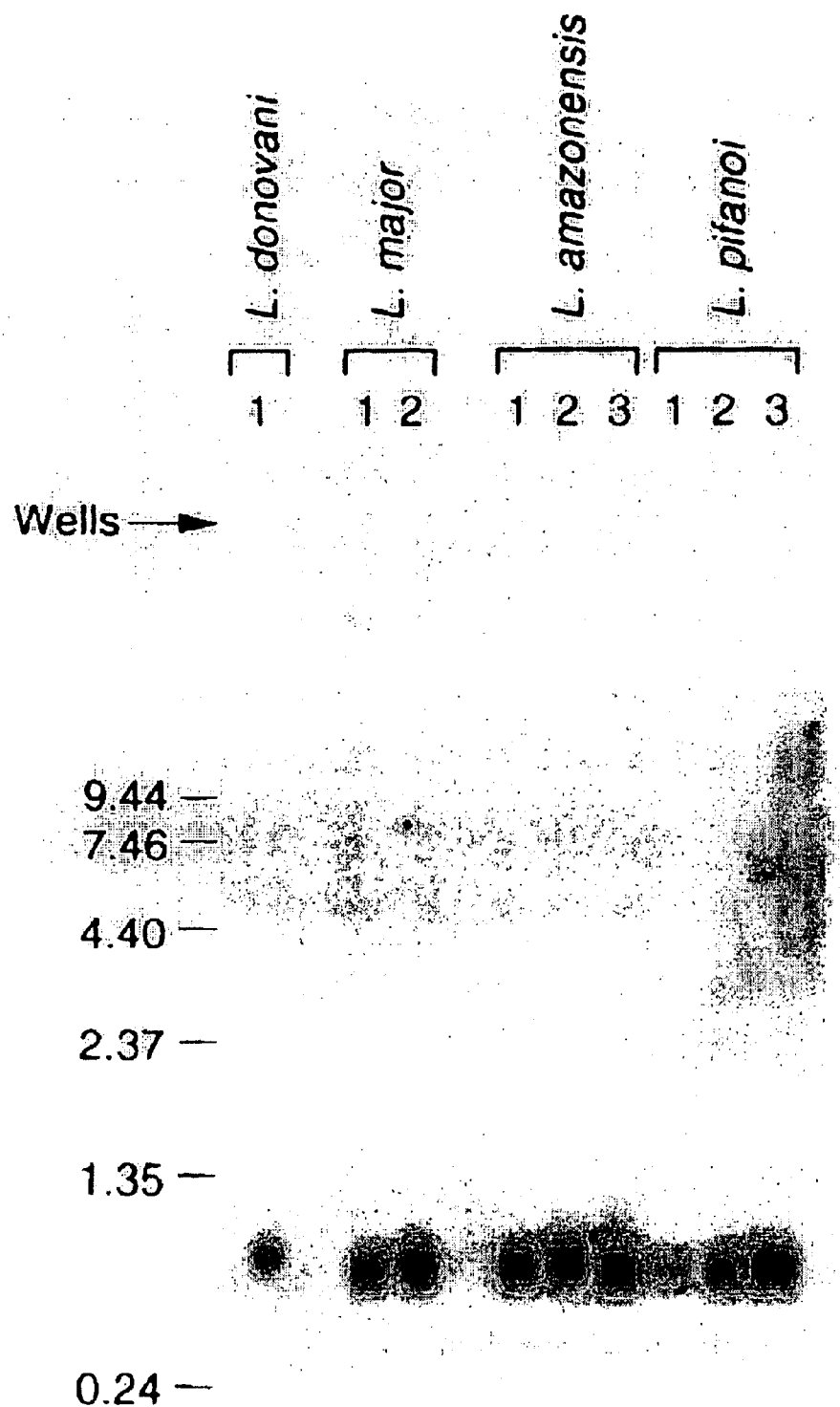
FIG. 4 presents a Northern blot analysis of total RNA prepared from *L. donovani, L. major, L. amazonensis* and *L. pifanoi* with a $^{32}P$ labeled Ldp23 gene. 1, 2 and 3 refer to RNA obtained from promastigotes at the logarithmic growth phase, promastigotes at the stationary growth phase and amastigote forms, respectively.

FIG. 4 shows that one single RNA band of 680 bp was observed for all growth phases and forms of all tested Leishmania. Within FIG. 4, the numbers 1, 2 and 3 refer to RNA obtained from promastigotes at the logarithmic growth phase, promastigotes at the stationary growth phase and amastigote forms, respectively, and the numbers on the left side indicate the molecular weights of the markers in base pairs. This result is consistent with the corresponding gene size (525 bp) and with the molecular weight of the expressed protein and points to the ubiquitous distribution and expression of this gene within the genus Leishmania.

E. Induction of Anti-L. donovani Antibody Response in Mice and Rabbits by Purified Recombinant Protein In order to evaluate the immunogenicity of the recombinant leishmanial protein, and to investigate its expression in the parasites, mice and rabbits were immunized with the GST-fusion protein in CFA. BALB/c mice were immunized in the rear foot pad with 5–10 µg of protein emulsified in CFA. Protein concentration was determined using the Bio-Rad Protein Assay reagent (Bio-Rad Laboratories, Richmond, Calif.). The mice were boosted 7 days later with 5–10 µg of protein emulsified in incomplete Fretind's adjuvant (IFA). inoculated into the peritoneal cavity. The mice were bled 7 days after the second immunization. New Zealand white rabbits (Millbrook Farm, Amherst, Mass.) were immunized according to the following protocol: one intramuscular (IM) injection of 25–30 µg of purified recombinant protein emulsified in CFA into each thigh on day one; one IM injection of 25–30 µg of purified protein emulsified in IFA into each shoulder on day 7; on day 15, 25–30 µg of the purified protein in PBS was injected into the subcutaneous tissue. The rabbit was bled 7 days after the last immunization.

Sera were prepared and the anti-Leishmania antibody response was measured by Western blot analysis and by FACScan. In both cases L. donovani promastigotes were used as antigen. Approximately $2 \times 10^6$ L. donovani promastigotes were grown in Schneider's medium for 3 days (log phase), were washed with PBS, lysed with SDS-PAGE loading buffer and submitted to electrophoresis under reducing conditions using a 15% polyacrylamide gel. The proteins were transferred onto 0.45 µImmobilon-P transfer membrane (Millipore Co., Bedford, Mass.) using a wet-type electroblotter (Mini Trans-Blot Electrophoretic Transfer Cell, Bio Rad Life Science Division, Richmond, Calif.) for 2 hours at 50 V. The membranes were blocked overnight at room temperature with PBS containing 3% normal goat serum (NGS), 0.2% Tween-20 and 0.05% sodium azide, followed by 3 washes with PBS. The blots were then incubated for 3–4 hours at 4° C. with a 1/200 dilution of pre-immune rabbit serum (lane A, FIG. 5) or with the same dilution of anti-fusion protein rabbit antiserum (lane B, FIG. 5). The sera was previously absorbed 2× with non-viable desiccated *Mycobacterium tuberculosis* H-37 RA (Difco Laboratories, Detroit, Mich.) and were diluted in PBS containing 1% NGS and 5% powdered non-fat bovine milk (Carnation, Nestle Food Company, Glendale, Calif.). The membranes were then washed with PBS, incubated for 1 hour at room temperature with goat anti-rabbit IgG antibody conjugated with alkaline phosphatase (Promega, Madison, Wis.), washed once with PBS and 2× with veronal buffer pH 9.4. The reaction was visualized using the substrate mixture 5-bromo-4-chloro-3-indoyl-phosphate and nitroblue tetrazolium (Kirkegaard & Perry Laboratories Inc., Gaithersburg, Md.) according to the manufacturer's instructions.

Figure 6:
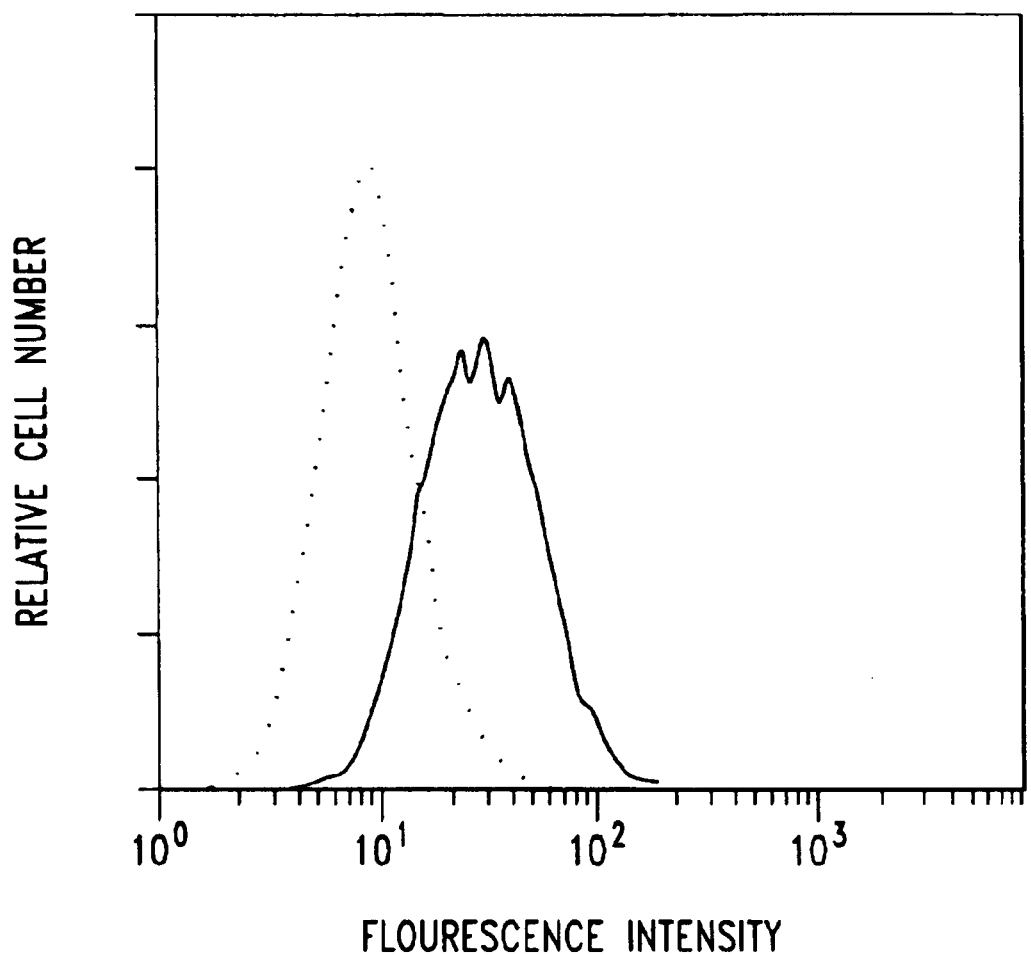
FIG. 6 illustrates the surface expression of Ldp23 on live *L. donovani* promastigotes. The dotted line shows the indirect immunofluorescence performed using pre-immune mouse serum and the solid line shows the result obtained with mouse anti-GST-Ldp23 antiserum. Fluorescence intensity was analyzed by FACScan.

FIG. 5 shows that the rabbit anti-recombinant protein antiserum detects a single protein of 23 kDa (Ldp23) in the Leishmania crude extract antigen preparation. No bands were observed when an anti-GST antiserum was used (not shown). Moreover, the FACScan analysis (FIG. 6) shows that the antibody induced by the recombinant Ldp23 reacts with intact live *L. donovani* promastigotes, thus pointing to a cell surface expression of this molecule on these organisms. The dotted line in FIG. 6 shows the indirect immunofluorescence performed using pre-immune mouse serum and the solid line in FIG. 6 shows the result obtained with mouse anti-GST-Ldp23 antiserum. Both sera were diluted at 1/100. Parasites were washed with staining buffer and incubated with FITC conjugated goat anti-mouse immunoglobulin antibody. Fluorescence intensity was analyzed by FACScan.

F. Recognition of Recombinant Ldp23 by Leishmania-Specific Lymph Node T-Cells

Figure 7:
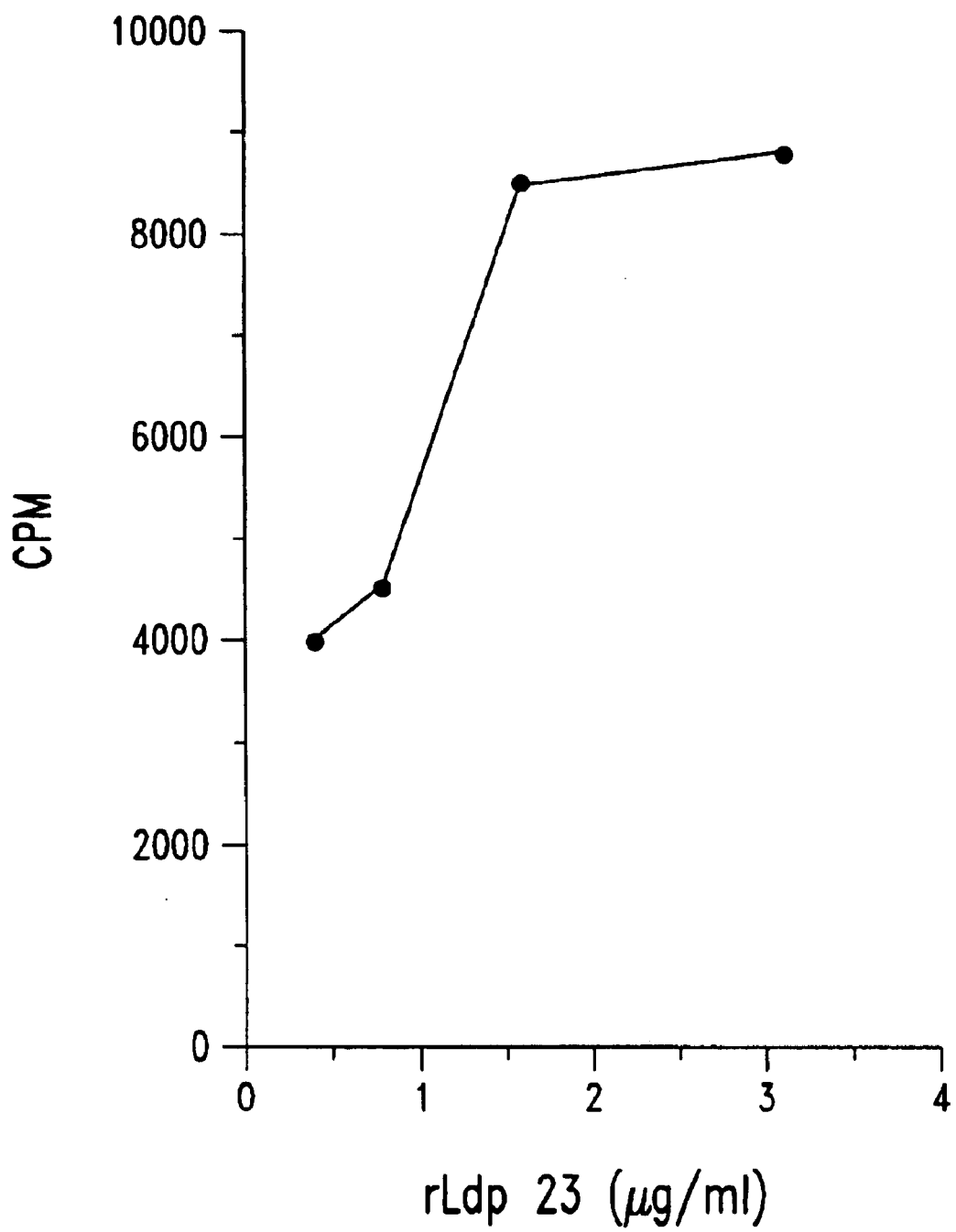
FIG. 7 shows the stimulation of Leishmania-specific T-cell proliferation by Ldp23. The results are presented as relative cell number as a function of fluorescence intensity. T-cells ($10^5$/well) were purified from lymph nodes of BALB/c mice immunized in the foot pad with *L. donovani* promastigotes in CFA and were cultured with various concentrations of the purified recombinant Ldp23 in the presence of $2 \times 10^5$ Mitomycin C-treated normal BALB/c spleen mononuclear cells. Proliferation of T-cells was measured at 27 hours of culture. Values are expressed as cpm and represent the mean of [$^3$H]TdR incorporation of triplicate cultures.

To test the responsiveness of T-cells to the Ldp23 protein, two sets of experiments were performed. In the first experiment, lymph node T-cells ($10^5$/well) from BALB/c mice immunized with *L. donovani* promastigotes (as described above) were stimulated to proliferate with $2 \times 10^5$ Mitomycin C-treated normal mononuclear spleen cells (APC) and pulsed with the purified recombinant fusion protein. Proliferation of T-cells was measured at 72 hours of culture. Values are expressed in FIG. 7 as cpm and represent the mean of [$^3$H]TdR incorporation of triplicate cultures. Background cpm of cells (T cells+APC) cultured in the presence of medium alone was 1291. FIG. 7 shows that Leishmania specific T-cells proliferate well and in a dose response manner to recombinant Ldp23. No response was observed when purified GST was added instead of the recombinant fusion protein nor when lymph node T-cells from mice immunized with CFA alone were stimulated to proliferate in the presence of the Leishmanial fusion protein (not shown).

The recognition of the recombinant Ldp23 protein by Leishmania-specific T-cells was also tested using two murine models of leishmaniasis, the *L. major* highly susceptible BALB/c mice and the *L. amazonensis* susceptible CBA/J mice as described in Champsi and McMahon-Pratt, *Infect. Immun*. 56:3272 (1988). These models were selected to investigate the cytokine pattern induced by Ldp23. In the mouse model of leishmaniasis, resistance is associated with Th1 cytokines while susceptibility is linked to Th2 responses.

Lymph node cells were obtained 3 weeks after the initiation of infection of BALB/c mice with *L. major* and the ability of these cells to recognize the recombinant Ldp23 was measured by proliferation and by the production of the cytokines IFN-γ and IL-4. $2 \times 10^6$ cells obtained from the draining popliteal lymph node of infected mice were cultured for 72 hours in the presence of recombinant Ldp23 or Leishmania lysate. The levels of IFN-γ and IL-4 in culture supernatants were measured by ELISA as previously described (Chatelain et al., *J. Immunol*. 148:1172 (1992), Curry et al., *J. Immunol. Meth*. 104:137 (1987), and Mossman and Fong, *J. Immunol. Meth*. 116:151 (1989)) using specific anti IFN-γ and IL-4 monoclonal antibodies (PharMingen, San Diego, Calif.).

Figures 8A, 8B:
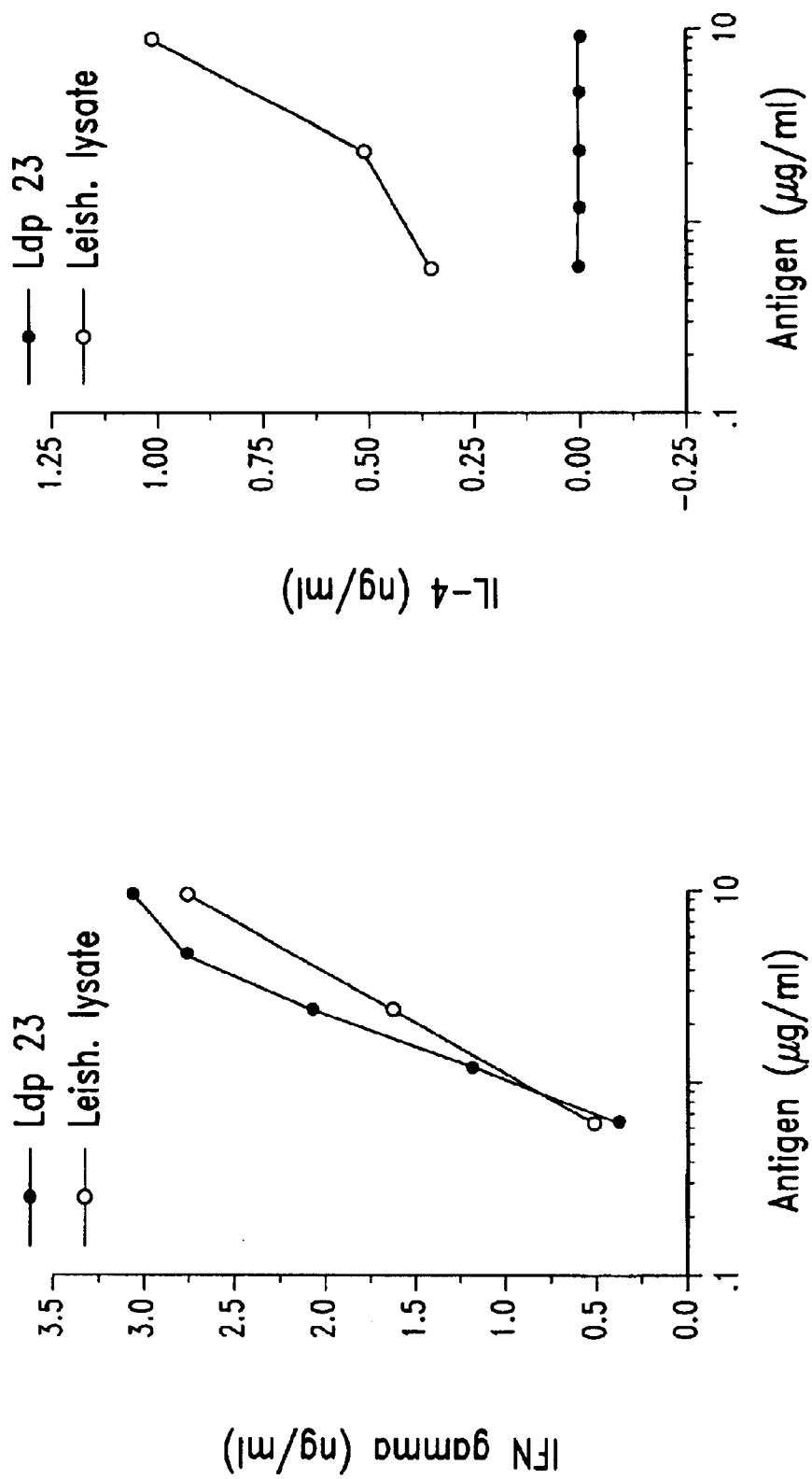
FIG. 8 illustrates Ldp23-induced cytokine production by lymph node cells of BALB/c mice. Cultures were incubated with varying amounts of Ldp23 or Leishmania lysate, presented as µg/mL, and were assayed by ELISA for the production of interferon-γ (panel A) or interleukin-4 (panel B), both of which are shown as ng/InL.

Ldp23 did stimulate these cells to proliferate (not shown) and induced a typical Th1 type of cytokine response as indicated by the production of high levels of IFN-γ (panel A of FIG. 8) and no IL-4 (panel B of FIG. 8). Stimulation of these cells with a Leishmania crude lysate yielded a mixed Th cytokine profile. Exactly the same pattern of cytokine production was obtained from the CBA/J mice infected with *L. amazonensis* (not shown). These results clearly indicate that Ldp23 is a powerful and selective activator of the Th1 cytokines by mouse cells.

Example 3

Preparation of HsP83

This Example illustrates the preparation of a Leishmania antigen Hsp83, having the sequence provided in SEQ ID NO:6.

A genomic expression library was constructed with sheared DNA from *L. braziliensis* (MHOM/BR/75/M2903) in bacteriophage λZAP II (Stratagene, La Jolla, Calif.). The expression library was screened with *Escherichia coli* preadsorbed serum from an *L. braziliensis*-infected individual with ML. Immunoreactive plaques were purified, and the pBSK(−) phagemid was excised by protocols suggested by the manufacturer. Nested deletions were performed with exonuclease III to generate overlapping deletions for single-stranded template preparations and sequencing. Single-stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems automated sequencer model 373A.

Recombinant antigens produced by these clones were purified from 500 ml of isopropyl-γ-D-thiogalactopyranoside (IPTG)-induced cultures as described in Skeiky et al., *J. Exp. Med*. 176:201–211 (1992). These antigens were then assayed for the ability to stimulate PBMC from Leishmania-infected individuals to proliferate and secrete cytokine. Peripheral blood was obtained from individuals living in an area (Corte de Pedra, Bahia, Brazil) where *L. braziliensis* is endemic and where epidemiological, clinical, and immunological studies have been performed for over a decade, and PBMC were isolated from whole blood by density centrifugation through Ficoll (Winthrop Laboratories, New York, N.Y.). For in vitro proliferation assays, $2 \times 10^5$ to $4 \times 10^5$ cells per well were cultured in complete medium (RPMI 1640 supplemented with gentamicin, 2-mercaptoethanol, L-glutamine, and 10% screened pooled A+ human serum; Trimar, Hollywood, Calif.) in 96-well flat-bottom plates with or without 10 μg of the indicated antigens per ml or 5 μg of phytohemagglutinin per ml (Sigma Immunochemicals, St. Louis, Mo.) for 5 days. The cells were then pulsed with 1 μCi of [$^3$H]thymidine for the final 18 h of culture. For determination of cytokine production 0.5 to 1 ml of PBMC was cultured-at $1\times10^6$ to $2\times10^6$ cells per ml with or without the Leishmania antigens for 48 and 72 h.

The supernatants and cells were harvested and analyzed for secreted cytokine or cytokine mRNAs. Aliquots of the supernatants were assayed for gamma interferon (IFN-γ), tumor necrosis factor alpha (TNF-α), interleukin-4 (IL-4), and IL-10 as described in Skeiky et al., *J Exp. Med.* 181:1527–1537 (1995). For cytokine mRNA PCR analysis, total RNA was isolated from PBMC and cDNA was synthesized by using poly(dT) (Pharmacia, Piscataway, N.J.) and avian mycloblastosis virus reverse transcriptase. Following normalization to β-actin, diluted cDNA was amplified by PCR using Taq polymerase (Perkin-Elmer Cetus, Foster City, Calif.) with 0.2 μM concentrations of the respective 5' and 3' external primers in a reaction volume of 50 μl. The nucleotide sequences of the primary pairs and the PCR conditions used were as described in Skeiky et al., *J Exp. Med.* 181:1527–1537 (1995). We verified that our PCR conditions were within the semiquantitative range by initially performing serial dilutions of the cDNAs and varying the number of cycles used for PCR. Plasmids containing the human sequences for IL-2, IFN-γ, IL-4, IL-10, and β-actin were digested, and the DNA inserts were purified after separation on 1% agarose gels. Radiolabeled $^{32}$P probes were prepared by the random priming method. PCR products were analyzed by electrophoresis on 1.5% agarose gels, transferred to nylon membranes, and probed with the appropriate $^{32}$P-labeled DNA insert.

A recombinant clone was identified in the above assays which, following sequence comparison of its predicted amino acid sequence with sequences of other proteins, was identified as a *Leishmania braziliensis* homolog of the eukaryotic 83 kD heat shock protein (Lbhsp83). The sequence of the clone is provided in SEQ ID NO:5 and the deduced protein sequence is provided in SEQ ID NO:6. On the basis of the homology, this clone, designated Lbhsp83a, appears to lack the first 47 residues of the full length 703 amino acid residues. Lbhsp83 has an overall homology of 94% (91% identity and 3% conservative substitution), 91% (84% identity and 7% conservative substitution) and 77% (61% identity and 16% conservative substitution) with *L. amazonensis* hsp83, *T. cruzi* hsp83 and human hsp89, respectively. A second clone (designated Lbhsp83b), which contained the 43 kD C-terminal portion of hsp83 (residues 331 to 703) was also isolated. FIG. 19 presents a comparison of the Lbhsp83 sequence with *L. amazonensis* hsp83 (Lahsp83), *T. cruzi* hsp83 (Tchsp83) and human hsp89 (Huhsp89).

The results of proliferation assays using Lbhsp83a are shown in Table 1. Cells from all mucosal leishmaniasis (ML) patients proliferated strongly in response to Lbhsp83a, with stimulation indices (SIs) ranging from 19 to 558 (as compared to 20 to 1,634 for parasite lysate). Proliferation of PBMC from cutaneous leishmaniasis (CL) patients was variable and except for levels in two patients (IV and VII), levels were significantly lower than those of ML patients. By comparison, the proliferative responses of individuals with self-healing CL to Lbhsp83a were similar to those of individuals with ML. However, the responses of all six self-healing individuals to Lbhsp83 were consistently higher than those to Lbhsp83b. This suggests that PBMC from self-healing CL patients preferentially recognize one or more T-cell epitopes located within the amino portion of Lbhsp83.

TABLE 1

In vitro Proliferation of PMBC from *L. braziliensis*-infected Individuals in Response to Lbhsp83

| Group and Patient | Mean [$^3$H]thymidine incorporation [$10^3$ cpm (SD)], SI with: | | |
|---|---|---|---|
| | Lysate | Lbhsp83a | Lbhsp83b |
| ML | | | |
| I | 41.3, (1.3), 294 | 32.5, (6.6), 221 | 46.7, (1.4), 318 |
| II | 44.2, (0.5), 104 | 20, (3.7), 47 | 36.7, (0.76), 86 |
| III | 27.4, (1.5), 150 | 8.1, (1.7), 44 | 9.9, (0.32), 54 |
| IV | 52.7, (3.3), 138 | 54.1, (6.2), 142 | 32.0, (1.3), 84 |
| V | 140.6, (7.6), 308 | 151.8, (57), 333 | 150.4, (7.9), 331 |
| VI | 15.8, (1.8), 20 | 21.3, (4.4), 28 | 14.4, (1.3), 19 |
| VII | 300.1, (9.4), 1634 | 102.1, (7.6), 558 | 41.7, (4.9), 228 |
| CL | | | |
| I | 0.26, (0.0), 1.5 | 0.57, (0.3), 3.3 | 0.43, (0.17), 3.3 |
| II | 55.63, (8.6), 218 | 0.42, (0.0), 1.6 | 0.8, (0.14), 3.2 |
| III | 0.39, (0.5), 4.0 | 3.4, (0.5), 9 | 2.6, (0.9), 6.6 |
| IV | 19.14, (1.3), 87 | 7.17, (0.6), 32 | 5.9, (0.9), 27 |
| V | 0.32, (0.2), 3.0 | 1.47, (0.5), 14 | 0.3, (0.1), 3.0 |
| VI | 0.77, (0.1), 4.7 | 1.44, (0.2), 9 | 1.3, (0.6), 8.0 |
| VII | 4.01, (1.0), 2.0 | 60.3, (8.5), 15 | 66.7, (3.9), 16.6 |
| Self-healing CL | | | |
| I | 19.7, (4.4), 94 | 61.3, (4.6), 293 | 5.0, (2.0), 24 |
| II | 0.6, (0.1), 6.5 | 7.0, (2.0), 79 | 1.2, (0.8), 13 |
| III | 59.6, (7.1), 519 | 49.4, (3.1), 429 | 21.4, (3.7), 186 |
| IV | 0.2, (0.1), 1.6 | 13.1, (1.7), 108 | 0.6, (0.1), 5 |
| V | 27.1, (2.0), 225 | 6.3, (2.6), 52 | 3.0, (1.5), 25 |
| VI | 130.3, (14), 340 | 28.2, (2.9), 74 | 7.7, (3.8), 20 |
| Control (uninfected) | | | |
| I | 0.19, (0.0), 1.4 | 0.18, (0.0), 1.3 | 0.40, (0.16), 2.8 |
| II | 0.31, (0.1), 1.7 | 0.19, (0.0), 1.0 | 0.27, (0.0), 1.5 |
| III | 0.44, (0.2), 4.1 | 0.48, (0.1), 5.0 | 0.51, (0.2), 5.2 |
| IV | 0.4, (0.1), 3.2 | 0.52, (0.2), 5.1 | 0.50, (0.1), 5.0 |

Figure 9A:
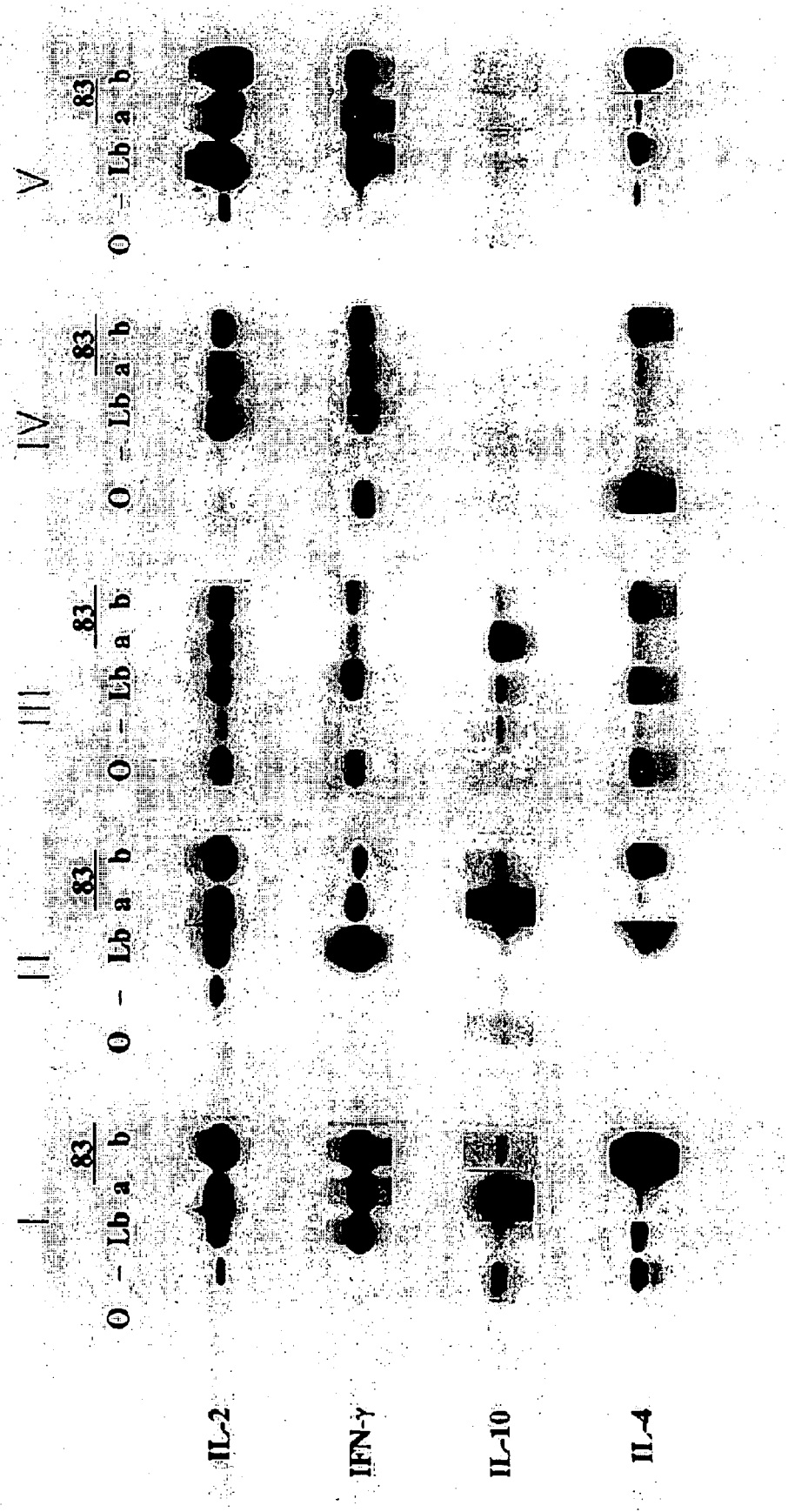
FIG. 9 shows the PCR amplification of cytokine mRNAs isolated from mucosal leishmaniasis (Panel A) and cutaneous leishmaniasis (panel B) patient PBMC before and after stimulation with representative polypeptides of the present invention. Lanes O and—indicate the level of PCR products at the initiation of culture and after 72 hours of culture, respectively, in the absence of added polypeptide; lanes Lb, 83a and 83b indicate the level of PCR products following culturing of PBMC with *L. braziliensis* lysate, and the Leishmania antigens Lbhsp 83a and Lbhsp 83b, respectively.
Figure 9B:
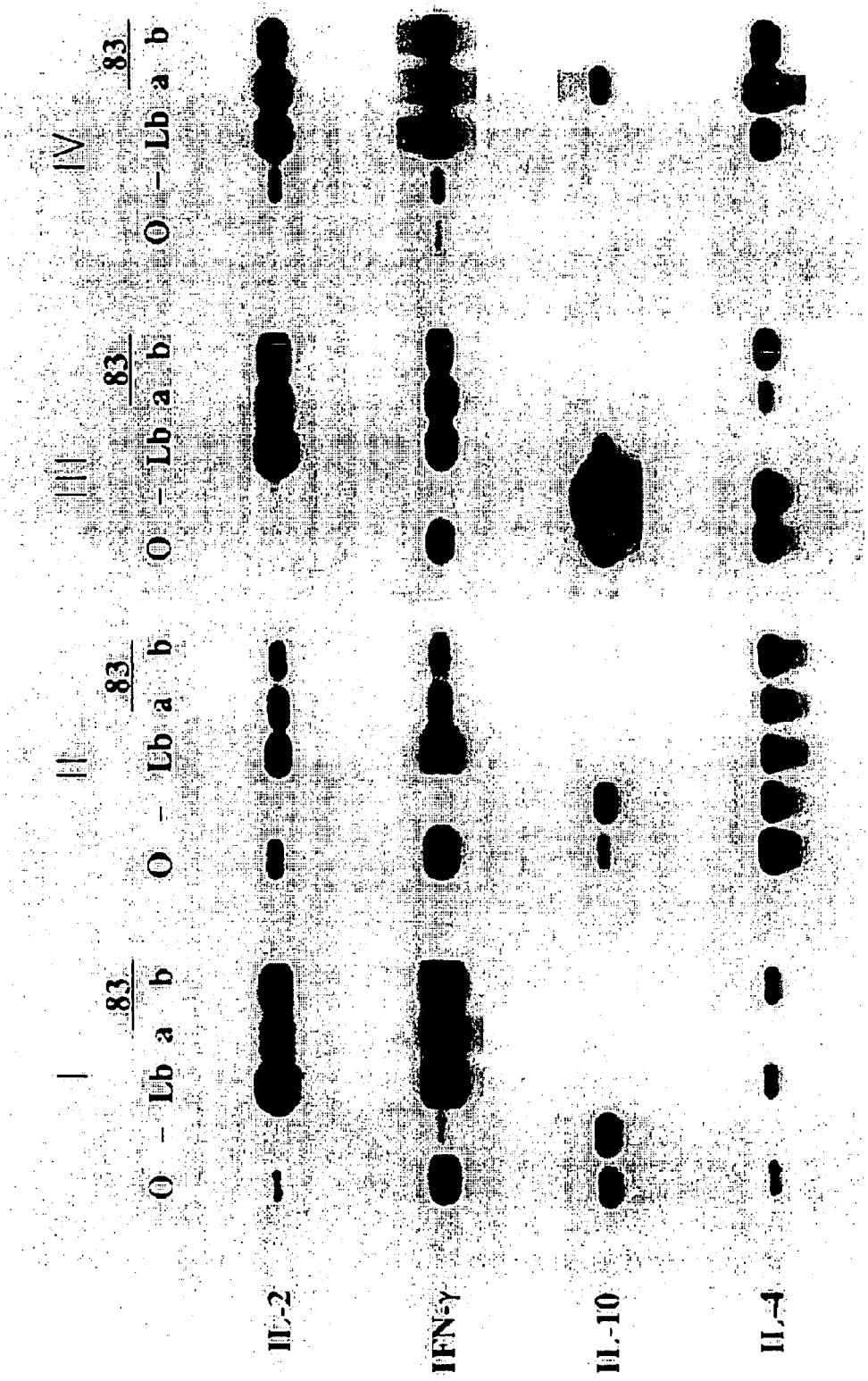

A more detailed analysis of cytokine patterns of PBMC from ML patients was performed by reverse transcriptase PCR. Cytokine mRNAs were evaluated in cells prior to culturing (FIG. 9, lanes O) or following culturing in the absence (lanes—) or presence of the indicated antigen for 48 and 72 h. FIG. 4A shows the results for five of the six ML patients whose PBMC were analyzed. In about half of the ML patients, noncultured (resting) PBMC had detectable levels of MRNA for IFN-γ, IL-2, and IL-4 but not IL-10. CL patient PBMC, however, had IL-10 MRNA in the resting state in addition to mRNAs for the other cytokines tested (FIG. 4B). Following in vitro culture without antigen, the levels of mRNA for IFN-γ, IL-2, and IL-4 in resting cells from ML patients decreased to background levels while IL-10 mRNA levels increased. In contrast, PBMC of most CL patients had stable or increased IL-10 mRNA, while the mRNAs for IL-2, IFN-γ, and IL-4 were reduced to barely detectable levels in the absence of antigen stimulation.

In PBMC of three ML patients, stimulation with lysate resulted in increased expression of mRNA for IFN-γ, IL-2, and IL-4 but not IL-10. By comparison, both Lbhsp83 polypeptides elicited the production of mRNA for IFN-γ and IL-2 from all ML patient PBMC tested. In contrast, profiles of MRNA for IL-10 and IL-4 differed for the two hsp83 polypeptides. Lbhsp83a stimulated the production of IL-10 but not IL-4 MRNA (patients I, II, III, and IV), while Lbhsp83b stimulated the production of IL-4 but not IL-10 mRNA in all six patients.

All CL patients tested responded to both Lbhsp83 polypeptides as well as to the parasite lysate by upregulating the synthesis of mRNAs for IL-2 and IFN-γ, and in two of four patients (I and IV), the level of IL-4 mRNA also increased, indicating stimulation of both Th1 and Th2 cytokines. Interestingly and as in the case of ML patient uncultured PBMC which did not have detectable levels of IL-10 mRNA, Lbhsp83a and not Lbhsp83b stimulated PBMC from one CL patient (IV) to synthesize IL-10 mRNA. However, in the other three patients (I, II, and III) with resting levels of IL-10 mRNA, both rLbhsp83 polypeptides as well as the parasite lysate downregulated the expression of IL-10 mRNA.

Figure 10A:
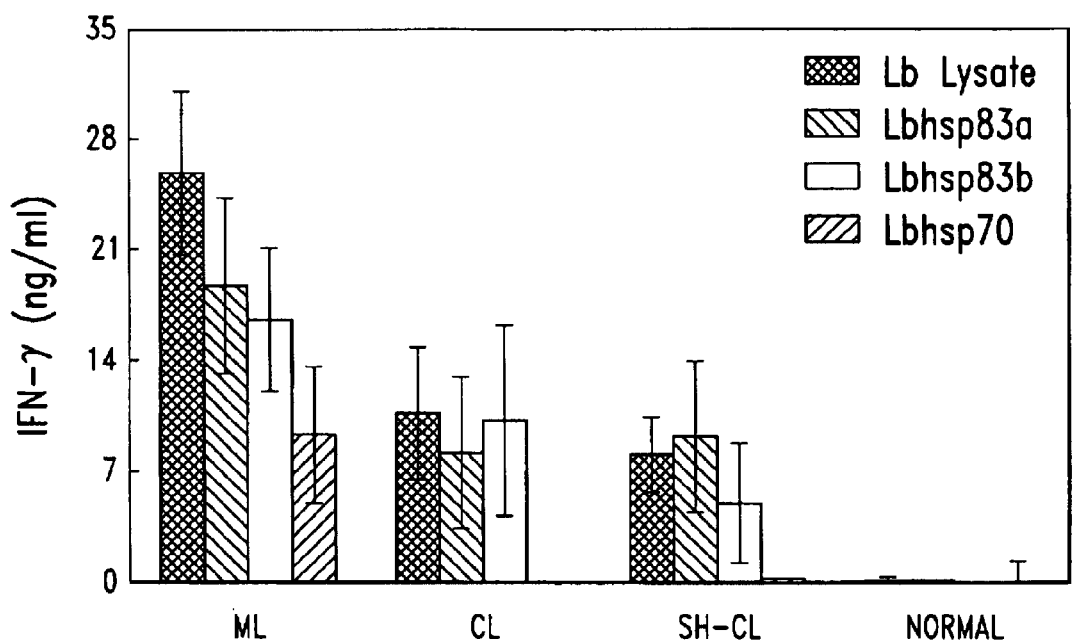
FIG. 10 presents a comparison of the levels of interferony (panel A) and TNF-α (panel B) in the supernatants of 72 hour PBMC cultures from Leishmania-infected and control individuals in response to stimulation with parasite lysate or the indicated polypeptides.
Figure 10B:
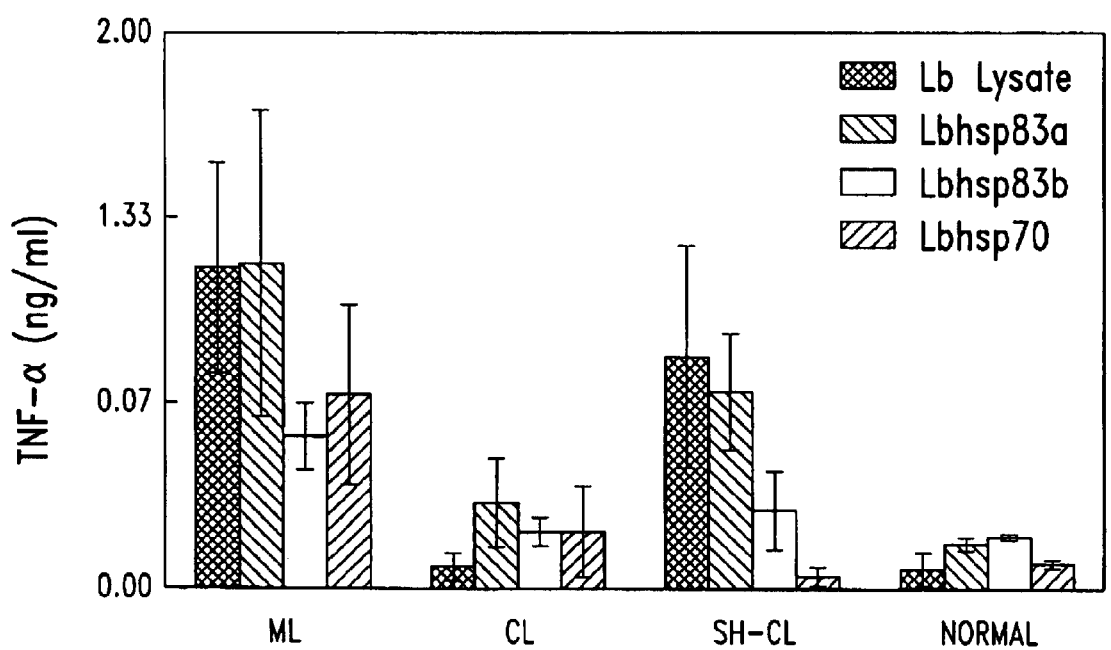

PBMC supernatants were also assayed for the presence of secreted IFN-γ, TNF-α, IL-4, and IL-10. Cells from all ML and self-healing CL patients (seven and six patients, respectively) and from four of seven CL patients were analyzed for secreted IFN-γ following stimulation with both rLbhsp83 polypeptides, parasite lysate and Lbhsp70, an *L. braziliensis* protein homologous to the eukaryotic 70 kD heat shock protein (FIG. 10A). In general, rLbhsp83a stimulated patient PBMC to secrete higher levels of IFN-γ than did rLbhsp83b (0.2 to 36 and 0.13 to 28 ng/ml, respectively). The presence of secreted IFN-γ correlated well with the corresponding MRNA detected by PCR PBMC from four of five ML patients (I, II, V, and VII) had supernatant TNF-α levels (0.8 to 2.2 ng/ml) higher than those detected in cultures of PBMC from uninfected controls following stimulation with parasite lysate (FIG. 10B). Similarly, the same PBMC were stimulated by rLbhsp83 to produce levels of TNF-α in supernatant ranging from 0.61 to 2.9 ng/ml. Compared with those of uninfected controls, PBMC from three (I, V, and VI), five (I, II, IV, V, and VI), and two (II and V) of six individuals analyzed produced higher levels of TNF-α in response to parasite lysate, rLbhsp83a, and rLbhsp83b, respectively. The levels of TNF-α produced by PBMC from CL patients in response to parasite lysate were comparable to those produced by uninfected controls. However, rLbhsp83 stimulated TNF-α production in the PBMC of two of these patients. rLbhsp83a stimulated higher levels of TNF-α production than did rLbhsp83b. In the absence of antigen stimulation, only PBMC from ML patients (five of six) produced detectable levels of supernatant TNF-α (60 to 190 pg/ml).

Figure 11:
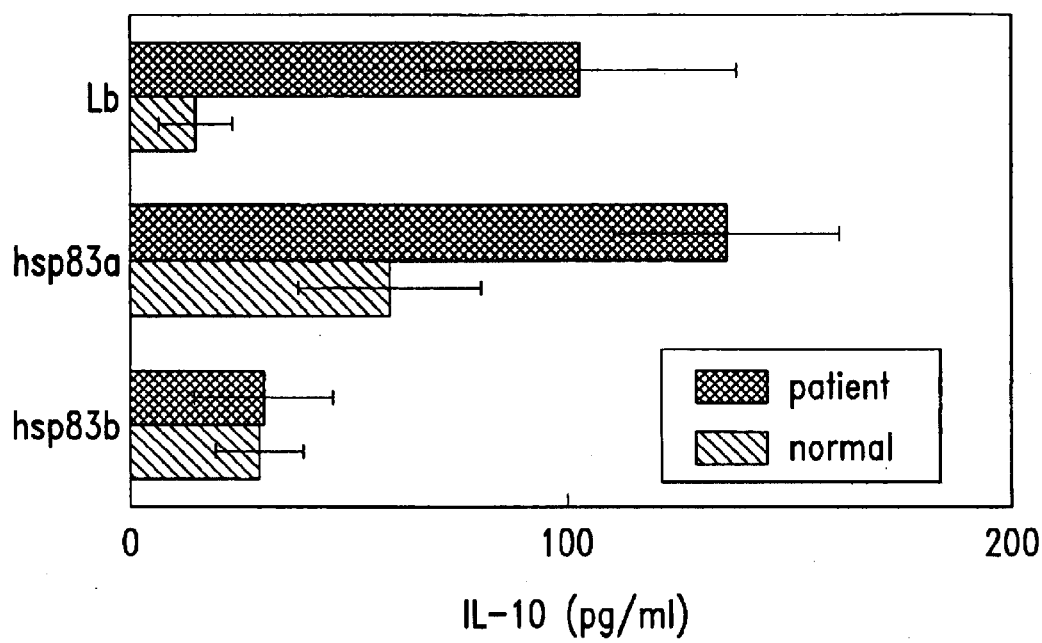
FIG. 11 illustrates the levels of IL-10 p40 (in pg/niL) in the supernatant of PBMC cultures from *L. braziliensis*-infected individuals and uninfected controls 72 hours following stimulation with parasite promastigote lysate (Lb), Lbhsp83a or Lbhsp83b.

In agreement with the IL-10 mRNA, IL-10 was detected by ELISA in the antigen-stimulated PMBC culture supernatants from ML and CL patients. The levels (49to 190pg) were significantly higher (up to 10-fold) following stimulation with rLbhsp83a compared with those after parallel stimulation of the same cells with rLbhsp83b (FIG. 11). Parasite lysate also stimulated PMBC from some of the patients to produce IL-10. Although rLbhsp83 stimulated PMBC from uninfected individuals to produce IL-10, with one exception, the levels were lower than those observed with patient PMBC. IL-4 was not detected in any of the supernatants analyzed. Therefore, the level of any secreted IL-4 is below the detection limit of the ELISA employed (50 pg/ml). Taken together, the results demonstrate that a predominant Th1-type cytokine profile is associated with PMBC from *L. braziliensis*-infected individuals following stimulation with rLbhsp83 polypeptides.

Figure 12:
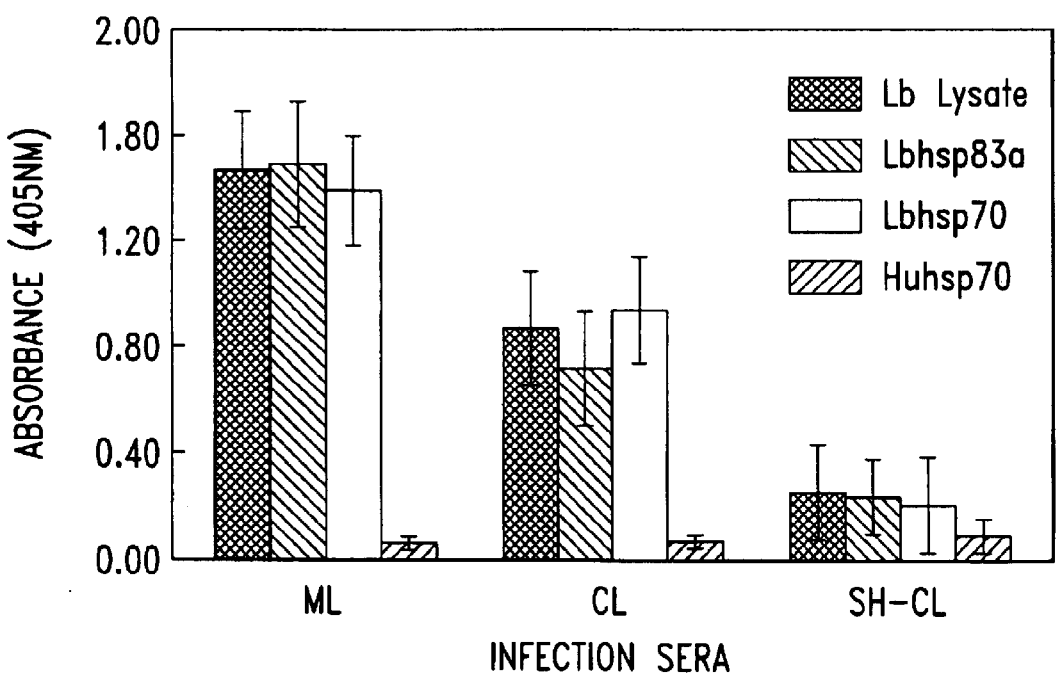
FIG. 12 presents the reactivities of sera from *L. braziliensis* infected-patients with representative polypeptides of the present invention in a standard ELISA. Values are expressed as absorbance at 405 nm.

To determine the correlation between the observed T-cell responses and antibody production to Lbhsp83, we compared the antibody (immunoglobulin G) reactivities to Lbhsp83 in sera from the three patient groups (FIG. 12). The ELISA reactivities of ML patient sera with rLbhsp83a were comparable to those observed with parasite lysate, and in general, there was a direct correlation between ML patient anti-Lbhsp83 antibody titer and T-cell proliferation. Of 23 serum samples from ML patients analyzed, 22 were positive (~96%) with absorbance values of 0.20 to>3.0. Eleven of the ML patient serum samples had optical density values that were>1. In general, CL patients had significantly lower anti-Lbhsp83 antibody titers ($\bar{x}$=0.74; standard error of the mean [SEM]=0.1) compared to those of ML patients. Therefore, ML and CL patient anti-rhsp83 antibody titers correlated with their respective T-cell proliferative responses. Anti-rLbhsp83 antibody titers were significantly higher in patients with ML ($\bar{x}$=1.5; SEM=0.2) than in self-healing CL patients ($\bar{x}$=0.35; SEM=0.056), although their T-cell proliferative responses were similar. In fact, anti-Lbhsp83 antibody titers in serum from self-healing CL patients were comparable to those from uninfected controls ($\bar{x}$=0.24; SEM=0.028). By using 2 standard deviations greater than the mean absorbance value of uninfected control (0.484) as a criterion for positive reactivity to Lbhsp83, eight of nine of the self-healing patient serum samples tested were negative.

Example 4

Preparation of Clones Encoding LT-210

This Example illustrates the preparation of clones encoding portions of the Leishmania antigen Lt-2 10, and which has the sequence provided in SEQ ID NO:8.

An expression library was constructed from *L. tropica* (MHOM/SA/91;/WR1063C) genomic DNA. The DNA was isolated by solubilizing *L. tropica* promastigotes in 10 mM Tris-HCI, pH 8.3, 50 mM EDTA, 1% SDS and treating with 100 μg/ml RNaseA and 100 μg/ml proteinase K. The sample was then sequentially extracted with an equal volume of phenol, phenol: chloroform (1:1), and Chloroform. DNA was precipitated by adding 0.1 volume of 3M sodium acetate (pH 5.2) and 2.5 volume 95% ethanol. The precipitate was resuspended in 10 μM Tris, ImM EDTA. DNA was sheared by passage through a 30-gauge needle to a size range of 2–6 kilobase, and was repaired by incubation with DNA poll in the presence of 100 μM each dATP, dCTP, dGTP, and dTTP. EcoRI adapters were ligated to the DNA fragments. After removal of unligated adapters by passage over a G-25 Sephadex™ column, the fragments were inserted in EcoRI cut Lambda Zapll (Stratagene, La Jolla, Calif.).

Approximately 43,000. pfu were plated and screened with sera isolated from viscerotropic leishmaniasis (VTL) patients. Sera from VTL patients were received from Drs. M. Grogi and A. Magill. The VTL patient group included eight individuals from whom parasites were isolated and cultured, seven of which had confirmed infection with *L. tropica*. Four other patients were culture negative, but were still considered to be infected based on either PCR analysis or a positive monoclonal antibody smear (Dr. Max Grogl, personal communication). Serum samples from the 11 infected patients were pooled and anti-*E. coli* reactivity removed by affinity chromatography (Sambrook et al., supra, p. 12.27–12.28). Lambda phage expressing reactive proteins were detected after antibody binding by protein A-horseradish peroxidase and ABTS substrate.

Three clones, Lt-1, Lt-2, and Lt-3, containing a portion of the Lt-210 gene were identified and purified. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, Gene 30 28:351–359, 1984). Single strand template was prepared and the sequence determined with Applied Biosystems Automated Sequencer model 373A or by Sanger dideoxy sequencing. The sequence on both strands of the coding portion of Lt-1 clone was determined. The partial sequence of one strand of Lt-2 clone was determined.

SEQ ID NO:7 presents the DNA sequence of Lt-1, and SEQ ID NO:8 provides the predicted amino acid sequence of the open reading frame. The DNA sequence of the coding portion of the Lt-1 clone includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies. The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely (a-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same gene, Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Schleicher & Schuell, Keene, NH). Inserts from rLt-1 and rLt-2 were labeled with $^{32}$P-CTP by reverse transcriptase from random oligonucleotide primers and used as probes after separation from unincorporated nucleotides on a Sephadex G-50 column. Hybridizations using the rLt-1 or the rLt-2 probe are performed in 0.2 M NaH$_2$PO$_4$/3.6 M NaCl at 65° C., whereas hybridization using the rLt-1r probe is performed in 0.2 M NaH$_2$PO$_4$/3.6 M NaCl/0.2 M EDTA at 60° C. overnight. Filters are washed in 0.075 M NaCl/0.0075 M sodium citrate pH 7.0 (0.15 M NaCl/0.0150 M sodium citrate for the Lt-1r probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy number. A similar, overlapping pattern was observed using either the Lt-1 or Lt-2 insert as a probe, consistent with the premise that these two clones contain sequences near or overlapping one another. In addition, sequences hybridizing with these clones are present in other Leishmania species.

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert described below was labeled and used as a probe. The seven different *L. tropica* isolates yielded similar intensities and restriction patterns, with only a single restriction fragment length polymorphism among the isolates. These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript SK-phagemid from Lambda Zap II was performed according to the manufacturer's protocol. Phagemid virus particles were used to infect *E. coli* XL-1 Blue. Production of protein was induced by the addition of IPTG. Protein was recovered by first lysing pellets of induced bacteria in buffer (LB, 50 mM Tris-HCl, pH 8.0, 100 mM NaCl, 10 mM EDTA) using a combination of lysozyme (750 μg/mL) and sonication. rLt-1, rLt-2, and rLt-1r, were recovered from the inclusion bodies after solubilization in 8M urea (rLt-1 and rLt-2) or 4M urea (rLt-1r). Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

Example 5

Preparation of LbeIF4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM 13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T-cell assays for their ability to stimulate a proliferative and cytokine production, as described in Examples 7 and 8 below.

A recombinant clone was identified in the above assays which, following sequence comparison of its predicted amino acid sequence with sequences of other proteins, was identified as a *Leishmania braziliensis* homolog of the eukaryotic initiation factor 4A (eIF4A). The isolated clone (pLeIF.1) lacked the first 48 amino acid residues (144 nucleotides) of the full length protein sequence. The pLeIF.1 insert was subsequently used to isolate the full length genomic sequence.

SEQ ID NO:7 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 6

Preparation of Soluble Leishamnia Antigens

This Example illustrates the preparation of soluble Leishmania antigens from an *L. major* culture supernatant. *L. major* promastigotes were grown to late log phase in complex medium with serum until they reached a density of 2–3×10$^7$ viable organisms per miL of medium. The organisms were thoroughly washed to remove medium components and resuspended at 2–3×10$^7$ viable organisms per mL of defined serum-free medium consisting of equal parts RPMI 1640 and medium 199, both from Gibco BRL, Gaithersburg, MD. After 8–12 hours, the supernatant was removed, concentrated 10 fold and dialyzed against phosphate-buffered saline for 24 hours. Protein concentration was then determined and the presence of at least eight different antigens confirmed by SDS-PAGE. This mixture is referred to herein as "soluble Leishmania antigens."

Example 7

Comparison of Interleukin-4 and Interferon-γ Production Stimulated by Leishmania Antigens This Example illustrates the immunogenic properties of the antigens prepared according to Examples 1, 2, 5 and 6, as determined by their ability to stimulate IL-4 and IFN-γ in lymph node cultures from infected mice and in human PBMC preparations. Lymph node cultures for use in these studies were prepared from *L. major*-infected BALB/c mice 10 days after infection, as described in Example 2. PBMC were prepared using peripheral blood obtained from individuals with cured *L. donovani* infections who were immunologically responsive to Leishmania. Diagnosis of the patients was made by clinical findings associated with at least one of the following: isolation of parasite from lesions, a positive skin test with Leishmania lysate or a positive serological test. Uninfected individuals were identified based on a lack of clinical signs or symptoms, a lack of history of exposure or travel to endemic areas, and the absence of a serological or cellular response to Leishmania antigens. Peripheral blood was collected and PBMC isolated by density centrifugation through Ficoll™ (Winthrop Laboratories, New York).

Culture supernatants were assayed for the levels of secreted IL-4 and IFN-γ. IFN-γ was quantitated by a double sandwich ELISA using mouse anti-human IFN-γ mAb (Chemicon, Temucula, Calif.) and polyclonal rabbit anti-human IFN-γ serum. Human rIFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml.

Figure 13A:
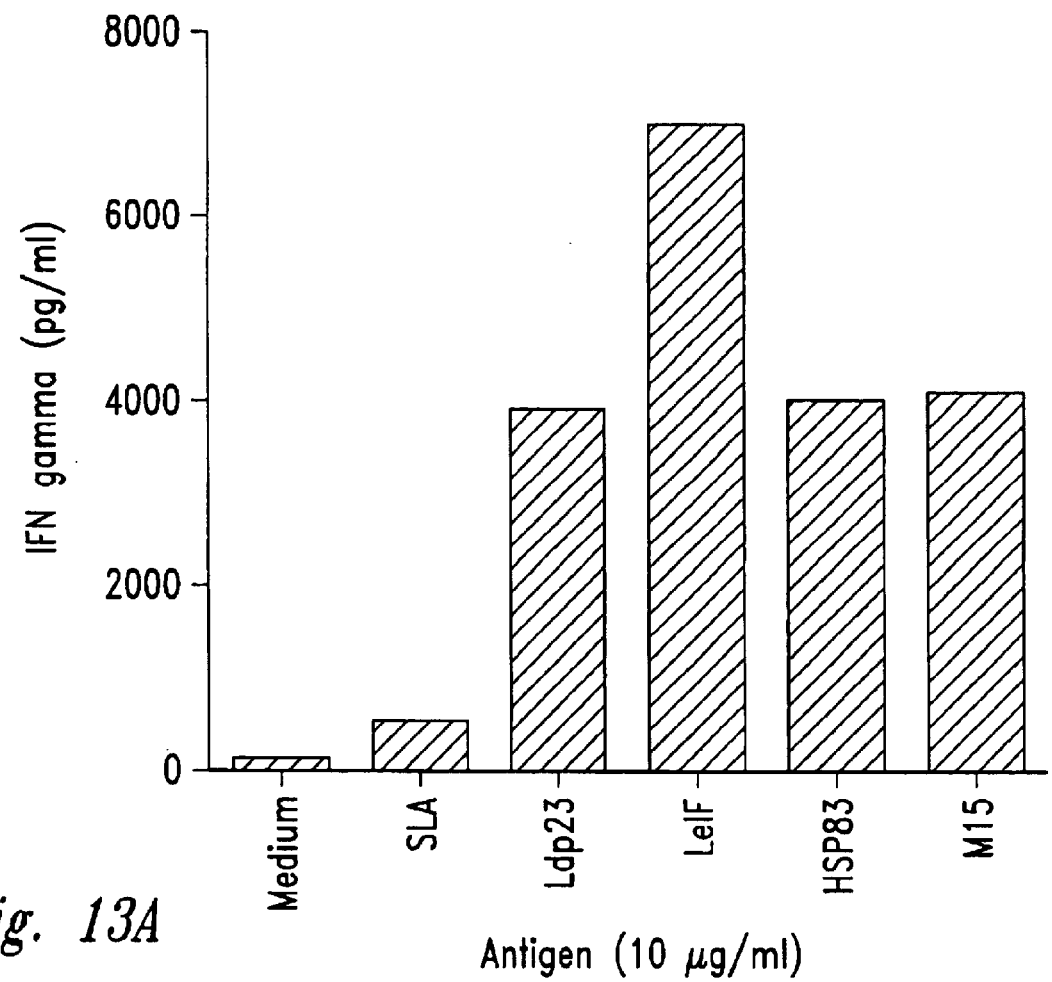
FIGS. 13A and 13B illustrate the level of secreted IL-4 and IFN-γ (in pg/mL) stimulated in mouse lymph node cultures by the addition of representative polypeptides of the present invention.
Figure 13B:
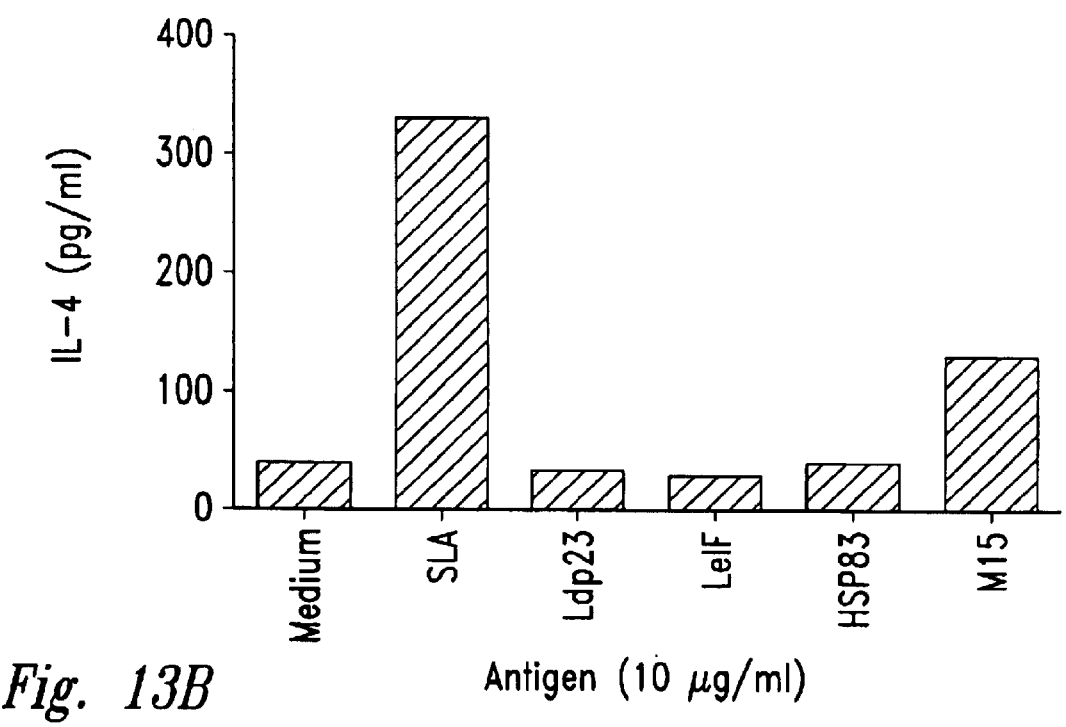

FIGS. 13A and 13B, illustrate the mean level of secreted IL-4 and IFN-γ, respectively, 72 hours after addition of 10 μg/mL of each of the following antigens to a lymph node culture prepared as described above: soluble Leishmania antigen (i.e., an extract prepared from ruptured promastigotes which contains membrane and internal antigens (SLA)), Ldp23, LbeIF4A (LeIF), Lbhsp83, M15 and LmeIF (the *L. major* homolog of LbeIF4A). The levels of secreted IL-4 and IFN-γ in medium alone (i.e., unstimulated) are also shown. While SLA elicits a predominantly Th2 response from lymph node cells of Leishmania-infected mice, Ldp23, LbeIF4A, Lbhsp83 and M15 elicited relatively little IL-4 and large amounts of IFN-γ, consistent with a Th1 response profile.

Figure 14:
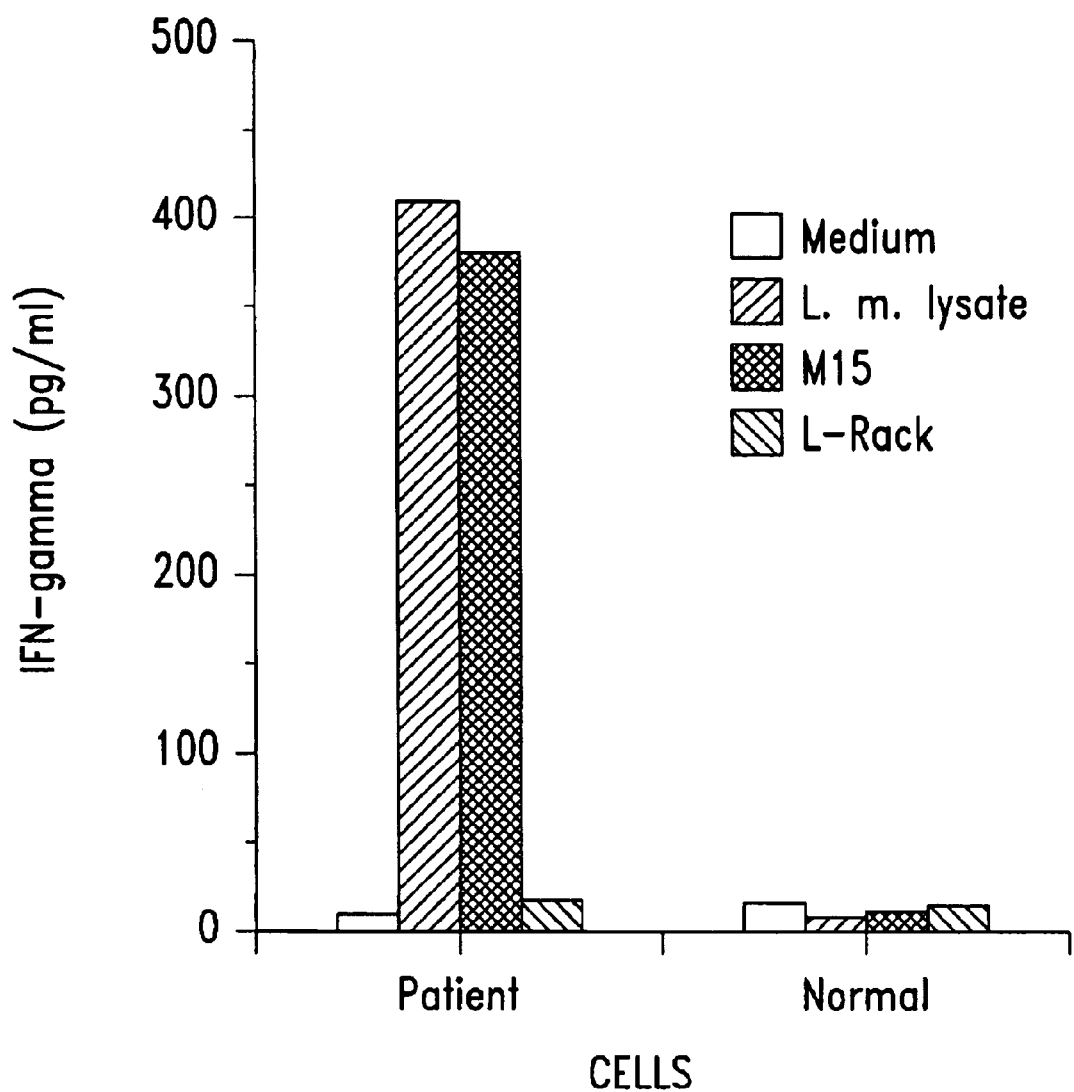
FIG. 14 shows the level of IFN-γ (in pg/mL) secreted by Leishmania-infected and uninfected human PBMC stimulated by the Leishmania antigen M15, as compared to the levels stimulated by *L. major* lysate and L-Rack, an antigen that does not appear to be recognized by Leishmania-infected humans.
Figure 15:
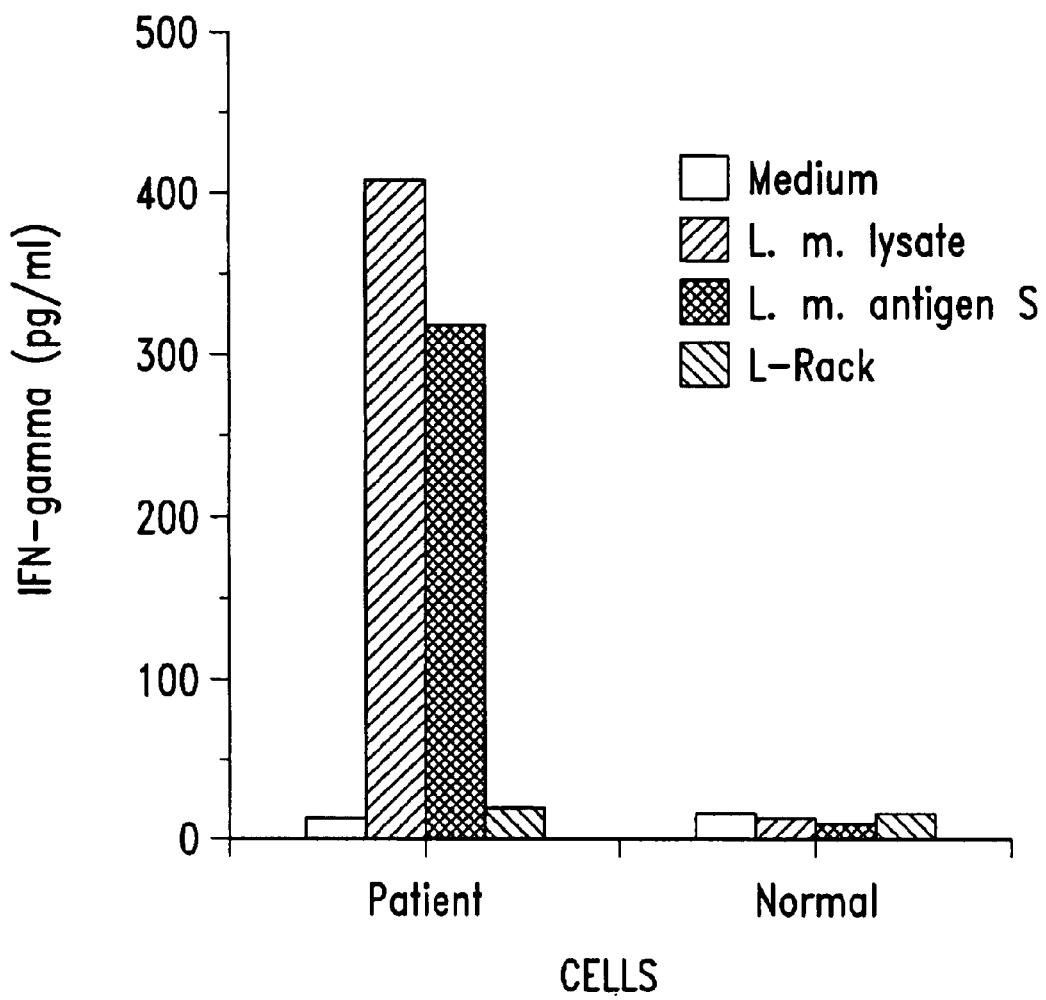
FIG. 15 shows the level of IFN-γ (in pg/mL) secreted by infected and uninfected human PBMC stimulated by soluble Leishmania antigens (S antigens), as compared to the levels stimulated by *L. major* lysate and L-Rack.

FIG. 14 shows the level of secreted IFN-γ in culture filtrate from infected and uninfected human PBMC preparations 72 hours after addition of 10 μg/mL *L. major* lysate, M15 or L-Rack, an immunodominant leishmanial antigen in murine leishmaniasis. Similarly, FIG. 15 illustrates the level of secreted IFN-γ in culture filtrate from infected and uninfected human PBMC preparations 72 hours after addition of 10 ∞g/mL *L. major* lysate, soluble Leishmania antigens (prepared as described in Example 6) or L-Rack. These results indicate that M15 and soluble Leishmania antigens, but not L-Rack, are potent stimulators of IFN-γ production in patient PBMC, but not in PBMC obtained from uninfected individuals. Thus, M15 and soluble Leishmania antigens elicit a dominant Th1 cytokine profile in both mice and humans infected with Leishmania.

Example 8

Comparison of Proliferation Stimulated by Leishmania Antigens

This Example illustrates the immunogenic properties of the antigens prepared according to Examples 1, 2, 5 and 6, as determined by their ability to stimulate proliferation in lymph node cultures from infected mice and in human PBMC preparations.

For in vitro proliferation assays, 2–4×10$^5$ cells/well were cultured in complete medium (RPMI 1640 supplemented with gentamnycin, 2-ME, L-glutamnine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of [$^3$H] thymidine for the final 18 hours of culture.

Figure 16:
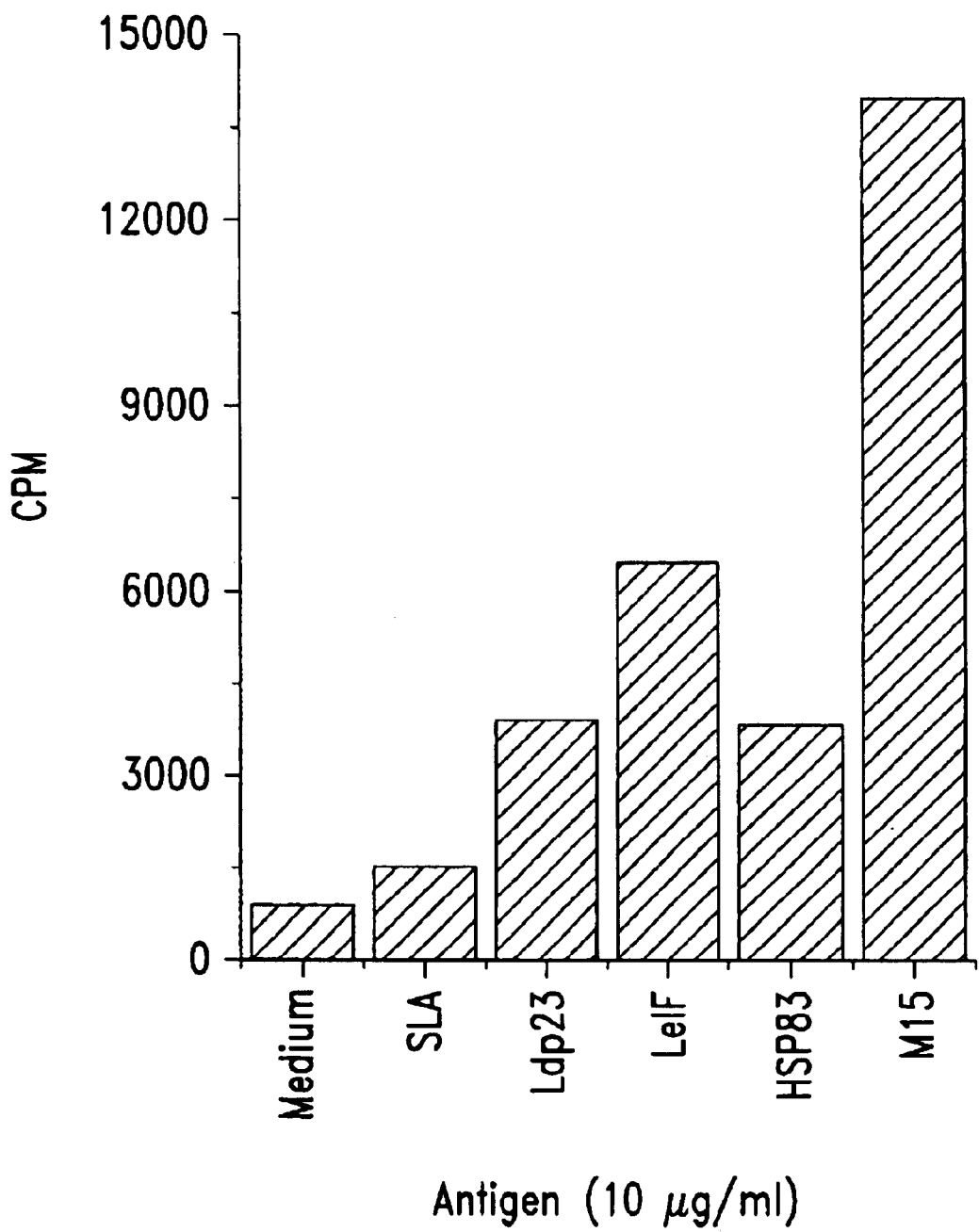
FIG. 16 illustrates the proliferation of murine lymph node cultures stimulated by the addition of representative polypeptides of the present invention. Values are expressed as cpm.

FIG. 16 illustrates the proliferation observed after addition of 10 μg/mL or 20 μg/mL of each of the following antigens to a lymph node culture prepared as described in Example 7: SLA, Ldp23, LbeIF4A, Lbhsp83, and M15. The level of proliferation without the addition of antigen is also shown. Data are represented as mean cpm. These results demonstrate that a variety of leishmanial antigens are capable of stimulatory lymph node cell proliferation from Leishmania-infected mice.

Figure 17:
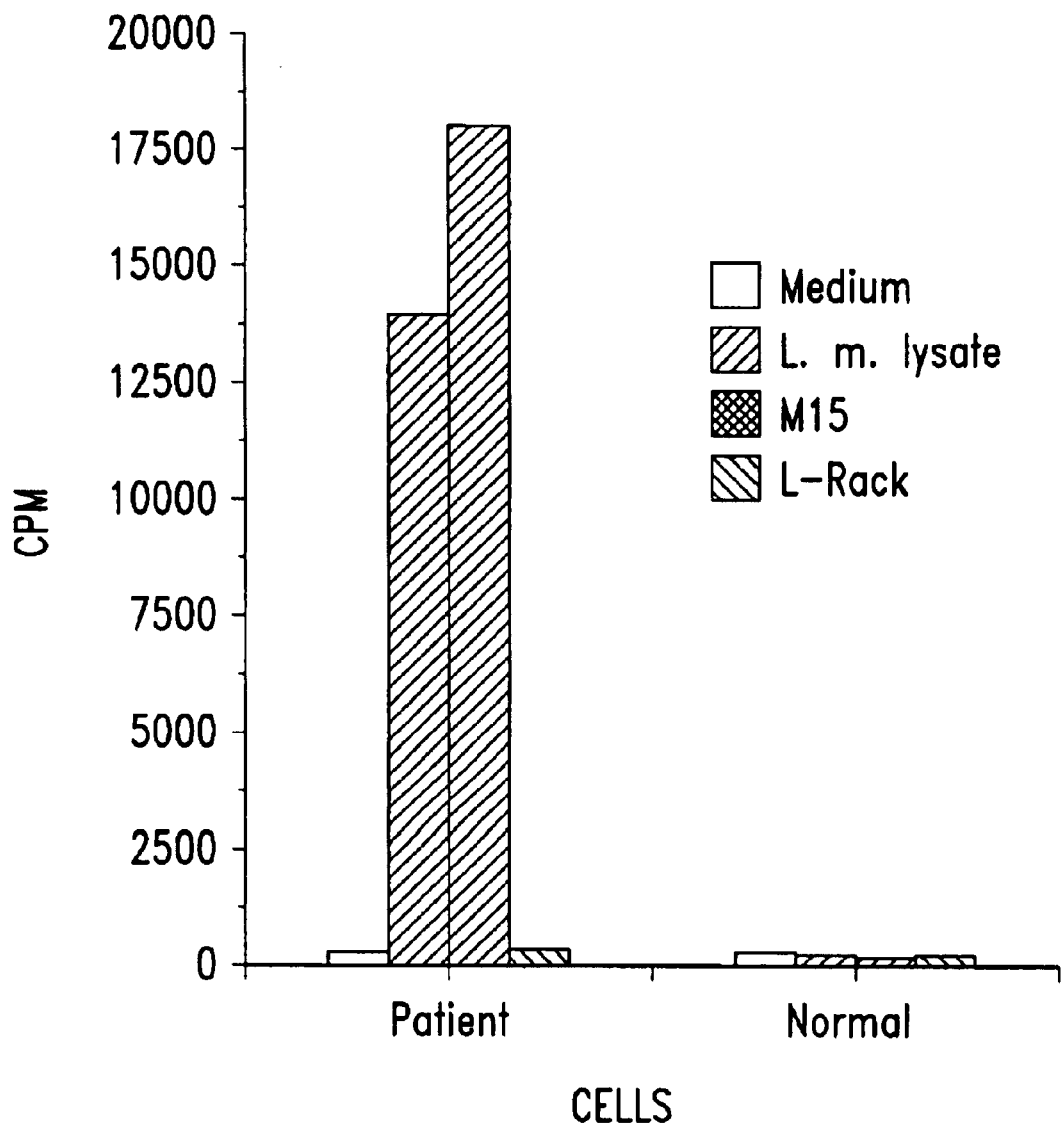
FIG. 17 shows the proliferation of human PBMC, prepared from Leishmania-immune and uninfected individuals, stimulated by M15 as compared to the proliferation stimulated by *L. major* lysate and L-Rack. Values are expressed as cpm.
Figure 18:
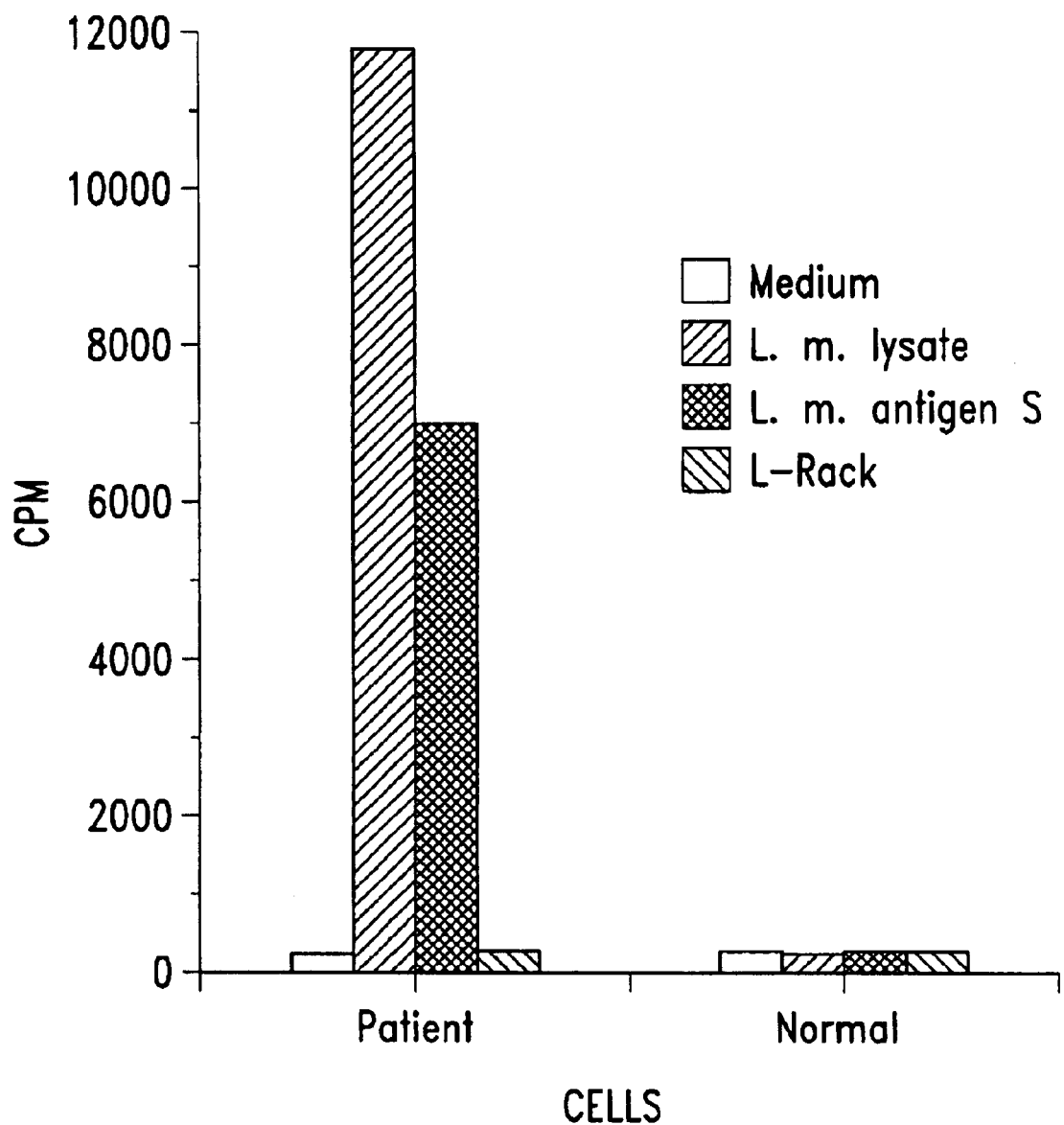
FIG. 18 illustrates the proliferation of human PBMC, prepared from Leishmania-infected and uninfected individuals, stimulated by soluble Leishmania antigens as compared to the proliferation stimulated by culture medium, *L. major* lysate and L-Rack. Values are expressed as cpm.

FIGS. 17 and 18 illustrate the proliferation observed in human PBMC preparations from Leishmania-immune and uninfected individuals following the addition of 10 μg/mL M15 and soluble Leishmania antigens, respectively. These values are compared to the proliferation observed following the addition of culture medium, L. major lysate or L-Rack. The results show that M15 and soluble Leishmania antigens stimulate proliferation in Leishmania-immune PBMC, but not in PBMC obtained from uninfected individuals, demonstrating that M15 and soluble antigens (but not L-Rack) are recognized by PBMC from individuals immune to Leishmania due to a previous infection.

Example 9

Preparation of Lmsp1a and Lmsp9a

This Example illustrates the preparation of two soluble Leishmania antigens, Lmsp1a and Lmsp9a.

A. Purification of Lmsp1a and Lmsp9a From a Mixture of Soluble L. major Antigens A high titer rabbit sera was raised against L. major soluble antigens, prepared as described above in Example 6. Specifically, a New Zealand white rabbit was immunized subcutaneously at multiple sites with 180 μg of L. major soluble antigens in a suspension containing 100 μg muramyl dipeptide and 50% incomplete Freund's adjuvant. Six weeks later the rabbit was given a subcutaneous boost of 100 μg of the same soluble antigen preparation in incomplete Freund's adjuvant. This was followed by two intravenous boosts spaced two weeks apart, each with 100 μg of the soluble antigen preparation. Sera was collected from the rabbit 11 days after the final boost.

Figure 20:
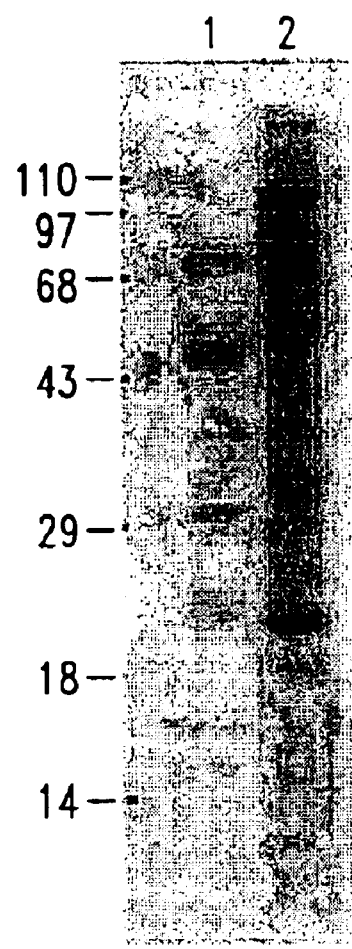
FIG. 20 illustrates the reactivity of rabbit sera raised against soluble Leishmania antigens with Leishmania promastigote lysate (lane 1) and soluble Leishmania antigens (lane 2).

Anti E. coli antibody reactivities were removed from the rabbit sera by pre-adsorbing on nitrocellulose filters containing lysed E. coli. Adsorbed sera were evaluated by Western blot analysis using 10 μg Leishmania promastigote lysate (lane 1) and 1 μg soluble L. major antigen mixture (lane 2). As shown in FIG. 20, the rabbit sera was found to be reactive with seven dominant antigens of the soluble L. major antigen mixture with molecular weights ranging from 18 to>200 kDa. A four times longer exposure of the same blot revealed three additional immunoreactive species with molecular weights less than 18 kDa. The same sera reacted with approximately 10 antigens of the promastigote lysate, but with a pattern significantly different from that observed with the soluble L. major antigens (FIG. 20). This is suggestive of potential post-translational modification of the same antigen before (intracellular localization) and after secretion/shedding. Such modifications may include cleavage of a leader sequence and/or the addition of carbohydrate molecules to the secreted/shed antigens.

The rabbit sera described above was subsequently used to screen an L. major eDNA expression library prepared from L. major promastigote RNA using the unidirectional Lambda ZAP (uni-ZAP) kit (Stratagene) according to the manufacturer's protocol. A total of 70,000 pfu of the amplified cDNA library was screened with the rabbit sera at a 1:250 dilution. Nineteen positive clones were confirmed in the tertiary screening. The phagemid were excised and DNA from each of the 19 clones was sequenced using a Perkin Elmer/Applied Biosystems Division automated sequencer Model 373A. All 19 clones were found to represent two distinct sequences, referred to as Lmsp1a and Lmsp9a. The determined cDNA sequences for Lmsp1a and Lmsp9a are provided in SEQ ID NO: 19 and 21, respectively, with the corresponding amino acid sequences being provided in SEQ ID NO: 20 and 22, respectively.

B. Characterization of Lmsp1a and Lmsy9a

FIG. 21 shows the full-length cDNA (SEQ ID NO: 19) and predicted amino acid sequence (SEQ ID NO: 20) for the antigen Lmsp1a. The EcoRI/XhoI insert is 1019 bp long and contains the following features: a) the last 17 nt of the spliced leader sequence characteristic of all trypanosoma nuclearly encoded MRNA; b) 39 nt of 5' untranslated sequence; c) an open reading frame of 453 nt long coding for a 151 deduced amino acid sequence with a predicted molecular mass of 16.641 kDa; and d) 471 nt of 3' untranslated sequence terminating with a poly A tail. The predicted amino acid sequence contains three potential phosphorylation sites at amino acid residues 3, 85 and 102. In addition, Lmsp1a contains an RGD sequence at residue 104, a sequence that may play a role in parasite invasion of the macrophage. RGD sequences have been shown to mediate the binding of various adhesion proteins to their cell surface receptors. There is no obvious leader sequence (secretory signal) at the amino terminal portion suggesting that the protein might be shed or excreted. Lmsp1a appears to be one of the most abundant antigens found in the culture supernatant of live promastigote, since 17 of the 19 clones contain sequences of variable lengths identical to Lmsp1a.

Comparison of the amino acid sequence of Lmps1a with known sequences using the DNA STAR system (Version 87) revealed that Lmsp1a shares between 65% to 70% homology with the eukaryotic nucleoside diphosphate kinase protein, also referred to in the mouse and human as a tumor metastasis inhibitor gene.

Figure 22:
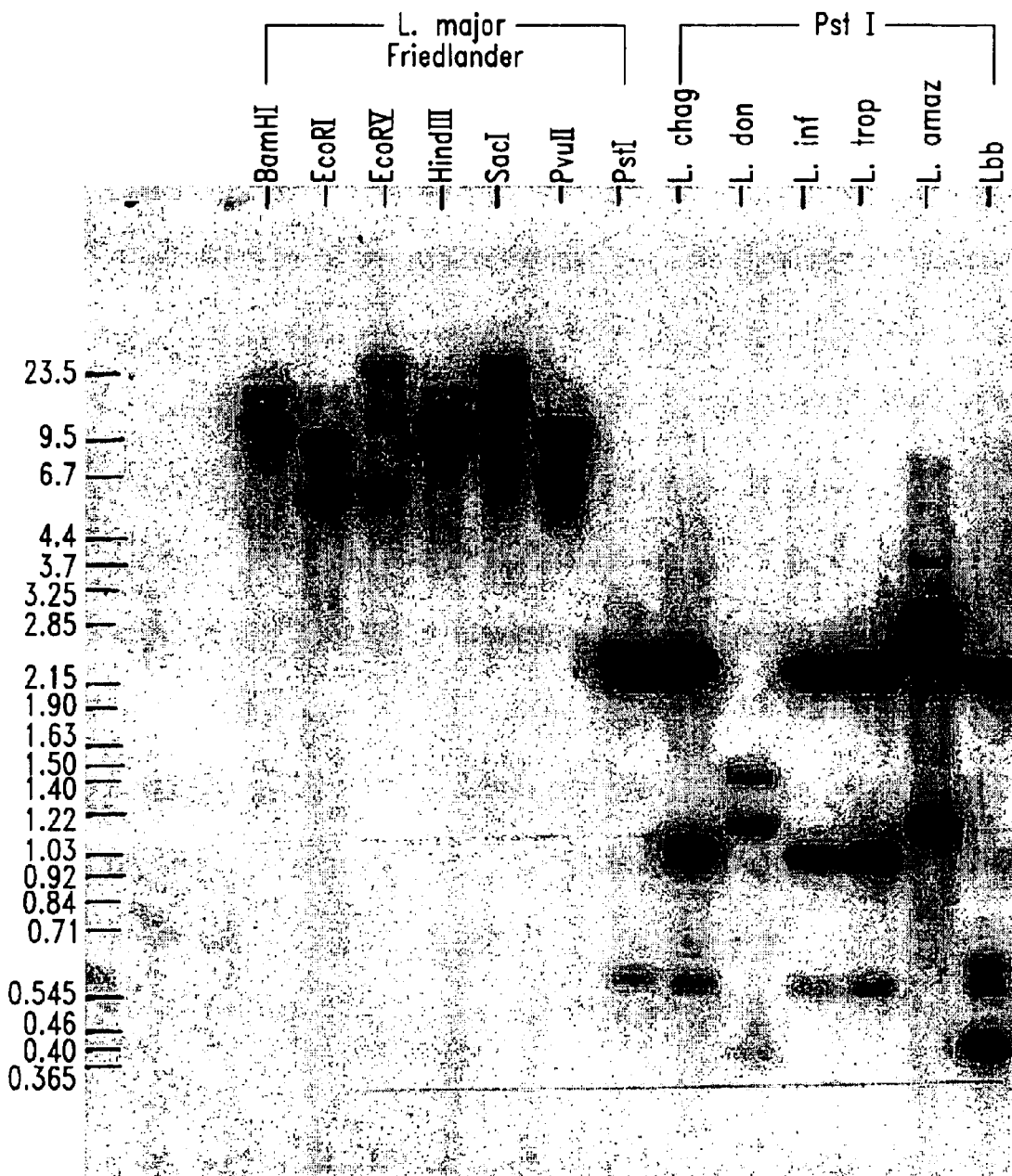
FIG. 22 shows a Southern blot of genomic DNA from *L. major* digested with a panel of restriction enzymes (lanes 1 to 7) and six other Leishmania species digested with PstI (lanes 8 to 13) probed with the full-length cDNA insert of Lmspla.

Southern blot analysis of genomic DNA from L. major (Friedlander strain) digested with a panel of restriction enzymes (lanes 1 to 7) and six other Leishmania species of different geographic locations digested with PstI (lanes 8 to 13) using the full-length cDNA insert of Lmps1a, demonstrated that Lmsp1a is present in all the species characterized with a high degree of conservation (FIG. 22). This suggests evolutionary significance for the maintenance of Lmsp1a and the existence of homologous species among all the Leishmania species.

The remaining two cDNA clones isolated from the soluble L. major antigen mixture represent identical sequences (referred to as Lmsp9a; SEQ ID NO: 21), suggesting that the two copies resulted from amplification of the primary library. Sequencing of the Lmsp9a cDNA revealed that the clone does not contain the full length 5' sequence since it is lacking both the spliced leader and 5' untranslated sequences. The 3' end of the cDNA contains a poly A stretch, as would be expected for a Leishmania mRNA. Of the predicted translated sequence (SEQ ID NO: 22), 34 of the 201 amino acids (17%) represent cysteine residues. Comparison of the predicted protein sequence with those of known proteins as described above, revealed some homology with other cysteine rich proteins such as the major surface trophozoite antigen of Giardia lamblia and furin proteases.

Example 10

Preparation and Characterization of MAPS-1A

This Example illustrates the preparation and characterization of the Leishmania antigen MAPS-1A (SEQ ID NO: 24).

A pool of sera was obtained from 5 BALB/c mice that had been given a primary immunization and two boosts with crude L. major promastigote culture supernatant as described below in Example 12. These mice were subsequently shown to be protected when challenged with a dose of live L. major promastigotes generally found to be lethal. The mouse sera thus obtained were used to screen an L. major amastigote cDNA expression library prepared as described in Example 1. Several seroreactive clones were isolated and sequenced using a Perkin Elmer/Applied Biosystems Division automated sequencer Model 373A (Foster City, Calif.).

One of these clones, referred to herein as MAPS-1A, was found to be full-length. Comparison of the cDNA and deduced amino acid sequences. for MAPS-1A (SEQ ID Nos: 23 and 24, respectively) with known sequences in the gene bank using the DNA STAR system revealed no significant homologies to known Leishmania sequences, although some sequence similarity was found to a group of proteins, known as thiol-specific antioxidants, found in other organisms.

Figure 23:
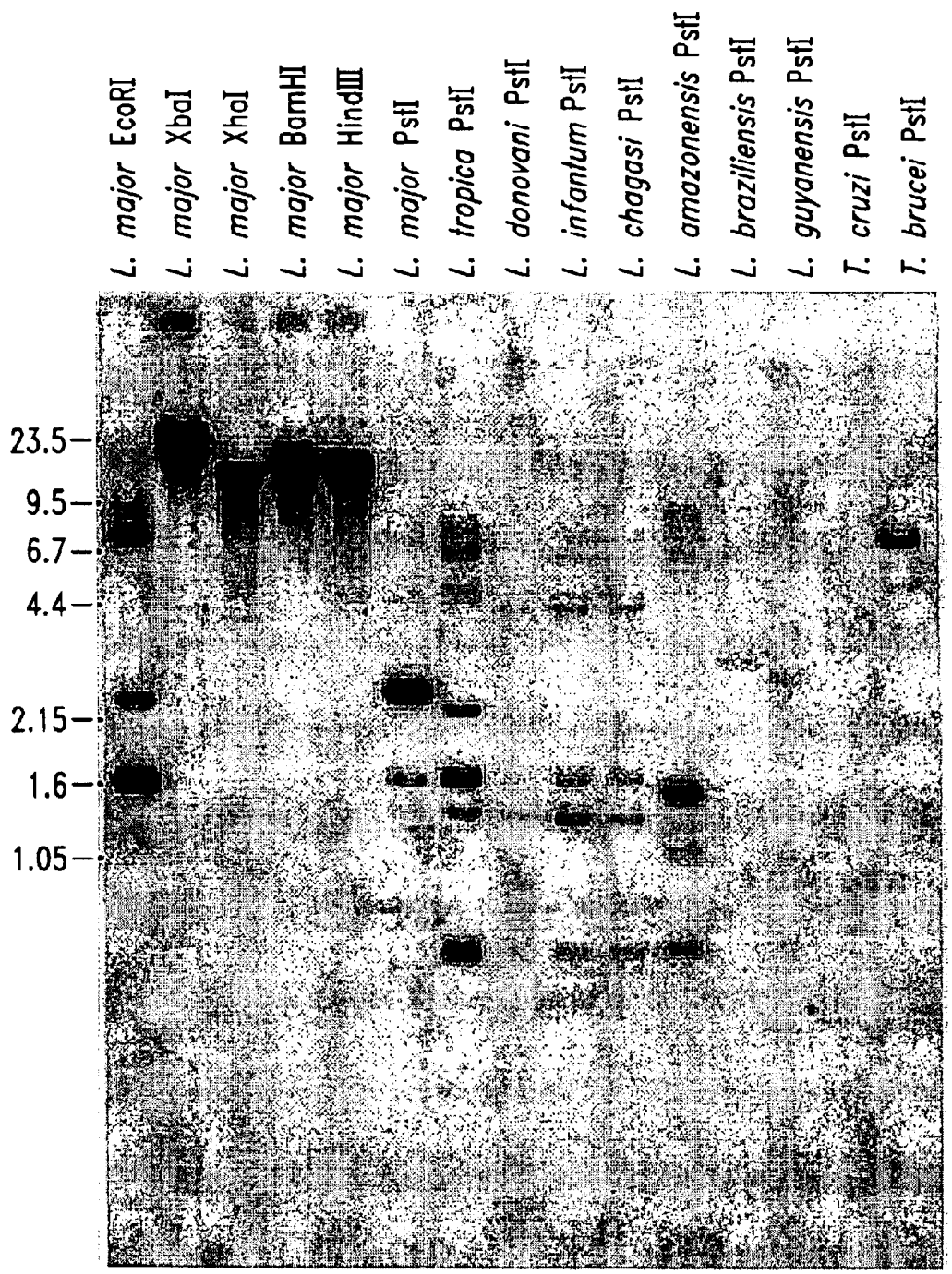
FIG. 23 shows a Southern blot of genomic DNA from *L. major* digested with a panel of restriction enzymes, six other Leishmania species digested with PstI and the infectious pathogens *T. cruzi* and *T brucei*, probed with the full-length cDNA insert of the Leishmania antigen MAPS-1A.

Recombinant MAPS-1A protein having an amino-terminal HIS-Tag was prepared using a high level *E. coli* expression system and recombinant protein was purified by affinity chrofatography as described in Example 1. Southern blot analysis of genomic DNA from *L. major* digested with a panel of restriction enzymes, seven other Leishmania species digested with PstI, and two other infectious-disease pathogens (*T. cruzi* and *T brucei*), using the full length insert of MAPS-1A, demonstrated that MAPS-1A is present in all eight Leishmania species tested (FIG. 23). Northern blot analysis of *L. major* promastigote and amastigote RNAs indicated that MAPS-1A is constitutively expressed.

Using oligonucleotide primers based on the MAPS-1A cDNA sequence provided in SEQ ID NO: 23, the corresponding gene was isolated from *L. tropica* by means of PCR (using 30 cycles of the following temperature step sequence: 94° C., 1 minute; 50° C., 1 minute; 72° C., 1 minute) The determined cDNA sequence for the *L. tropica* MAPS-1A protein is provided in SEQ ID NO: 25, with the corresponding amino acid sequence being provided in SEQ ID NO: 26.

Figure 24:
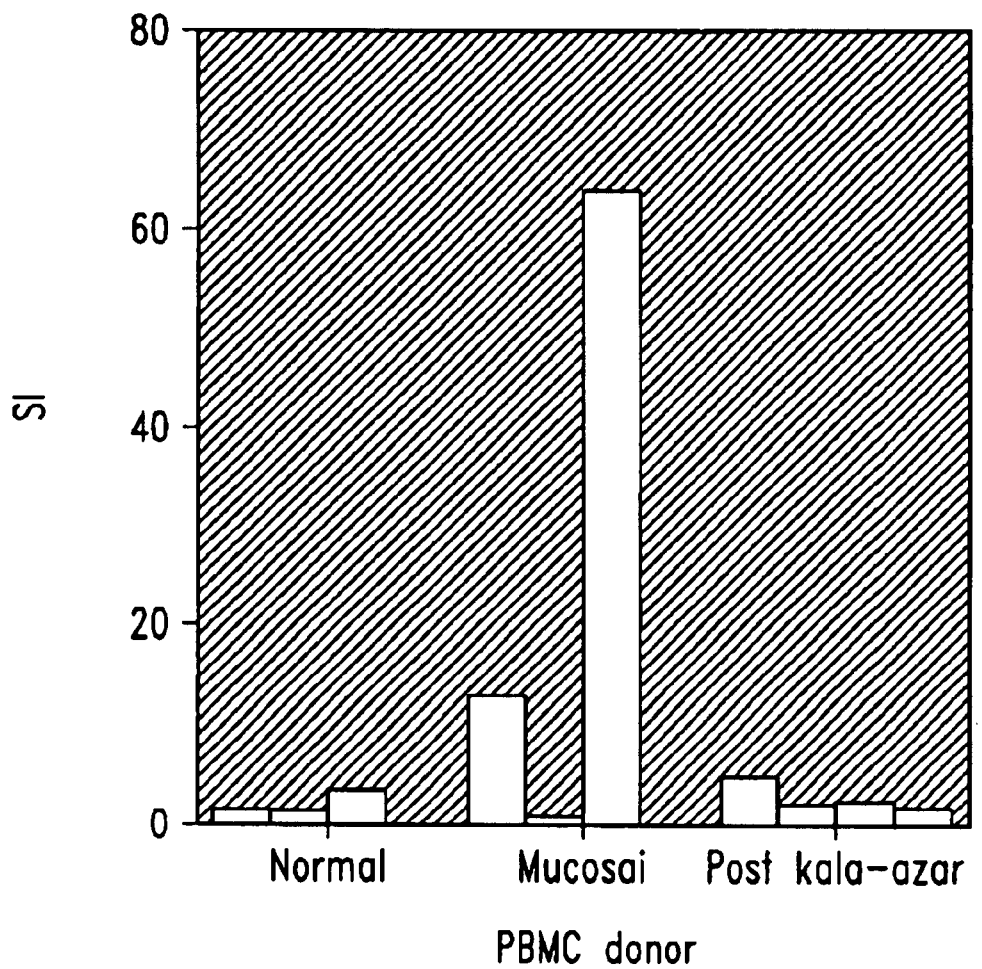
FIG. 24 illustrates the proliferation of PBMC isolated from uninfected-individuals, patients with active mucosal leishmaniasis and patients post kala-azar infection, stimulated by MAPS-1A.

The ability of recombinant MAPS-1A to stimulate cell proliferation was investigated as follows. PBMC from 3 *L. braziliensis*-infected patients having active mucosal leishmaniasis, from 4 patients post kala-azar infection (previously infected with *L. chagasi* and/or *L. donovani*) and from 3 uninfected-individuals were prepared as described above in Example 7. The ability of MAPS-1A to stimulate proliferation of these PBMC was determined as described in Example 8 above. As shown in FIG. 24, significant levels of MAPS-1A specific PBMC proliferation were seen in 2 of the 7, Leishmania patients.

Figure 25:
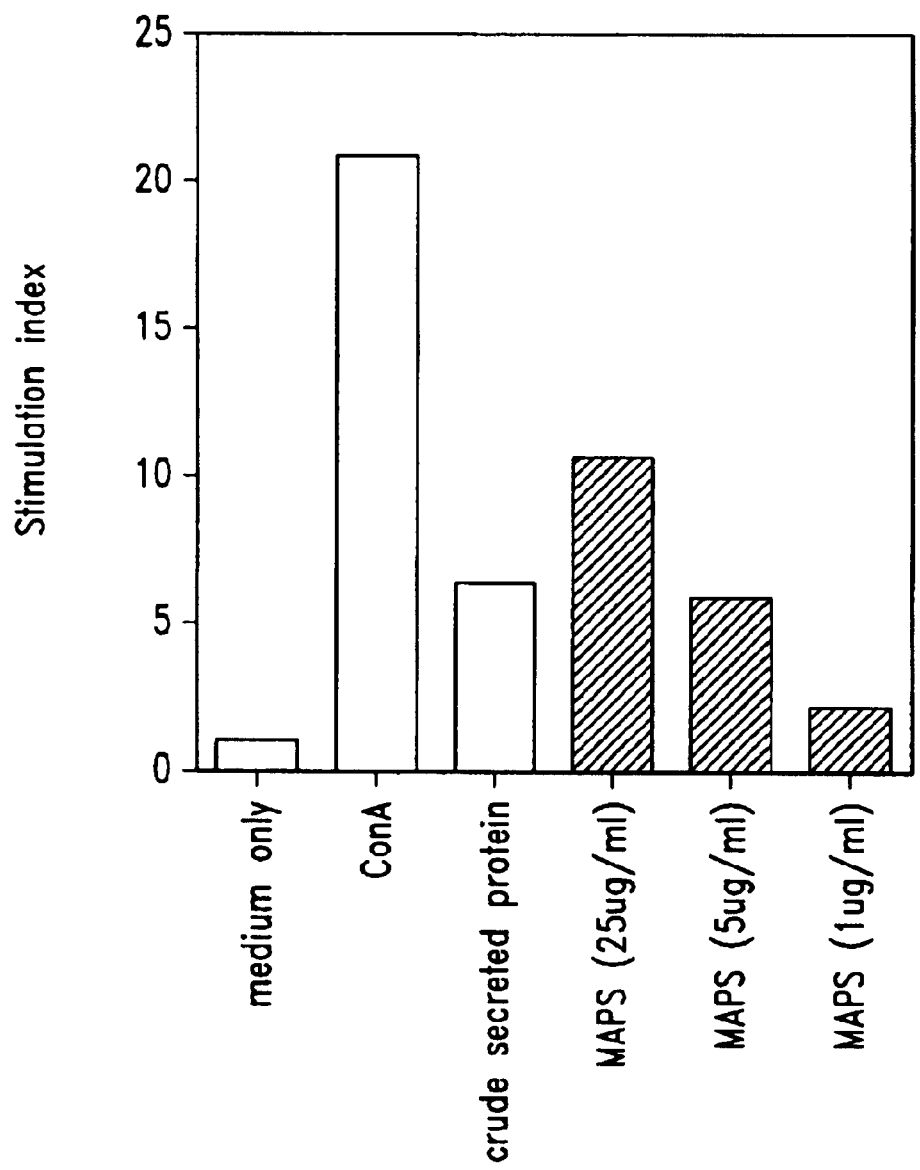
FIG. 25 illustrates the proliferation of murine lymph node cultures stimulated by MAPS-1A.

The ability of MAPS-1A to stimulate proliferation in mice lymph node cultures was determined as described in Example 8. FIG. 25 shows the amount of proliferation stimulated by MAPS-1A (at 25 μg/ml, 5 μg/ml and 1 μg/ml) as compared to that stimulated by the positive control ConA and by crude *L. major* promastigote supernatant proteins, 20 days post-infection with *L. major*. Cells isolated 20 days post-infection were highly responsive to MAPS-1A, whereas cells isolated 10 days post-infection were unresponsive.

Example 11

Immunoreactivity of Soluble Leishmania Antigens With Sera From Leishmania-Infected Patients The reactivity of MAPS-1A with sera from uninfected individuals, from human leishmaniasis patients with cutaneous infection, from human patients with acute visceral leishmaniasis, and from *L. major*-infected BALB/c mice was determined as follows.

Assays were performed in 96-well plates coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/0.1% Tween 20™.

The enyzme conjugate (horseradish peroxidase—Protein A, Zymed, San Francisco, Calif.) was then diluted 1:10,000 in PBS/0.1% Tween 20™/0.1% BSA, and 50 μL of the diluted conjugate was added to each well and incubated for 30 minutes at room temperature. Following incubation, the wells were washed five times with PBS/0. 1% Tween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 nm.

Figure 26:
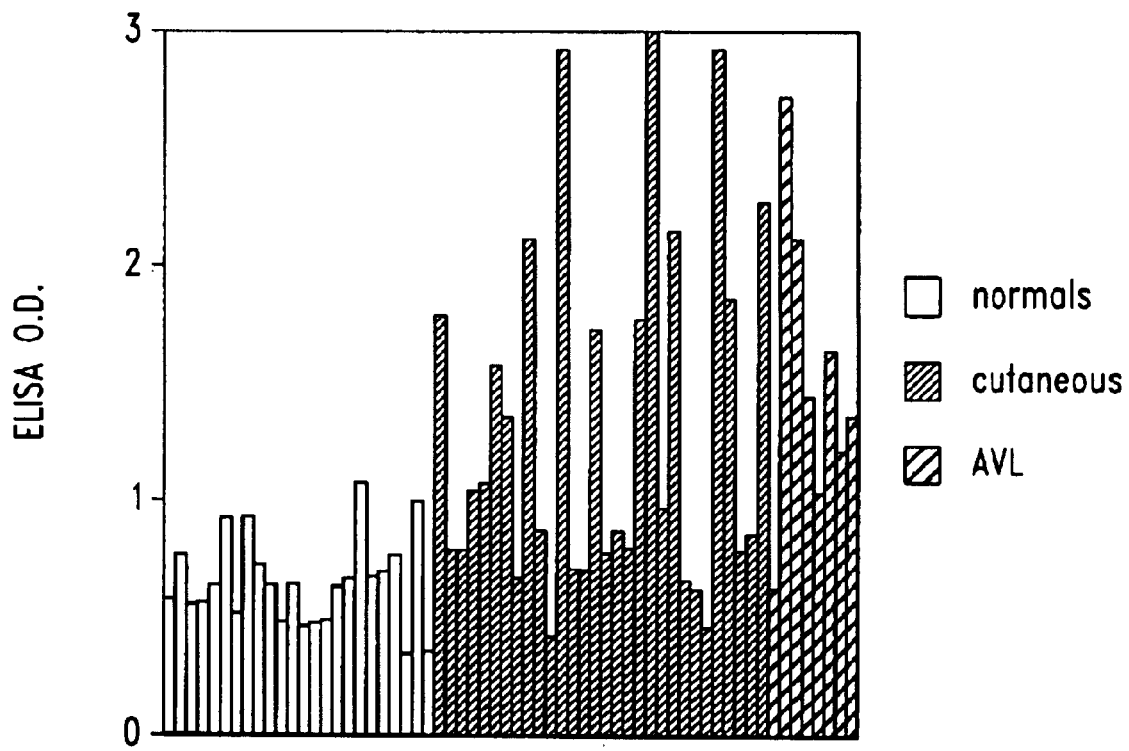
FIG. 26 illustrates the reactivity of MAPS-1A with sera from human leishmaniasis patients.
Figure 27:
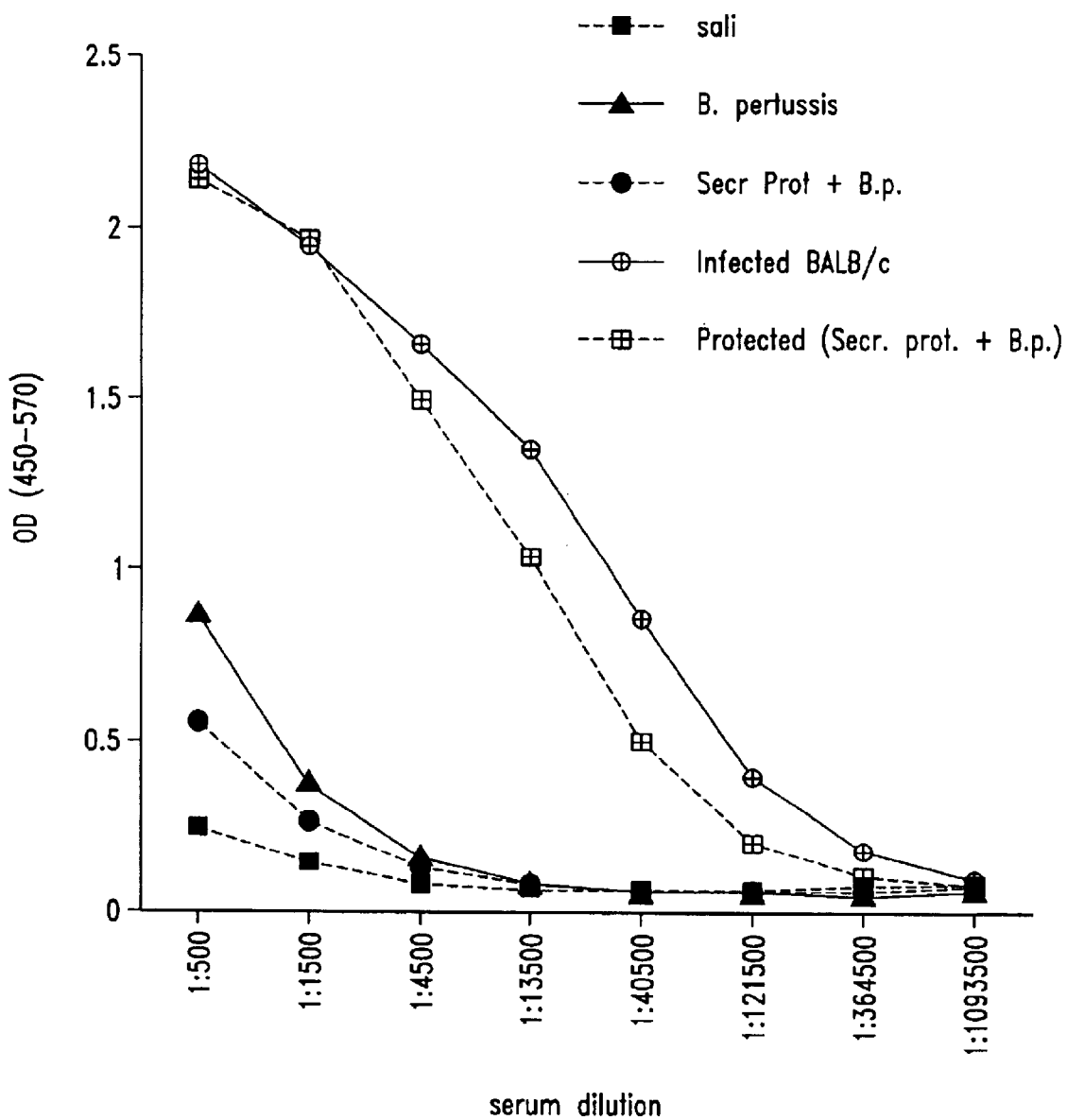
FIG. 27 illustrates the reactivity of MAPS-1A with sera from mice immunized against and/or infected with leishmaniasis.

As shown in FIG. 26, approximately 50% of the samples from human leishmaniasis patients showed reactivities with recombinant MAPS-1A substantially above background. FIG. 27 shows the reactivity of MAPS-1A with increasing dilutions of sera from BALB/c mice previously administered either (i) saline solution; (ii) the adjuvant *B. pertussis*; (iii) soluble Leishmania antigens plus *B. pertussis*; (iv) live *L. major* promastigotes; or (v) soluble Leishmania antigens plus *B. pertussis* followed by live *L. major* promastigotes (as described below in Example 12). Considerably higher absorbances were seen with sera from mice infected with live *L. major* promastigotes and with mice infected with live *L. major* promastigotes following immunization with soluble Leishmania antigens plus *B. pertussis*, than with sera from the other three groups of mice, indicating that anti-MAPS-1A antibody titers increase following Leishmania infection.

Example 12

Use of Leishmania Antigens for Vaccination Against Leishmania Infection

This example illustrates the effectiveness of Leishmania antigens in conferring protection against disease in the experimental murine leishmaniasis model system. For a discussion of the murine leishmaniasis model system see, for example, Reiner et al. *Annu. Rev. Immunol.*, 13:151–77, 1995.

Figure 28:
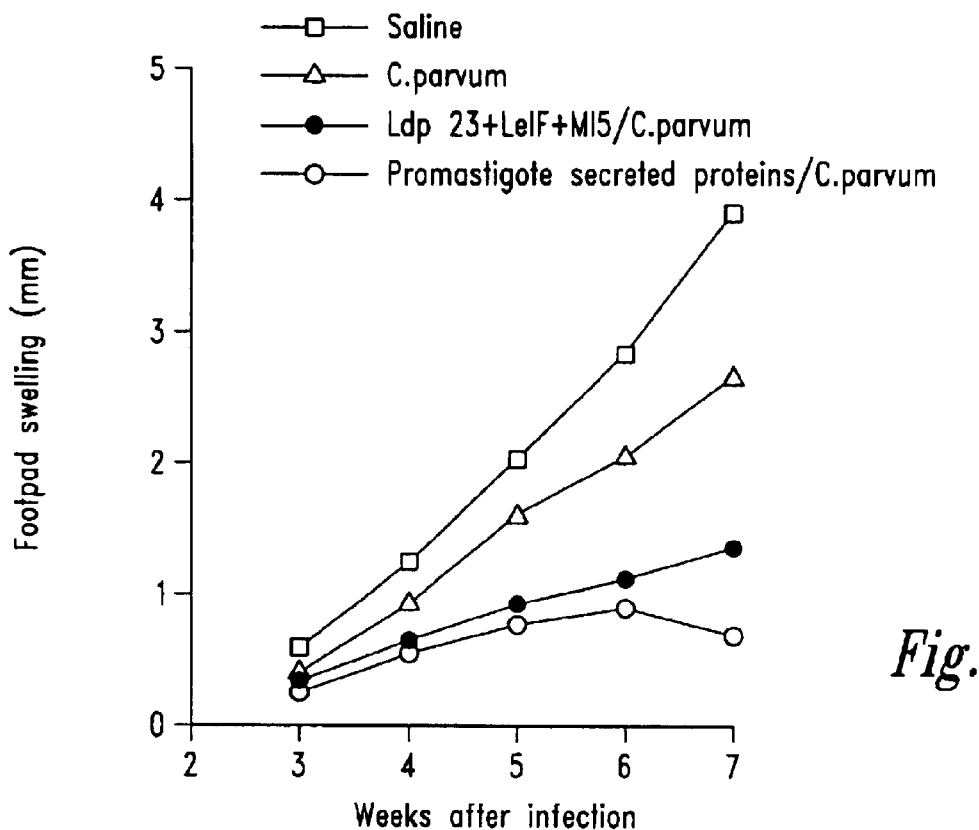
FIG. 28 illustrates the effectiveness of immunization with either soluble Leishmania antigens or a mixture of Ldp23, LbeiF4A and M15 plus adjuvant in conferring protection against infection (as measured by footpad swelling) in a murine leishmaniasis model system, as compared to the administration of adjuvant alone.
Figure 29:
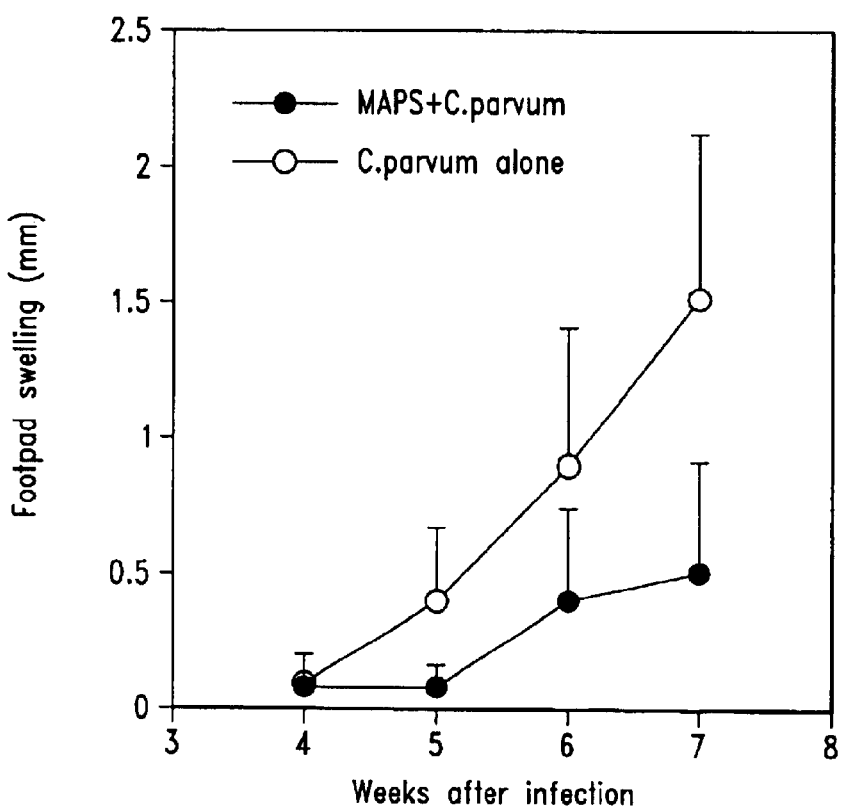
FIG. 29 illustrates the effectiveness of immunization with MAPS-1A plus adjuvant in conferring protection against infection (as measured by footpad swelling) in a murine leishmaniasis model system, as compared to the administration of adjuvant alone.

The effectiveness of (i) crude soluble Leishmania antigens, (ii) MAPS-1A, and (iii) a mixture of Ldp23, LbeIF4A and M15, as vaccines against Leishmania infection was determined as follows. BALB/c mice (5 per group) were immunized intra-peritoneally three times at biweekly intervals with either (i) 30 μg crude soluble Leishmania antigens, (ii)20 μg MAPS-1A or (iii) a mixture containing 10 μg each of LeIF, Ldp23 and M15, together with 100 μg of the adjuvant *C. parvum*. Two control groups were immunized with either saline or *C. parvum* alone. Two weeks after the last immunization, the mice were challenged with $2\times10^5$ late-log phase promastigotes of *L. major*. Infection was monitored weekly by measurement of footpad swelling. The amount of footpad swelling seen in mice immunized with either crude soluble Leishmania antigens, a mixture of Ldp23, LbeiF4A and M15 (FIG. 28), or MAPS-1A (FIG. 29) was significantly less than that seen in mice immunized with *C. parvum*. alone. These results demonstrate that the Leishmania antigens of the present invention are effective in conferring protection against Leishmania infection.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising an immunogenic portion of the amino acid sequence recited in SEQ ID NO: 2, wherein said immunogenic portion stimulates a Leishmania-specific cellular immune response.

2. The polypeptide of claim 1, comprising amino acids 1–546 of SEQ ID NO:2.

3. An isolated polypeptide comprising an immunogenic portion of the amino acid sequence of SEQ ID NO: 22, wherein said immunogenic portion stimulates a Leishmania-specific cellular immune response.

4. An isolated polypeptide comprising an immunogenic portion of the amino acid sequence of SEQ ID NO: 24, wherein said immunogenic portion stimulates a Leishmania-specific cellular immune response.

5. An isolated polypeptide comprising an immunogenic portion of the amino acid sequence of SEQ ID NO: 26, wherein said immunogenic portion stimulates a Leishmania-specific cellular immune response.

6. An isolated polypeptide comprising an immunogenic portion of the amino acid sequence of SEQ ID NO: 20, wherein said immunogenic portion stimulates a Leishmania-specific cellular immune response.

7. A pharmaceutical composition comprising a polypeptide according to claim 1, and a physiologically acceptable carrier.

8. A pharmaceutical composition comprising a polypeptide of claim 3 and a physiologically acceptable carrier.

9. A pharmaceutical composition comprising a polypeptide of claim 4 and a physiologically acceptable carrier.

10. A pharmaceutical composition comprising a polypeptide of claim 5 and a physiologically acceptable carrier.

11. A pharmaceutical composition comprising an isolated polypeptide according to claim 6 and a physiologically acceptable carrier.

12. A vaccine comprising an isolated polypeptide according to claim 1 and a non-specific immune response enhancer.

13. A vaccine according to claim 12 wherein the non-specific immune response enhancer is an immunogenic portion of a Leishmania antigen having the amino acid sequence recited in SEQ ID NO:10.

14. A vaccine according to any one of claim 12 and, further comprising a delivery vehicle.

15. The vaccine of claim 14 wherein the delivery vehicle is a biodegradable microsphere.

16. A vaccine comprising a polypeptide according to claim 4 and a non-specific immune response enhancer.

\* \* \* \* \*